US011154253B2

(12) United States Patent
Cabrera, Jr. et al.

(10) Patent No.: US 11,154,253 B2
(45) Date of Patent: Oct. 26, 2021

(54) SYSTEMS AND METHODS FOR HEALTH DATA VISUALIZATION AND USER SUPPORT TOOLS FOR CONTINUOUS GLUCOSE MONITORING

(71) Applicant: DexCom, Inc., San Diego, CA (US)

(72) Inventors: Esteban Cabrera, Jr., San Diego, CA (US); Lauren Danielle Armenta, San Diego, CA (US); Scott M. Belliveau, San Diego, CA (US); Jennifer Blackwell, San Diego, CA (US); Leif N. Bowman, San Diego, CA (US); Rian Draeger, San Diego, CA (US); Arturo Garcia, Chula Vista, CA (US); Timothy Joseph Goldsmith, San Diego, CA (US); John Michael Gray, San Diego, CA (US); Andrea Jean Jackson, Solana Beach, CA (US); Apurv Ullas Kamath, San Diego, CA (US); Katherine Yerre Koehler, Solana Beach, CA (US); Paul Kramer, Austin, TX (US); Aditya Sagar Mandapaka, San Diego, CA (US); Michael Robert Mensinger, San Diego, CA (US); Sumitaka Mikami, San Diego, CA (US); Gary A. Morris, La Jolla, CA (US); Hemant Mahendra Nirmal, Chula Vista, CA (US); Paul Noble-Campbell, Austin, TX (US); Philip Thomas Pupa, San Diego, CA (US); Eli Reihman, San Diego, CA (US); Peter C. Simpson, Cardiff by the Sea, CA (US); Brian Christopher Smith, San Marcos, CA (US); Atiim Joseph Wiley, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1097 days.

(21) Appl. No.: 15/674,442

(22) Filed: Aug. 10, 2017

(65) Prior Publication Data
US 2018/0042558 A1 Feb. 15, 2018

Related U.S. Application Data

(60) Provisional application No. 62/374,539, filed on Aug. 12, 2016.

(51) Int. Cl.
*A61B 5/00* (2006.01)
*G06F 1/16* (2006.01)
*G06F 3/0484* (2013.01)
*G16H 15/00* (2018.01)
*G16H 40/67* (2018.01)
*G16H 50/20* (2018.01)
*G16H 70/40* (2018.01)
*G16H 50/30* (2018.01)
*G16H 40/63* (2018.01)
*A61B 5/145* (2006.01)
*G06F 3/0488* (2013.01)
*G06F 17/18* (2006.01)
*G06F 16/00* (2019.01)

(52) U.S. Cl.
CPC .......... *A61B 5/7275* (2013.01); *A61B 5/0022* (2013.01); *A61B 5/14532* (2013.01); *A61B 5/743* (2013.01); *A61B 5/746* (2013.01); *G06F 1/163* (2013.01); *G06F 3/0484* (2013.01); *G06F 3/0488* (2013.01); *G06F 3/04847* (2013.01); *G06F 17/18* (2013.01); *G16H 15/00* (2018.01); *G16H 40/63* (2018.01); *G16H 40/67* (2018.01); *G16H 50/20* (2018.01); *G16H 50/30* (2018.01); *G16H 70/40* (2018.01); *G06F 16/00* (2019.01)

(58) Field of Classification Search
CPC ..................................................... A61B 5/7275
USPC .......................................................... 702/19
See application file for complete search history.

(56) References Cited

U.S. PATENT DOCUMENTS

| | | | |
|---|---|---|---|
| 6,001,067 A | 12/1999 | Shults et al. | |
| 6,424,847 B1 | 6/2002 | Mastrototaro et al. | |
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 6,931,327 B2 | 8/2005 | Goode et al. | |
| 7,310,544 B2 | 12/2007 | Brister et al. | |
| 7,591,801 B2 | 9/2009 | Brauker et al. | |
| 2005/0027463 A1 | 2/2005 | Goode et al. | |
| 2005/0043598 A1 | 2/2005 | Goode et al. | |
| 2005/0154271 A1 | 7/2005 | Rasdal et al. | |

(Continued)

FOREIGN PATENT DOCUMENTS

WO WO 2013/022775 2/2013
WO WO 2013/184566 12/2013

OTHER PUBLICATIONS

International Preliminary Report on Patentability for Application No. PCT/US2017/046343 dated Feb. 21, 2019, 8 pages.

(Continued)

*Primary Examiner* — Jerry Lin
(74) *Attorney, Agent, or Firm* — Knobbe Martens Olson & Bear LLP

(57) ABSTRACT

Disclosed are systems and methods for generating graphical displays of analyte data and/or health information. In some implementations, the graphical displays are generating based on a self-referential dataset that are modifiable based on identified portions of the data. The modified graphical displays can indicate features in the analyte data of a host.

26 Claims, 40 Drawing Sheets

(56) References Cited

U.S. PATENT DOCUMENTS

| | | |
|---|---|---|
| 2005/0192557 A1 | 9/2005 | Brauker et al. |
| 2005/0203360 A1 | 9/2005 | Brauker et al. |
| 2006/0020187 A1 | 1/2006 | Brister et al. |
| 2006/0222566 A1 | 10/2006 | Brauker et al. |
| 2007/0016381 A1 | 1/2007 | Kamath |
| 2007/0027385 A1 | 2/2007 | Brister et al. |
| 2007/0032706 A1 | 2/2007 | Kamath et al. |
| 2007/0197890 A1 | 8/2007 | Boock et al. |
| 2007/0203966 A1 | 8/2007 | Brauker et al. |
| 2007/0208245 A1 | 9/2007 | Brauker et al. |
| 2008/0033254 A1 | 1/2008 | Kamath et al. |
| 2008/0119703 A1 | 5/2008 | Brister et al. |
| 2009/0240120 A1 | 9/2009 | Mensinger et al. |
| 2009/0299156 A1 | 12/2009 | Simpson et al. |
| 2012/0078071 A1 | 3/2012 | Bohm et al. |
| 2013/0035865 A1 | 2/2013 | Majou et al. |
| 2014/0012511 A1 | 1/2014 | Mensinger et al. |
| 2018/0042559 A1 | 2/2018 | Esteban et al. |

OTHER PUBLICATIONS

International Search Report and Written opinion for Application No. PCT/US2017/046343 dated Oct. 20, 2017, 8 pages.
Esri ArcGIS Pro: "Data Clock"; Jan. 3, 2001; [retrieved from the Internet: URL: https://pro.arcgis.com/en/pro-app/help/analysis/geoprocessing/charts/data-clock.htm on Feb. 13, 2020], 3 pages.
Extended European Search Report dated Feb. 24, 2020 for Application No. 17840295.4.

1700

1702  Temp basal
.05 alpha
B15CE7
177,92,231

1704 
15min

Bolus
.08 alpha
B15CE7
177,92,231
corner: 8pt radius
Minimum width is 15 min
(the width can change due to delivery time)

1706  Extended Bolus
.08 alpha
B15CE7
177,92,231
corner: 8pt radius

1708 Combo Bolus
.08 alpha
B15CE7
177,92,231
corner: 8pt radius

1710  Basal
.05 alpha
B15CE7
177,92,231
no corner radius

SYSTEMS AND METHODS FOR HEALTH DATA VISUALIZATION AND USER SUPPORT TOOLS FOR CONTINUOUS GLUCOSE MONITORING

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Appl. No. 62/374,539 filed on Aug. 12, 2016. The aforementioned application is incorporated by reference herein in its entirety, and is hereby expressly made a part of this specification.

TECHNICAL FIELD

The present disclosure relates generally to continuous monitoring of analyte values received from an analyte sensor system. More particularly, the present disclosure is directed to systems, methods, apparatuses, and devices for generating dynamic data structures and graphical displays.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value, but will not know if his blood glucose value is going up (higher) or down (lower), due to limitations of conventional methods.

Consequently, a variety of non-invasive, transdermal (e.g., transcutaneous) and/or implantable electrochemical sensors are being developed for continuously detecting and/or quantifying blood glucose values. Continuous glucose monitors have been increasing in popularity as an easy way to monitor glucose levels. In the past, patients sample their blood glucose levels several times throughout a day, such as in the morning, around lunch, and in the evening. The levels can be measured by taking a small blood sample of the patient and measuring the glucose levels with a test strip or glucose meter. This technique, however, has drawbacks because patients would prefer to not have to take a blood sample, and users do not know what their blood glucose levels are throughout the day between the samples.

One potentially dangerous timeframe is at night because a patient's glucose levels can fall dangerously low during sleep. As a result, continuous glucose monitors have gained popularity by providing a sensor that continuously measures glucose levels of a patient and transmits the measured glucose levels wirelessly to a display. This allows the patient or patient's caregiver to monitor the patient's glucose levels throughout the day and even set alarms for when glucose levels reach a predefined level or experience a defined change.

Initially, continuous glucose monitors wirelessly transmitted data relating to glucose levels to a dedicated display. The dedicated display is a medical device designed to display glucose levels, trending patterns, and other information for a user. However, with the increasing popularity of smart phones and software applications (apps) executing on smart phones, some users prefer to avoid having to carry a dedicated display. Instead, some users prefer to monitor their glucose levels using a dedicated software app executing on their mobile computing device, such as a smart phone, tablet or wearable device like a smartwatch or smart glasses. Still other users may prefer the flexibility of having access to their glucose and glucose related data on other mobile or stationery computing devices in addition to dedicated displays.

SUMMARY

One embodiment includes a system, wherein the system includes: a continuous analyte sensor configured to obtain analyte measurements of a host; a wireless transmitter configured to receive the analyte measurements from the continuous analyte sensor and at least partially process the analyte measurements to produce one or more datasets of analyte data, each dataset including an analyte concentration value associated with a time for one or more of the analyte measurements, wherein the wireless transmitter includes an energy storage unit, a data converter unit, a processing unit and a transmitter unit; and an analyte data processing module operable on a mobile computing device in wireless communication with the wireless transmitter, the analyte data processing module configured to receive and process the one or more datasets from the wireless transmitter to produce a graphical display on the mobile computing device, wherein the graphical display includes an arrangement of the analyte concentration values over a plurality of time intervals that is graphically modified to indicate one or more patterns in analyte data.

In one aspect of the system, the analyte data processing module is further configured to: aggregate groups of analyte data; flag the groups of analyte data based on additional information corresponding to one or more graphical displays; arrange the flagged groups of analyte concentration values; and generate a self-referential dataset from the arranged groups of analyte concentration values.

In one aspect, generating the self-referential dataset further includes one or more of: flagging the analyte data based on one or more high and low thresholds of analyte in the host; flagging the analyte data based on performing statistical analysis of the analyte data; and flagging the analyte data based on contextual data related to when the analyte data was obtained.

In one aspect, the contextual data includes: data indicative of one or more physical locations where analyte data was obtained, the relationship between the host and the physical locations, the frequency of visiting the physical locations, meals taken, type and intensity of exercise, type and amount of insulin administered and likelihood of the host being asleep or awake when the analyte data was obtained.

In another aspect, the analyte data processing module is further configured to produce a graphical display on the mobile computing device by: receiving a user's input including the user's desired graphical display; receiving display configuration data; regenerating the self-referential dataset when the self-referential dataset does not contain data to form the desired graphical display; and reformatting the self-referential dataset based on the user's input and the display configuration data.

In some aspects, the analyte data processing module is further configured to modifying the graphical display by: scanning the self-referential dataset for threshold flags and modifying the graphical display based on threshold flags; scanning the self-referential dataset for statistical analysis flags and modifying the graphical display based on statistical analysis flags; and scanning the self-referential dataset for analyte contextual data flags and modifying the graphical display based on contextual data flags.

In one aspect, modifying the graphical display includes: introducing or using one or more of: colors, gradients of colors or shades, transparency, opacity, buffer zones, graphical icons, arrows, animations, texts, numbers and gradual fading.

In one aspect, the arrangement includes a spatial-temporal organization of the analyte concentration values in which the analyte concentration values are positioned along a first direction according to a first time scale and along a second direction according to a second time scale, and the analyte level of the analyte concentration values are composed by one or more of a shape, color, shading, or size based on a magnitude of the analyte level.

In one aspect, the first direction and the second direction are linear directions.

In another aspect, the first direction is a curved direction and the second direction is a radial direction.

In some aspects, the first time scale is hourly and the second time scale is daily.

In one aspect, the first time scale is hourly and the second time scale is daily, wherein the graphical modification includes an analyte level trace overlaid over the graphical display such that higher analyte levels are closer to an outer curved region of the graphical display and lower analyte levels are closer to an inner curved region of the graphical display, or vice versa.

In one aspect, the higher analyte levels are in a first color, the lower analyte levels are in a second color, and analyte levels between the higher and lower analyte levels are in a third color.

In one aspect, the analyte level trace includes an average analyte level of daily analyte concentration values.

In one aspect, the analyte level trace includes a current analyte level over the hourly time scale.

In another aspect, the modification of the graphical display includes displaying a clustering of colors, gradients of colors or shades, lining up of regions, or lighter or darker shades of overlapping regions to modify the arrangement of the analyte concentration values over the plurality of time intervals.

In one aspect, the one or more patterns indicate the analyte concentration values relative to high and low analyte level thresholds for the host.

In one aspect, the plurality of time intervals includes 24 hour periods over 7 days.

In one aspect, the graphical display includes an isometric graph plotted over 24 hour periods over 7 days.

In one aspect, the isometric graph is displayable in a three dimensional view.

In one aspect, the graphical display includes concentric rings.

In another aspect, the graphical display includes a fan-shaped graph.

In one aspect, the graphical display includes one or more line graphs.

Another embodiment includes a computer-implemented method, which includes: receiving, at a mobile computing device, analyte data obtained from a continuous analyte sensor device, wherein the analyte data includes analyte concentration values each associated with a measurement of time; processing, at the mobile computing device, the analyte data to produce an arrangement of the analyte concentration values over a plurality of time intervals; generating a graphic of the arrangement of the analyte concentration values; modifying the graphic to indicate one or more patterns in the analyte data; and displaying, at the mobile computing device, the modified graphic.

In some aspects, the processing further includes: aggregating groups of analyte data; flagging the groups of analyte data based on additional information corresponding to one or more graphical displays; arranging the flagged groups of analyte concentration values; and generating a self-referential dataset from the arranged groups of analyte concentration values.

In one aspect, generating the self-referential dataset further includes one or more of: flagging the analyte data based on one or more high and low thresholds of analyte in a host; flagging the analyte data based on performing statistical analysis of the analyte data; and flagging the analyte data based on contextual data related to when the analyte data was obtained.

In some aspect, contextual data can include: data indicative of one or more physical locations where analyte data was obtained, the relationship between the host and the physical locations, the frequency of visiting the physical locations, meals taken, type and intensity of exercise, type and amount of insulin administered and likelihood of the host being asleep or awake when the analyte data was obtained.

In another aspect, generating a graphic of the arrangement of the analyte concentration values further includes: receiving a user's input including the user's desired graphical display; receiving display configuration data; regenerating the self-referential dataset when the self-referential dataset does not contain data to form the desired graphical display; and reformatting the self-referential dataset based on the user's input and the display configuration data.

In another aspect, modifying the graphic to indicate one or more patterns in the analyte data can include: scanning the self-referential dataset for threshold flags and modifying the graphic based on threshold flags; scanning the self-referential dataset for statistical analysis flags and modifying the graphic based on statistical analysis flags; and scanning the self-referential dataset for analyte contextual data flags and modifying the graphic based on contextual data flags.

In one aspect, modifying the graphic includes introducing or using one or more of: colors, gradients of colors or shades, transparency, opacity, buffer zones, graphical icons, arrows, animations, texts, numbers and gradual fading.

In one aspect, the arrangement includes a spatial-temporal organization of the analyte concentration values in which the analyte concentration values are positioned along a first direction according to a first time scale and along a second direction according to a second time scale, and the analyte level of the analyte concentration values are composed by one or more of a shape, color, shading, or size based on a magnitude of the analyte level.

In one aspect, the first direction and the second direction are linear directions.

In another aspect, the first direction is a curved direction and the second direction is a radial direction.

In one aspect, the first time scale is hourly and the second time scale is daily.

In another aspect, the first time scale is hourly and the second time scale is daily, wherein the modified graphic includes an analyte level trace overlaid over the modified graphic such that higher analyte levels are closer to an outer curved region of the graphic and lower analyte levels are closer to an inner curved region of the graphic, or vice versa.

In one aspect, the higher analyte levels are in a first color, the lower analyte levels are in a second color, and analyte levels between the higher and lower analyte levels are in a third color.

In one aspect, the analyte level trace includes an average analyte level of daily analyte concentration values.

In another aspect, the analyte level trace includes a current analyte level over the hourly time scale.

In some aspects, modifying the graphic can include: a clustering of colors, gradients of colors or shades, lining up of regions, or lighter or darker shades of overlapping regions modifying the arrangement of the analyte concentration values over the plurality of time intervals.

In some aspects, the one or more patterns indicate the analyte concentration values relative to high and low analyte level thresholds of a host.

In one aspect, the plurality of time intervals includes 24 hour periods over 7 days.

In one aspect, the graphic includes an isometric graph plotted over 24 hour periods over 7 days.

In another aspect, the isometric graph is displayable in a three dimensional view.

In one aspect, the graphic includes concentric rings.

In one aspect, the graphic includes a fan-shaped graph.

In another aspect, the graphic includes one or more line graphs.

Another embodiment includes a system, wherein the system includes: a continuous analyte sensor configured to obtain glucose data of a host; a wireless transmitter configured to receive the glucose data from the continuous analyte sensor and transmit the glucose data to a processing module; the processing module further configured to receive insulin data of the host, the glucose data of the host, and event data of the host and to produce a graphical display on a mobile computing device, wherein the processing module further modifies the graphical display to display a visual indicating one or more relationships of the insulin data, the glucose data, the event data with each other or time.

In one aspect, the event data includes one or more of insulin dosing, carbohydrate intake, or exercise.

In one aspect, the insulin data includes an insulin on board value, and the visual includes a colored ring indicating the insulin on board and an estimated time remaining for the insulin on board.

In one aspect, the visual includes a trend graph of the glucose data and an interactive call out window associated with a region or a feature of the trend graph that is presented when a user selects the region or the feature of the trend graph on the graphical display, wherein the presented call-out window includes at least some of the insulin data and/or the event data.

In another aspect, the presented call-out window is configured to display a graphical arrangement of the insulin data including one or more of a bolus or basal amount of insulin, a dosing time of a bolus insulin, a dosing time of basal insulin, or an insulin on board value.

In one aspect, the presented call-out window is configured to display a graphical arrangement of the event data including one or more of an amount of carbohydrate intake, an amount of time spent exercising, an amount of calories burned, or a heart rate level reaching a threshold or time associated thereof.

In one aspect, the visual includes an arrow corresponding with insulin data and a glucose reading including a glucose trend corresponding with glucose data, wherein the arrow is displayed proximate the trend graph and modified to indicate an effect of insulin data on the glucose data.

In some aspects, the visual includes a trend graph of past glucose data and future glucose data, where the future glucose data is determined based on insulin data and action data of the host.

In another aspect, the visual includes: a first graphical display depicting a current value of the glucose data and an indication of a future trend of the glucose data, and a second graphical display representing an amount of insulin, wherein the second graphical display can interact with the first graphical display to depict the likely effect of the amount of insulin on the indication of the future trend of the glucose data.

In one aspect, the processing module is further configured to: generate one or more datasets each based on an action of the host and a prediction of glucose data trend based on the action of the host, and the visual includes a scrollable list including one or more modified graphs each based on the one or more datasets.

In another aspect, the processing module is further configured to: compare a current glucose value to a high and low glucose threshold value and generate a glucose score; compare a current insulin on board to a high and low insulin threshold value and generate an IOB score; generate an insulin state by multiplying the glucose score and the IOB score; and rank the insulin score in one of a plurality of categories.

In one aspect, the plurality of categories includes good, caution and bad.

In one aspect, the visual includes a colored display wherein each plurality of categories is associated with a different color and the color associated with the ranked insulin score is depicted.

In another aspect, generating the insulin state further includes multiplying by a trend value.

In one aspect, generating the insulin state further includes multiplying by one or more scores based on location, food intake, and exercise.

In one aspect, the visual includes a numerical display of current glucose value and a graphic representing a prediction of future trend of glucose values.

In some aspects, the system includes: a look-ahead module configured to receive input data of the host relating to future event data, and the visual includes a glucose trend graph and when modifying the input data, the visual is modified accordingly.

In some aspects, the visual includes a trend graph of the glucose where areas between the trend graph and a high glucose threshold are in a first color and areas between the trend graph and a low threshold are in a second color.

In some aspects of the system, the processing module is configured to produce the graphical display by forming one or more datasets comprising at least some of the insulin data, the glucose data and the event data, flagging or embedding additional information into at least some of the one or more datasets to generate a self-referential dataset, and producing the graphical display in an arrangement that is graphically modified to indicate one or more features in the data.

One embodiment includes a computer-implemented method, including: obtaining, by a glucose monitoring device, glucose data of a host; transmitting, by a wireless transmitter, the glucose data of the host; receiving insulin data of the host, the glucose data of the host, and event data of the host and producing a graphical display on a mobile computing device, wherein the graphical display comprises a display of one or more of the insulin data, the glucose data or the event data; modifying the graphical display to display a visual indicating one or more relationships of the insulin data, the glucose data, or the event data with each other or time, wherein the visual is shaped and configured or scaled to not obscure the display of the insulin data or glucose data or event data and the visual is displayed in its entirety within the display of the insulin data, the glucose data or the event data.

In some aspects, the event data includes one or more of insulin dosing, carbohydrate intake, or exercise.

In one aspect, the insulin data includes an insulin on board value, and the visual includes a colored ring indicating the insulin on board and an estimated time remaining for the insulin on board.

In some aspects, the visual includes a trend graph of the glucose data and an interactive call out window associated with a region or a feature of the trend graph that is presented when a user selects the region or the feature of the trend graph on the graphical display, wherein the presented call-out window includes at least some of the insulin data and/or the event data.

In another aspect, the presented call-out window includes a graphical arrangement of the insulin data including one or more of a bolus or basal amount of insulin, a dosing time of a bolus insulin, a dosing time of basal insulin, or an insulin on board value.

In one aspect, the presented call-out window includes a graphical arrangement of the event data including one or more of an amount of carbohydrate intake, an amount of time spent exercising, an amount of calories burned, or a heart rate level reaching a threshold or time associated thereof.

In some aspects, the visual includes an arrow corresponding with insulin data and a glucose reading including a glucose trend corresponding with glucose data, wherein the arrow is displayed proximate the trend graph and modified to indicate an effect of insulin data on the glucose data.

In one aspect, the visual includes a trend graph of past glucose data and future glucose data, where the future glucose data is determined based on insulin data and action data of the host.

In another aspect, the visual includes: a first graphical display depicting a current value of the glucose data and an indication of a future trend of the glucose data, and a second graphical display representing an amount of insulin, wherein the second graphical display can interact with the first graphical display to depict the likely effect of the amount of insulin on the indication of the future trend of the glucose data.

In some aspects, the method further includes: generating one or more datasets each based on an action of the host and a prediction of glucose data trend based on the action of the host, wherein the visual includes a scrollable list including one or more modified graphs each based on the one or more datasets.

In other aspects, the method further includes: comparing a current glucose value to a high and low glucose threshold value and generate a glucose score; comparing a current insulin on board to a high and low insulin threshold value and generate an IOB score; generating an insulin state by multiplying the glucose score and the IOB score; and ranking the insulin score in one of a plurality of categories.

In one aspect, the plurality of categories includes good, caution and bad.

In another aspect, the visual includes a colored display wherein each plurality of categories is associated with a different color and the color associated with the ranked insulin score is depicted.

In one aspect, generating the insulin state further includes multiplying by a trend value.

In another aspect, generating the insulin state further includes multiplying by one or more scores based on location, food intake, and exercise.

In another aspect, the visual includes a numerical display of current glucose value and a graphic representing a prediction of future trend of glucose values.

In one aspect, the method further includes: receiving input data of the host relating to future event data, wherein the visual includes a glucose trend graph and when modifying the input data, the visual is modified accordingly.

In one aspect, the visual includes a trend graph of the glucose where areas between the trend graph and a high glucose threshold are in a first color and areas between the trend graph and a low threshold are in a second color.

In some aspects of the method, the producing the graphical display includes forming one or more datasets comprising at least some of the insulin data, the glucose data and the event data, flagging or embedding additional information into at least some of the one or more datasets to generate a self-referential dataset, and producing the graphical display in an arrangement that is graphically modified to indicate one or more features in the data.

In one aspect, the processing module is further configured to receive diabetes related data of the host and produce an interactive graphical display on the mobile computing device, wherein a viewer can interact with the interactive graphical display.

In one aspect, the interactive graphic display includes a trend graph of the glucose data with areas between the trend graph and glucose thresholds having different colors for areas exceeding a high threshold and areas exceeding a low threshold, wherein the high threshold and the low threshold are adjustable by the viewer's interaction with the interactive graphical display.

In another aspect, the viewer can interact with the interactive graphical display via a collapsible design layout.

In some aspects, the interactive graphical display further includes one or more animations to convey information.

In another aspect, the viewer can interact with the interactive graphical display by choosing a personalized background image.

In some embodiments, the viewer can interact with the interactive graphical display by entering numerical values via a graphical scroll wheel.

In one aspect, the method further includes: receiving diabetes related data of the host and producing an interactive graphical display on the mobile computing device, wherein a viewer can interact with the interactive graphical display.

In one aspect, the interactive graphic display includes a trend graph of the glucose data with areas between the trend graph and glucose thresholds having different colors for areas exceeding a high threshold and areas exceeding a low threshold, wherein the high threshold and the low threshold are adjustable by the viewer's interaction with the interactive graphical display.

In another aspect, the viewer can interact with the interactive graphical display via a collapsible design layout.

In some aspect, the interactive graphical display further includes one or more animations to convey information.

In one aspect, the viewer can interact with the interactive graphical display by choosing a personalized background image.

In one aspect, the viewer can interact with the interactive graphical display by entering numerical values via a graphical scroll wheel.

In one aspect of the system, the graphical display further includes an indication of the host whose analyte measurements are taken.

One embodiment includes a system, which includes: a continuous analyte sensor configured to obtain analyte measurements of a host; a wireless transmitter configured to receive the analyte measurements from the continuous analyte sensor; and analyte data processing module operable on a mobile computing device in wireless communication with the wireless transmitter, the analyte data processing module configured to: receive at least a portion of the analyte measurements; generate a self-referential dataset based in part on the analyte measurements; generate one or more graphical displays based on the self-referential dataset; modify the self-referential dataset; display one or more modified graphical displays based on the modified self-referential dataset.

In one aspect, the analyte data processing module is further configured to: generate high or low threshold values of analyte concentration in the host based in part on one or more of health data obtained from the host, statistical analysis of the analyte measurements, contextual data related to the analyte measurements, health data derived from a profile of the host, or health data obtained from one or more health data databases; determine a time by which the host's analyte measurements reach the high or low threshold values; modify one or more of the high or low thresholds when the time is equal to or less than a predetermined safety time; regenerate the self-referential dataset to display an animation indicating the change in threshold values.

In one aspect, the modified graphical display includes a graph of analyte measurements versus time and wherein the animation comprises moving a blinking threshold line from a first value to a current analyte value of the host.

In one aspect, one or more of the desired graphical displays include a line graph of analyte measurements versus time and wherein the analyte data processing module is further configured to: determine one or more expected ranges of analyte values; modify the self-referential dataset to display the analyte measurements based on the expected ranges of analyte values.

In some aspect, the expected ranges of analyte values are based on one or more of input from the host, contextual data related to the analyte measurements or health data from health care organizations or healthcare authorities.

In some aspects, the self-referential dataset is modified to use color, line styles, animation, shading, gradient or other visual differentiators to display the analyte measurements in relation to the expected ranges.

In one aspect, the expected ranges of analyte values comprise a target range, a caution range and an outside-target range.

In another aspect, the self-referential dataset is modified to subtract analyte values in target range and only display analyte values in caution and outside-target ranges.

In some aspects, the expected ranges of analyte values are modified based on event data obtained from the host.

In some aspects, one or more of the modified graphical displays include a numerical display of a current value of the analyte measurements, an indication of a prediction of a future trend of analyte measurements, a textual phrase indicating current status and the prediction of the future trend of analyte measurements, a graph of the analyte measurements versus time, one or more lines indicating high and low threshold values of analyte concentration in the host and a graphical representation on the graph of analyte indicating the current value of the analyte measurements.

In one aspect, the self-referential dataset is dynamically modified based on analyte measurements and the self-referential dataset is further modified to indicate current analyte measurement values reaching or exceeding a threshold of the analyte concentration values in the host and wherein the indication of the prediction of the future trend of analyte measurements, the threshold line associated with the threshold being reached or exceeded and the graphical representation of the current analyte value on the analyte graph change style and pulsate in unison.

In another aspect, the analyte data processing module is further configured to generate one or more audible alarms when an analyte threshold value is reached or exceeded.

In one aspect, the self-referential dataset is modified to display one or more system status messages.

In another aspect, the self-referential dataset is modified to display a dark background.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

Figure 1A:
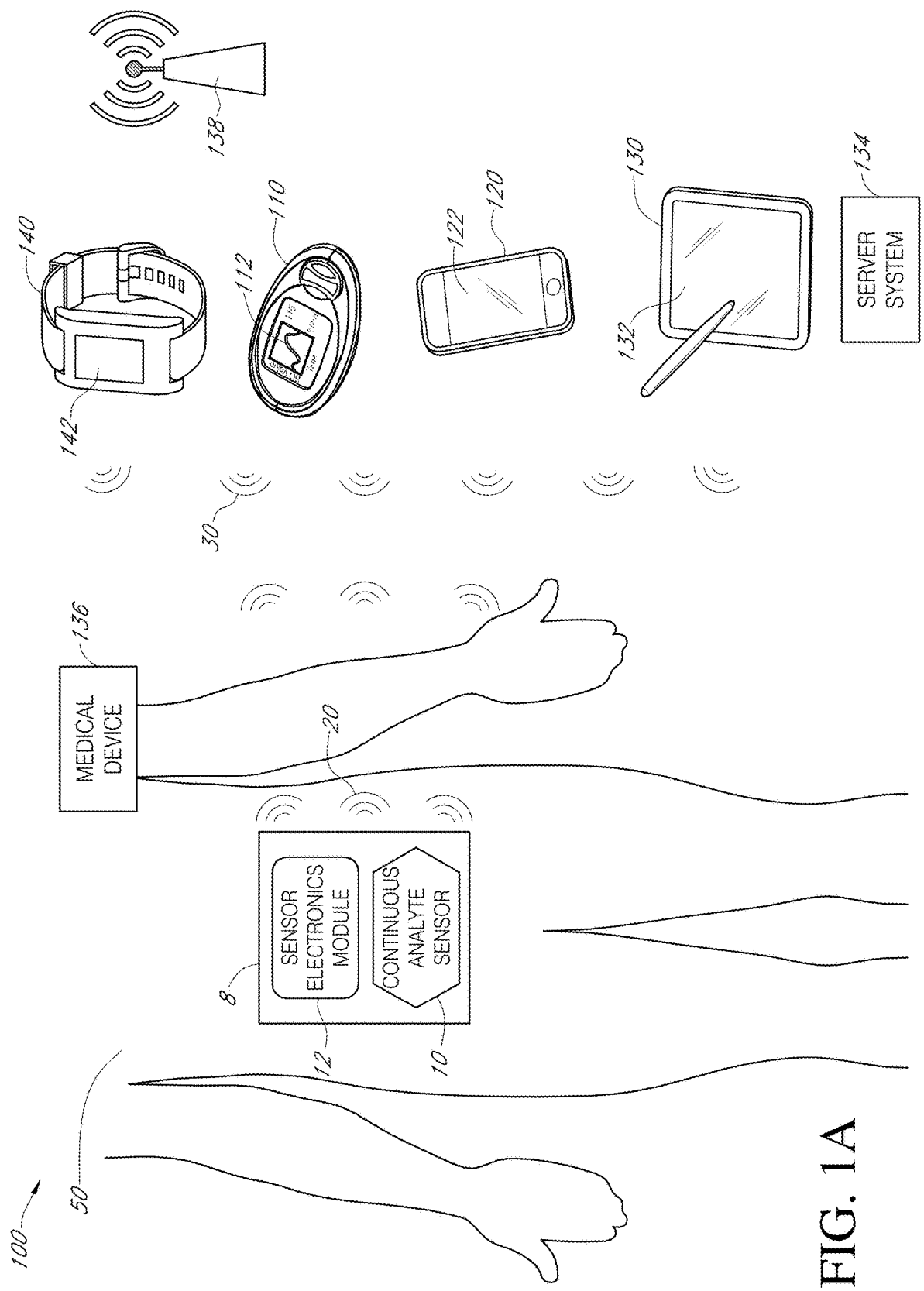
FIG. 1A illustrates aspects of an example system that may be used in connection with implementing embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

Embodiments of the present disclosure are directed to systems, methods, and devices for generating dynamic data structures and graphical displays. In various deployments described herein, the analyte data is glucose data generated by an analyte sensor system configured to connect to display devices and the like. Implementing aspects of the present disclosure, as described in detail herein, may modify graphical displays of analyte data in a manner to conveniently and efficiently indicate patterns in the analyte data. Moreover, implementing aspects of the present disclosure may also conveniently indicate one or more relationships between the glucose data, insulin data and actions of the user. In particular, such aspects of the disclosure relate to, for example, generating a self-referential data structure and modifying graphical displays based on that data structure to convey information related to management of diabetes.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

Overview

In some embodiments, a system is provided for continuous measurement of an analyte in a host. The system may include: a continuous analyte sensor configured to continuously measure a concentration of the analyte in the host, and a sensor electronics module physically connected to the continuous analyte sensor during sensor use. In certain embodiments, the sensor electronics module includes electronics configured to process a data stream associated with an analyte concentration measured by the continuous analyte sensor, in order to generate sensor information that includes raw sensor data, transformed sensor data, and/or any other sensor data, for example. The sensor electronics module may further be configured to generate sensor information that is customized for respective display devices, such that different display devices may receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, and/or reaction products. In some implementations, the analyte for measurement by the methods or devices is glucose. However, other analytes are contemplated as well, including but not limited to: acarboxyprothrombin; acetoacetic acid; acetone; Acetyl CoA; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; ketone bodies; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, isoprene (2-methyl-1,3-butadiene), *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, Wuchereria bancrofti, Flavivirus (for example deer tick, dengue fever, Powassan, West Nile, yellow fever, or Zika virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain implementations. The analyte can be naturally present in the biological fluid, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon, ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA), and intermediaries in the Citric Acid Cycle.

Alerts

In certain embodiments, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In certain embodiments, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In certain embodiments, the sensor electronics module merely provides a data field indicating that an alarm conditions exists and the display device, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one example embodiment, the sensor electronics module is configured to search for and attempt to alarm a host or care provider sequentially using a list of display devices, such as: (1) a default display device or a custom analyte monitoring device; (2) a mobile phone via auditory and/or visual methods, such as, text message to the host and/or care provider, voice message to the host and/or care provider, and/or 911); (3) a tablet; (4) a smart watch or bracelet; and/or (5) smart glasses or other wearable display device.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may include software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, tablets, PDAs, PCs and the like).

In some embodiments, certain display devices may be in direct wireless communication with the sensor electronics module, but intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices include built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. This may be referred to in some cases as two-way authentication.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how sensor information is obtained.

In some embodiments, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, searchable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device (which may also be referred to as an analyte display device), a mobile phone, a tablet, a smart watch, a reference analyte monitor, a drug delivery device, a medical device and a personal computer) may be configured to wirelessly communicate with the sensor electronics module. The plurality of display devices may be configured to display at least some of the displayable sensor information wirelessly communicated from the sensor electronics module. The displayable sensor information may include sensor data, such as raw data and/or transformed sensor data, such as analyte concentration values, rate of change information, trend information, alert information, sensor diagnostic information and/or calibration information, for example.

Analyte Sensor

With reference to FIG. 1A, in some embodiments, analyte sensor 10 includes a continuous analyte sensor, for example, a subcutaneous, transdermal (e.g., transcutaneous), or intravascular device. In some embodiments, such a sensor or device can analyze a plurality of intermittent blood samples. While the present disclosure includes embodiments of glucose sensors, such embodiments may be used for other analytes as well. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of glucose and providing an output signal that represents the concentration of glucose (e.g., as a form of analyte data).

In certain embodiments, analyte sensor 10 is an implantable glucose sensor, such as described with reference to U.S. Pat. No. 6,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 6,565,509 to Say et al., for example. In embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Figure 2A:
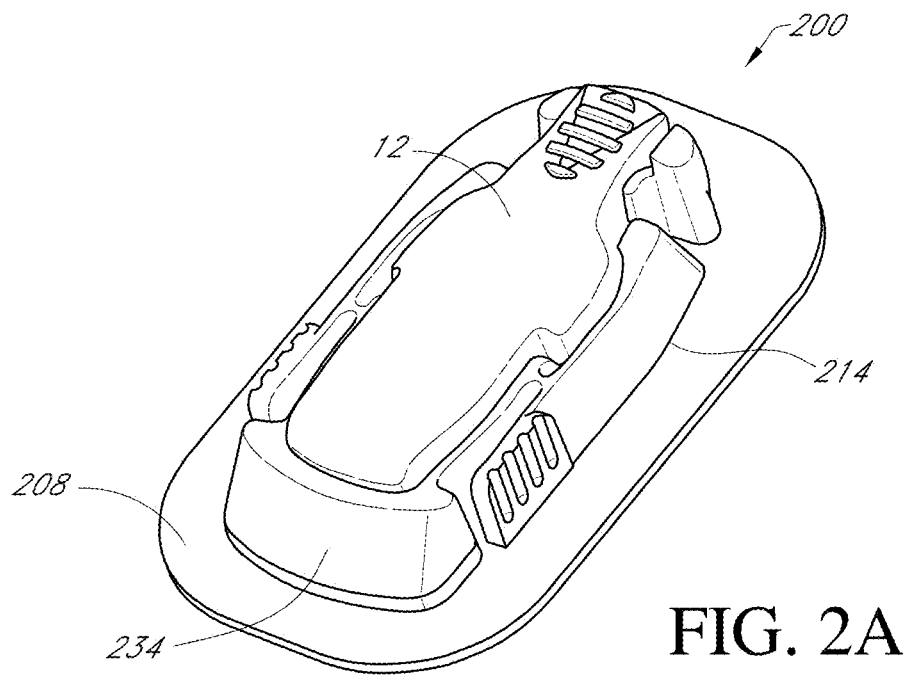
FIG. 2A is a perspective view of an example enclosure that may be used in connection with implementing embodiments of an analyte sensor system.
Figure 2B:
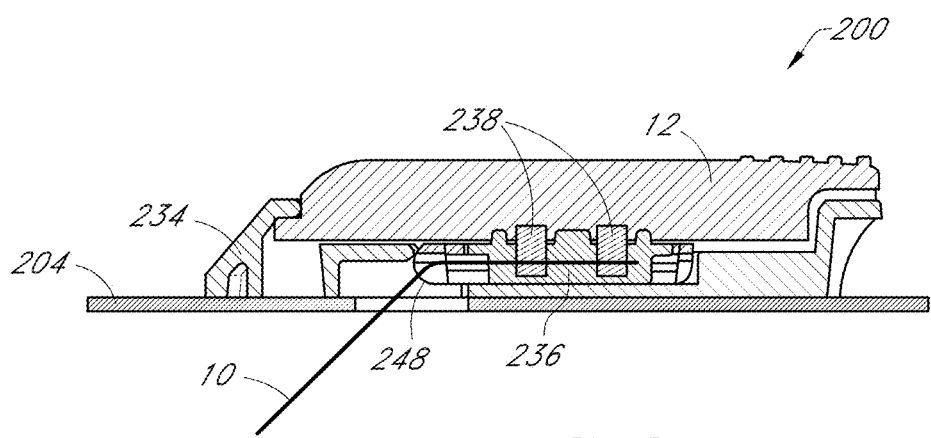
FIG. 2B is a side view of an example enclosure that may be used in connection with implementing embodiments of an analyte sensor system.

FIGS. 2A and 2B are perspective and side views of enclosure 200 that may be used in connection with implementing embodiments of analyte sensor system 8, according to certain aspects of the present disclosure. Enclosure 200 includes mounting unit 214 and sensor electronics module 12 attached thereto in certain embodiments. Enclosure 200 is shown in a functional position, including mounting unit 214 and sensor electronics module 12 matingly engaged therein. In some embodiments, mounting unit 214, also referred to as a housing or sensor pod, includes base 234 adapted for fastening to a host's or user's skin. Base 234 can be formed from a variety of hard or soft materials, and can include a low profile for minimizing protrusion of the device from the host during use. In some embodiments, base 234 is formed at least partially from a flexible material, which may provide numerous advantages over other transcutaneous sensors, which, unfortunately, can suffer from motion-related artifacts associated with the host's movement when the host is using the device. Mounting unit 214 and/or sensor electronics module 12 can be located over the sensor insertion site to protect the site and/or provide a minimal footprint (utilization of surface area of the host's skin).

In some embodiments, a detachable connection between mounting unit 214 and sensor electronics module 12 is provided, which enables improved manufacturability, namely, the potentially relatively inexpensive mounting unit 214 can be disposed of when refurbishing or maintaining analyte sensor system 8, while the relatively more expensive sensor electronics module 12 can be reusable with multiple sensor systems. In some embodiments, sensor electronics module 12 is configured with signal processing (programming), for example, configured to filter, calibrate, and/or execute other algorithms useful for calibration and/or display of sensor information. However, an integral (non-detachable) sensor electronics module can be configured.

In some embodiments, contacts 238 are mounted on or in a subassembly hereinafter referred to as contact subassembly 236 configured to fit within base 234 of mounting unit 214 and hinge 248 that allows contact subassembly 236 to pivot between a first position (for insertion) and a second position (for use) relative to mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, contacts 238 are formed from a conductive elastomeric material, such as a carbon black elastomer, through which sensor 10 extends.

With further reference to FIGS. 2A and 2B, in certain embodiments, mounting unit 214 is provided with adhesive pad 208, disposed on the mounting unit's back surface and includes a releasable backing layer. Thus, removing the backing layer and pressing at last a portion of base 234 of mounting unit 214 onto the host's skin adheres mounting unit 214 to the host's skin. Additionally or alternatively, an adhesive pad can be placed over some or all of analyte sensor system 8 and/or sensor 10 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety for all purposes.

Example Configurations

Referring again to FIG. 1A, system 100 that may be used in connection with implementing aspects of an analyte sensor system is depicted. In some cases, system 100 may be used to implement various systems described herein. System 100 in embodiments includes analyte sensor system 8 and display devices 110, 120, 130, and 140, according to certain aspects of the present disclosure. Analyte sensor system 8 in the illustrated embodiment includes sensor electronics module 12 and continuous analyte sensor 10 associated with the sensor electronics module 12. Sensor electronics module 12 may be in wireless communication (e.g., directly or indirectly) with one or more of display devices 110, 120, 130, and 140. In embodiments, system 100 also includes medical device 136 and server system 134. Sensor electronics module 12 may also be in wireless communication (e.g., directly or indirectly) with medical device 136 and server system 134. In some examples, display devices 110-140 may also be in wireless communication with the server system 134 and/or the medical device 136.

In certain embodiments, sensor electronics module 12 includes electronic circuitry associated with measuring and processing the continuous analyte sensor data, including prospective algorithms associated with processing and calibration of the sensor data. Sensor electronics module 12 can be physically connected to continuous analyte sensor 10 and can be integral with (non-releasably attached to) or releasably attachable to continuous analyte sensor 10. Sensor electronics module 12 may include hardware, firmware, and/or software that enables measurement of levels of the analyte via a glucose sensor. For example, sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor.

Sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1A, display devices 110, 120, 130, and/or 140 are configured for displaying (and/or alarming) the displayable sensor information that may be transmitted by sensor electronics module 12 (e.g., in a customized data package that is transmitted to the display devices based on their respective preferences). Each of display devices 110, 120, 130, or 140 can include a display such as a touchscreen display 112, 122, 132, /or 142 for displaying sensor information and/or analyte data to a user and/or receiving inputs from the user. For example, a graphical user interface may be presented to the user for such purposes. In some embodiments, the display devices may include other types of user interfaces such as voice user interface instead of or in addition to a touchscreen display for communicating sensor information to the user of the display device and/or receiving user inputs. In some embodiments, one, some, or all of the display devices is configured to display or otherwise communicate the sensor information as it is communicated from the sensor electronics module (e.g., in a data package that is transmitted to respective display devices), without any additional prospective processing required for calibration and real-time display of the sensor data.

Figure 1B:
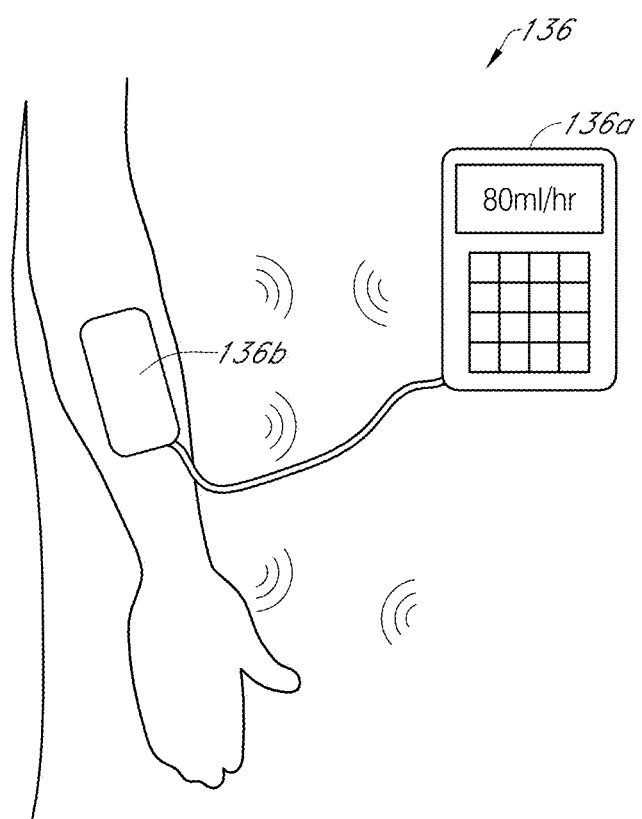
FIG. 1B illustrates aspects of an example system that may be used in connection with implementing embodiments of the disclosure.

Medical device 136 may be a passive device in example embodiments of the disclosure. For example, medical device 136 may be an insulin pump for administering insulin to a user, as shown in FIG. 1B. For a variety of reasons, it may be desirable for such an insulin pump to receive and track glucose values transmitted from analyte sensor system 8. One reason is to provide the insulin pump a capability to suspend or activate insulin administration when a glucose value falls below a threshold value. One solution that allows a passive device (e.g., medical device 136) to receive analyte data (e.g., glucose values) without being bonded to analyte sensor system 8 is to include the analyte data in the advertisement messages transmitted from analyte sensor system 8. The data included in the advertisement messages can be encoded so that only a device that has the identification information associated with analyte sensor system 8 can decode the analyte data. In some embodiments, the medical device 136 includes a sensor apparatus 136b, e.g., attachable or wearable by the user, in wired or wireless communication with a dedicated monitor or display apparatus 136a to process sensor data and/or display data from the sensor apparatus 136a and/or receive input for operation of the sensor apparatus and/or data processing.

With further reference to FIG. 1A, the plurality of display devices may include a custom display device specially designed for displaying certain types of displayable sensor information associated with analyte data received from sensor electronics module 12 (e.g., a numerical value and an arrow, in some embodiments). Analyte display device 110 is an example of such a custom device. In some embodiments, one of the plurality of display devices is smartphone, such as mobile phone 120 based on an Android, iOS or other operating system, and configured to display a graphical representation of the continuous sensor data (e.g., including current and historic data). Other display devices can include other hand-held devices, such as tablet 130, smart watch 140, medical device 136 (e.g., an insulin delivery device or a blood glucose meter), and/or a desktop or laptop computer.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1A, a plurality of different display devices can be in direct wireless communication with a sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

As further illustrated in FIG. 1A, system 100 may also include wireless access point (WAP) 138 that may be used to couple one or more of analyte sensor system 8, the plurality display devices, server system 134, and medical device 136 to one another. For example, WAP 138 may provide Wi-Fi and/or cellular connectivity within system 100. Near Field Communication (NFC) may also be used among devices of system 100. Server system 134 may be used to collect analyte data from analyte sensor system 8 and/or the plurality of display devices, for example, to perform analytics thereon, generate universal or individualized models for glucose levels and profiles, and so on.

Figure 3A:
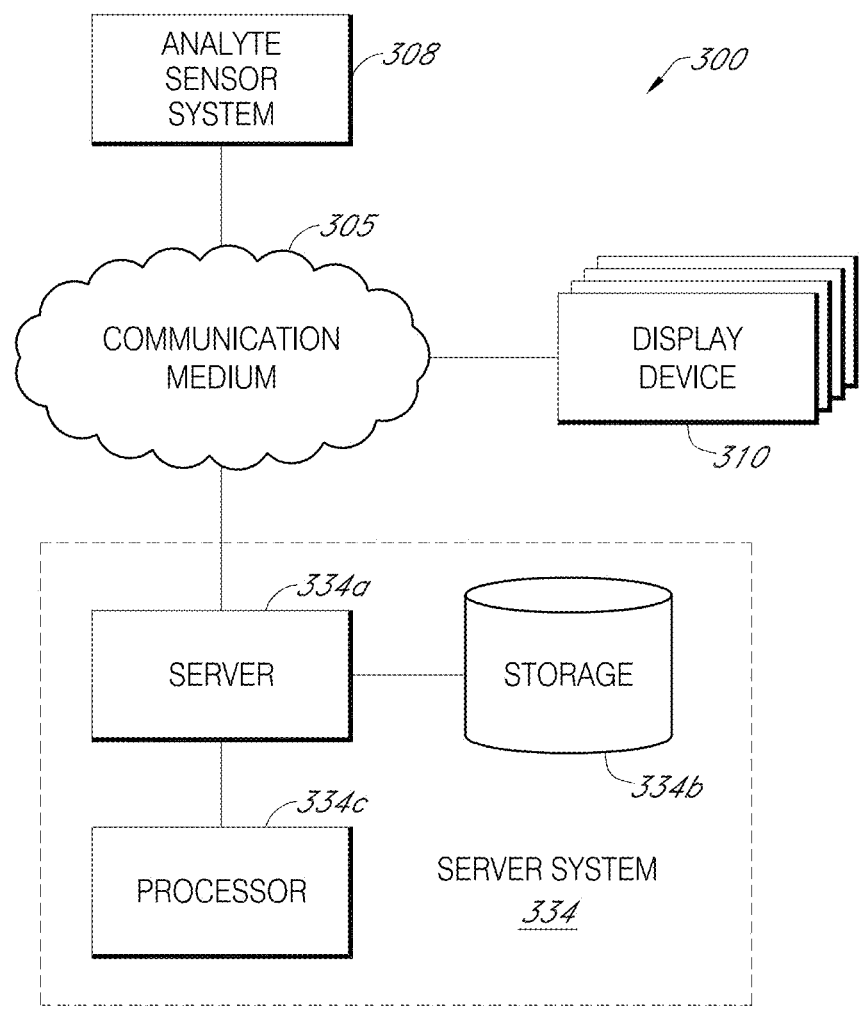
FIG. 3A illustrates aspects of an example system that may be used in connection with implementing embodiments of the disclosure.

Referring now to FIG. 3A, system 300 is depicted. System 300 may be used in connection with implementing embodiments of the disclosed systems, methods, and devices. By way of example, the various below-described components of FIG. 3A may be used to provide wireless communication of glucose data, for example between an analyte sensor system and a plurality of display devices, medical devices, servers and so on, such as those shown in FIG. 1A.

As shown in FIG. 3A, system 300 may include analyte sensor system 308 and one or more display devices 310. Additionally, in the illustrated embodiment, system 300 includes server system 334, which in turn includes server 334a coupled to processor 334c and storage 334b. Analyte sensor system 308 may be coupled to display devices 310 and/or server system 334 via communication medium 305.

As will be described in detail herein, analyte sensor system 308 and display devices 310 may exchange messaging via communication medium 305, and communication medium 305 may also be used to deliver analyte data to display devices 310 and/or server system 334. As alluded to above, display devices 310 may include a variety of electronic computing devices, such as, for example, a smartphone, tablet, laptop, wearable device, etc. Display devices 310 may also include analyte display device 110 and medical device 136. Here, it will be noted that a GUI of display device 310 may perform such functions as accepting user input and displaying menus as well as information derived from analyte data. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, communication medium 305 may be based on one or more wireless communication protocols such as Bluetooth, Bluetooth Low Energy (BLE), ZigBee, Wi-Fi, 802.11 protocols, Infrared (IR), Radio Frequency (RF), 2G, 3G, 4G, etc., and/or wired protocols and media.

In various embodiments, the elements of system 300 may be used to perform various processes described herein and/or may be used to execute various operations described herein with regard to one or more disclosed systems and methods. Upon studying the present disclosure, one of skill in the art will appreciate that system 300 may include multiple analyte sensor systems, communication media 305, and/or server systems 334.

As mentioned, communication medium 305 may be used to connect or communicatively couple analyte sensor system 308, display devices 310, and/or server system 334 to one another or to a network, and communication medium 305 may be implemented in a variety of forms. For example, communication medium 305 may include an Internet connection, such as a local area network (LAN), a wide area network (WAN), a fiber optic network, internet over power lines, a hard-wired connection (e.g., a bus), and the like, or any other kind of network connection. Communication medium 305 may be implemented using any combination of routers, cables, modems, switches, fiber optics, wires, radio (e.g., microwave/RF links), and the like. Further, communication medium 305 may be implemented using various wireless standards, such as Bluetooth®, BLE, Wi-Fi, 3GPP standards (e.g., 2G GSM/GPRS/EDGE, 3G UMTS/CDMA2000, or 4G LTE/LTE-U), etc. Upon reading the present disclosure, one of skill in the art will recognize other ways to implement communication medium 305 for communications purposes.

Server 334a may receive, collect, or monitor information, including analyte data and related information, from analyte sensor system 308 and/or display device 310, such as input responsive to the analyte data or input received in connection with an analyte monitoring application running on analyte sensor system or display device 310. In such cases, server 334a may be configured to receive such information via communication medium 305. This information may be stored in storage 334b and may be processed by processor 334c. For example, processor 334c may include an analytics engine capable of performing analytics on information that server 334a has collected, received, etc. via communication medium 305. In embodiments, server 334a, storage 334b, and/or processor 334c may be implemented as a distributed computing network, such as a Hadoop® network, or as a relational database or the like.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In embodiments, server 334a at least partially directs communications made over communication medium 305. Such communications include the delivery and/or messaging (e.g., advertisement, command, or other messaging) and analyte data. For example, server 334a may process and exchange messages between analyte sensor system 308 and display devices 310 related to frequency bands, timing of transmissions, security, alarms, and so on. Server 334a may update information stored on analyte sensor system 308 and/or display devices 310, for example, by delivering applications thereto. Server 334a may send/receive information to/from analyte sensor system 308 and/or display devices 310 in real time or sporadically. Further, server 334a may implement cloud computing capabilities for analyte sensor system 308 and/or display devices 310.

Figure 3B:
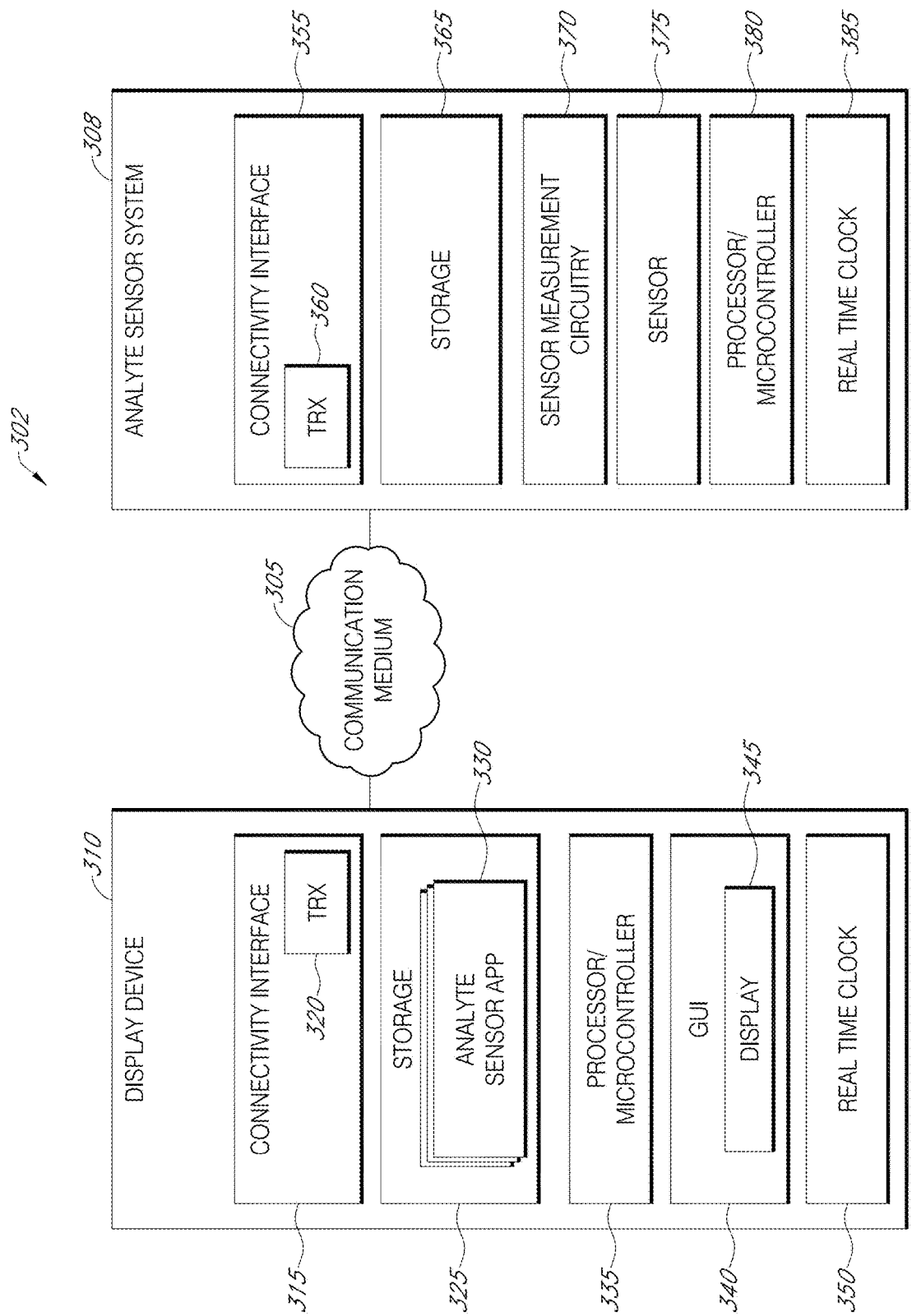
FIG. 3B illustrates aspects of an example system that may be used in connection with implementing embodiments of the disclosure.

FIG. 3B depicts system 302, which includes examples of additional aspects of the present disclosure that may be used in connection implementing an analyte sensor system. As illustrated, system 302 may include analyte sensor system 308. As shown, analyte sensor system 308 may include analyte sensor 375 (e.g., which may also be designated with the numeral 10 in FIG. 1A) coupled to sensor measurement circuitry 370 for processing and managing sensor data. Sensor measurement circuitry 370 may be coupled to processor/microprocessor 380 (e.g., which may be part of item 12 in FIG. 1A). In some embodiments, processor 380 may perform part or all of the functions of the sensor measurement circuitry 370 for obtaining and processing sensor measurement values from sensor 375. Processor 380 may be further coupled to a radio unit or transceiver 320 (e.g., which may be part of item 12 in FIG. 1A) for sending sensor data and receiving requests and commands from an external device, such as display device 310, which may be used to display or otherwise provide the sensor data (or analyte data) to a user. As used herein, the terms "radio unit" and "transceiver" are used interchangeably and generally refer to a device that can wirelessly transmit and receive data. Analyte sensor system 308 may further include storage 365 (e.g., which may be part of item 12 in FIG. 1A) and real-time clock (RTC) 380 (e.g., which may be part of item 12 in FIG. 1A) for storing and tracking sensor data.

As alluded to above, wireless communication protocols may be used to transmit and receive data between analyte sensor system 308 and the display device 310 via communication medium 305. Such wireless protocols may be designed for use in a wireless network that is optimized for periodic and small data transmissions (that may be transmitted at low rates if necessary) to and from multiple devices in a close range (e.g., a personal area network (PAN)). For example, one such protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing overhead) to reduce power consumption. In some embodiments, burst broadcasting schemes (e.g., one-way communication) may be used. This may eliminate overhead required for acknowledgement signals and allow for periodic transmissions that consume little power.

The protocols may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as Wi-Fi, Bluetooth and Bluetooth Low Energy (BLE). The wireless protocol may operate in various frequency bands such as an open ISM band such as 2.4 GHz. Furthermore, to reduce power usage, the wireless protocol may adaptively configure data rates according to power consumption.

With further reference to FIG. 3B, system 302 may include display device 310 communicatively coupled to analyte sensor system 308 via communication medium 305. In the illustrated embodiment, display device 310 includes connectivity interface 315 (which in turn includes transceiver 320), storage 325 (which in turn stores analyte sensor application 330 and/or additional applications), processor/microprocessor 335, graphical user interface (GUI) 340 that may be presented using display 345 of display device 310, and real-time clock (RTC) 350. A bus (not shown here) may be used to interconnect the various elements of display device 310 and transfer data between these elements.

Display device 310 may be used for alerting and providing sensor information or analyte data to a user, and may include a processor/microprocessor 335 for processing and managing sensor data. Display device 310 may include display 345, storage 325, analyte sensor application 330, and real-time clock 350 for displaying, storing, and tracking sensor data. Display device 310 may further include a radio unit or transceiver 320 coupled to other elements of display device 310 via connectivity interface 315 and/or a bus. Transceiver 320 may be used for receiving sensor data and for sending requests, instructions, and/or data to analyte sensor system 308. Transceiver 320 may further employ a communication protocol. Storage 325 may also be used for storing an operating system for display device 310 and/or a custom (e.g., proprietary) application designed for wireless data communication between a transceiver and display device 310. Storage 325 may be a single memory device or multiple memory devices and may be a volatile or non-volatile memory for storing data and/or instructions for software programs and applications. The instructions may be executed by processor 335 to control and manage transceiver 320.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processor 335, 380 does not need to manage these activities, but rather provides desired data values for transmission, and manages high level functions such as power up or down, set a rate at which messages are transmitted, and the like. Instructions and data values for performing these high-level functions can be provided to the transceiver circuits via a data bus and transfer protocol established by the manufacturer of the transceiver 320, 360.

Components of analyte sensor system 308 may require replacement periodically. For example, analyte sensor system 308 may include an implantable sensor 375 that may be attached to a sensor electronics module that includes sensor measurement circuitry 370, processor 380, storage 365, and transceiver 360, and a battery (not shown). Sensor 375 may require periodic replacement (e.g., every 7 to 30 days). The sensor electronics module may be configured to be powered and active for much longer than sensor 375 (e.g., for three to six months or more) until the battery needs replacement. Replacing these components may be difficult and require the assistance of trained personnel. Reducing the need to replace such components, particularly the battery, significantly improves the convenience and cost of using analyte sensor system 308, including to the user. In some embodiments, when a sensor electronic module is used for the first time (or reactivated once a battery has been replaced in some cases), it may be connected to sensor 375 and a sensor session may be established. As will be further described below, there may be a process for initially establishing communication between display device 310 and the sensor electronics module when the module is first used or re-activated (e.g., the battery is replaced). Once display device 310 and sensor electronics module have established communication, display device 310 and the sensor electronics module may periodically and/or continuously be in communication over the life of several sensors 375 until, for example, the battery needs to be replaced. Each time sensor 375 is replaced, a new sensor session may be established. The new sensor session may be initiated through a process completed using display device 310 and the process may be triggered by notifications of a new sensor via the communication between the sensor electronics module and display device 310 that may be persistent across sensor sessions.

Analyte sensor system 308 typically gathers analyte data from sensor 375 and transmits the same to display device 310. Data points regarding analyte values may be gathered and transmitted over the life of sensor 375 (e.g., in the range of 1 to 30 days or more). New measurements may be transmitted often enough to adequately monitor glucose levels. Rather than having the transmission and receiving circuitry of each of analyte sensor system 308 and display device 310 continuously communicating, analyte sensor system 308 and display device 310 may regularly and/or periodically establish a communication channel between them. Thus, analyte sensor system 308 can in some cases communicate via wireless transmission with display device 310 (e.g., a hand-held computing device, medical device, or proprietary device) at predetermined time intervals. The duration of the predetermined time interval can be selected to be long enough so that analyte sensor system 308 does not consume too much power by transmitting data more frequently than needed, yet frequent enough to provide substantially real-time sensor information (e.g., measured glucose values or analyte data) to display device 310 for output (e.g., via display 345) to a user. While the predetermined time interval is every five minutes in some embodiments, it is appreciated that this time interval can be varied to be any desired length of time.

With continued reference to FIG. 3B, as shown, connectivity interface 315 interfaces display device 310 to communication medium 305, such that display device 310 may be communicatively coupled to analyte sensor system 308 via communication medium 305. Transceiver 320 of connectivity interface 315 may include multiple transceiver modules operable on different wireless standards. Transceiver 320 may be used to receive analyte data and associated commands and messages from analyte sensor system 308. Additionally, connectivity interface 315 may in some cases include additional components for controlling radio and/or wired connections, such as baseband and/or Ethernet modems, audio/video codecs, and so on.

Storage 325 may include volatile memory (e.g. RAM) and/or non-volatile memory (e.g. flash storage), may include any of EPROM, EEPROM, cache, or may include some combination/variation thereof. In various embodiments, storage 325 may store user input data and/or other data collected by display device 310 (e.g., input from other users gathered via analyte sensor application 330). Storage 325 may also be used to store volumes of analyte data received from analyte sensor system 308 for later retrieval and use, e.g., for determining trends and triggering alerts. Additionally, storage 325 may store analyte sensor application 330 that, when executed using processor 335, for example, receives input (e.g., by a conventional hard/soft key or a touch screen, voice detection, or other input mechanism), and allows a user to interact with the analyte data and related content via GUI 340, as will be described in further detail herein.

In various embodiments, a user may interact with analyte sensor application 330 via GUI 340, which may be provided by display 345 of display device 310. By way of example, display 345 may be a touchscreen display that accepts various hand gestures as inputs. Application 330 may process and/or present analyte-related data received by display device 310, according to various operations described herein, and present such data via display 345. Additionally, application 330 may be used to obtain, access, display, control, and/or interface with analyte data and related messaging and processes associated with analyte sensor system 308, as is described in further detail herein.

Application 330 may be downloaded, installed, and initially configured/setup on display device 310. For example, display device 310 may obtain application 330 from server system 334, or from another source accessed via a communication medium (e.g., communication medium 305), such as an application store or the like. Following installation and setup, application 330 may be used to access and/or interface with analyte data (e.g., whether stored on server system 334, locally from storage 325, or from analyte sensor system 308). By way of illustration, application 330 may present a menu that includes various controls or commands that may be executed in connection with the operating of analyte sensor system 308 and one or more display devices 310. Application 330 may also be used to interface with or control other display devices 310, for example, to deliver or make available thereto analyte data, including for example by receiving/sending analyte data directly to the other display device 310 and/or by sending an instruction for analyte sensor system 308 and the other display device 310 to be connected, etc., as will be described herein. In some implementations, application 330 may interact with other application(s) of the display device to retrieve or provide relevant data, e.g., such as other health data.

Analyte sensor application 330 may include various code/functional modules, such as, for example, a display module, a menu module, a list module, and so on as will become clear in light of the description of various functionalities herein (e.g., in connection with disclosed methods). These modules may be implemented separately or in combination. Each module may include computer-readable media and have computer-executable code stored thereon, such that the code may be operatively coupled to and/or executed by processor 335 (which, e.g., may include a circuitry for such execution) to perform specific functions (e.g., as described herein with regard to various operations and flow charts etc.) with respect to interfacing with analyte data and performing tasks related thereto. As will be further described below, a display module may present (e.g., via display 345) various screens to a user, with the screens containing graphical representations of information provided by application 330. In further embodiments, application 330 may be used to display to the user an environment for viewing and interacting with various display devices that may be connectable to analyte sensor system 308, as well as with analyte sensor system 308 itself. Sensor application 330 may include a native application modified with a software design kit (e.g., depending on the operating system) in order to carry out the functionalities/features described herein.

Referring again to FIG. 3B, display device 310 also includes processor 335. Processor 335 may include processor sub-modules, including, by way of example, an applications processor that interfaces with and/or controls other elements of display device 310 (e.g., connectivity interface 315, application 330, GUI 340, display 345, RTC 350, etc.). Processor 335 may include a controller and/or microcontroller that provides various controls (e.g., interfaces with buttons and switches) related to device management, such as, for example, lists of available or previously paired devices, information related to measurement values, information related to network conditions (e.g., link quality and the like), information related to the timing, type, and/or structure of messaging exchanged between analyte sensor system 308 and display device 310, and so on. Additionally, the controller may include various controls related to the gathering of user input, such as, for example, a user's finger print (e.g., to authorize the user's access to data or to be used for authorization/encryption of data, including analyte data), as well as analyte data.

Processor 335 may include circuitry such as logic circuits, memory, a battery and power circuitry, and other circuitry drivers for periphery components and audio components. Processor 335 and any sub-processors thereof may include logic circuits for receiving, processing, and/or storing data received and/or input to display device 310, and data to be transmitted or delivered by display device 310. Processor 335 may be coupled by a bus to display 345 as well as connectivity interface 315 and storage 325 (including application 330). Hence, processor 335 may receive and process electrical signals generated by these respective elements and thus perform various functions. By way of example, processor 335 may access stored content from storage 325 at the direction of application 330, and process the stored content for display and/or output by display 345. Additionally, processor 335 may process the stored content for transmission via connectivity interface 315 and communication medium 305 to other display devices 310, analyte sensor system 308, or server system 334. Display device 310 may include other peripheral components not shown in detail in FIG. 3B.

In further embodiments, processor 335 may further obtain, detect, calculate, and/or store data input by a user via display 345 or GUI 340, or data received from analyte sensor system 308 (e.g., analyte sensor data or related messaging), over a period of time. Processor 335 may use this input to gauge the user's physical and/or mental response to the data and/or other factors (e.g., time of day, location, etc.). In various embodiments, the user's response or other factors may indicate preferences with respect to the use of certain display devices 310 under certain conditions, and/or the use of certain connection/transmission schemes under various conditions, as will be described in further detail herein.

It should be noted at this juncture that like-named elements as between display device 310 and analyte sensor system 308 may include similar features, structures, and/or capabilities. Therefore, with respect to such elements, the description of display device 310 above may in some cases be applied to analyte sensor system 308.

In some aspects in accordance with the systems, devices and methods of the present disclosure, health related and non-health related data are aggregated, structured, and/or transformed for intelligently producing outputs including new analytical data constructions, displays, and controls of the system's devices and devices of other systems. Such health-related information can include glucose and related data (for example, insulin, meal, activity, etc.), and non-health related data can include location data, user demographic data, etc. Implementations in accordance with such aspects of the present technology are perceived to improve the operation of the system, for example, by reducing complexities in data processing and data transmissions between devices, reducing the amount of data and processing algorithms to be stored and operated, and thereby speeding up the performance of the systems as described herein. Moreover, implementations in accordance with such aspects of the present technology are envisioned to improve the ability of users to manage their diabetes or other disorders with continuous analyte monitoring. Examples are disclosed below of techniques and tools for producing such outputs pertaining to glucose state, trend, history, context, and insights to help the user make well-informed decisions in managing their diabetes. Yet, the disclosed techniques, systems, devices and tools can be applied for other health maladies.

In managing diabetes, more and more, diabetic users of CGM systems want to see more glucose data over time within the context of their lives, such as how their glucose levels fluctuated during their eating habits (generally, and specific to particular meals), their lifestyle (for example, during work day and time at home or play), physical activities, etc. Yet, display screens are limited in size, resolution, and other technical parameters. Moreover, even with larger display screens, cramming more data on a screen does not always improve the effectiveness of the data display or aid the understanding of the user viewing the data presented on the screen. To address such limitations in CGM systems, data display should be intelligently designed and constructed to avoid information overload and clutter that leads to misunderstanding of data, confusion, missed information, etc. or worse, poor decisions. For example, poor data display can ultimately lead to poor decisions by the user, which may consequently be detrimental to their glucose management and health.

Moreover, while more contextual, meaningful data is being demanded, manufacturers of CGM systems must be mindful of regulations and standards set forth by regulatory bodies, for example, the Federal Drug Administration (FDA). In some cases, the data displayed within an "actionable time period," such as within 3 hours of real-time, may be subject to certain restrictions or requirements, which can affect the classification of a CGM device and related software apps. These regulations and restrictions also affect the cost of their target products, software or services.

The users of the CGM devices and related software, demand more meaningful displays and graphics, which can present their health-related data efficiently and intelligently to enable safe and wise decision making for managing their glucose and health. Data visualization techniques and modified graphics as described herein can be used to intelligently present information about a user's glucose state, trend, history and corresponding context, thereby overcoming technical challenges and situational challenges (for example, legal or regulatory) and provide the end-user with benefits, both directly (such as providing decision support) and indirectly (such as saving the user time in their daily lives while they manage their diabetes).

Glucose Pattern Visualization

As discussed above, the analyte data as collected by the analyte sensor system 308 may include raw sensor data. Unmodified graphical representation of raw sensor data to a user may be of little value as the user can potentially miss important information buried in the clutter of voluminous or unmodified raw sensor data. Consequently, the embodiments described herein include systems and methods to build data structures or arrangements of analyte data whose features facilitate display of analyte data in a modified graphical representation to conveniently indicate patterns and/or information valuable to a user's health.

In some embodiments, the analyte sensor system 308 can generate one or more datasets of analyte data corresponding to analyte measurements over one or more intervals of time. For example, in some embodiments, the analyte sensor system 308 can generate a dataset corresponding to measurements of analyte every 5 minutes. Other time intervals are possible. The analyte sensor system 308 can produce an analyte concentration value for each analyte dataset. The display device 310 can receive the raw analyte concentration values and generate data structures or arrangements of analyte data, which can in turn produce modifiable graphical displays. The modifiable graphical displays can efficiently be adjusted to alter one or more features that can conveniently indicate patterns or other valuable health information to a viewer.

In some example implementations, the analyte sensor system 308 or the display device 310 processes the datasets to produce a graphical display displayable on the display device 310, where the graphical display comprises an arrangement of the analyte concentration values over multiple time intervals that is graphically modified, e.g., to indicate one or more patterns in the analyte data. In some examples, the arrangement of the analyte concentration values for the graphical display includes a spatial-temporal organization of the analyte concentration values in which the analyte concentration values are positioned along a first direction according to a first time scale and along a second direction according to a second time scale. The analyte level of the analyte concentration values are modifiable and represented in a graphical display by one or more of a modification in the graphical display by introducing or using shapes, colors, shading, gradients of colors or shades, various intensities or contrast of different shades, transparency, opacity, buffer zones, graphical icons, arrows, animations, texts, numbers or gradual fading based on various health parameters, a magnitude of the analyte level and/or a statistical metric associated with the analyte level or group of analyte levels. In some implementations, the analyte application 330 operable on the display device 310 processes the datasets to produce the graphical display displayed on the display 345, which can be modified or adjusted according to the magnitude and/or metric of the analyte level(s).

Figure 4A:
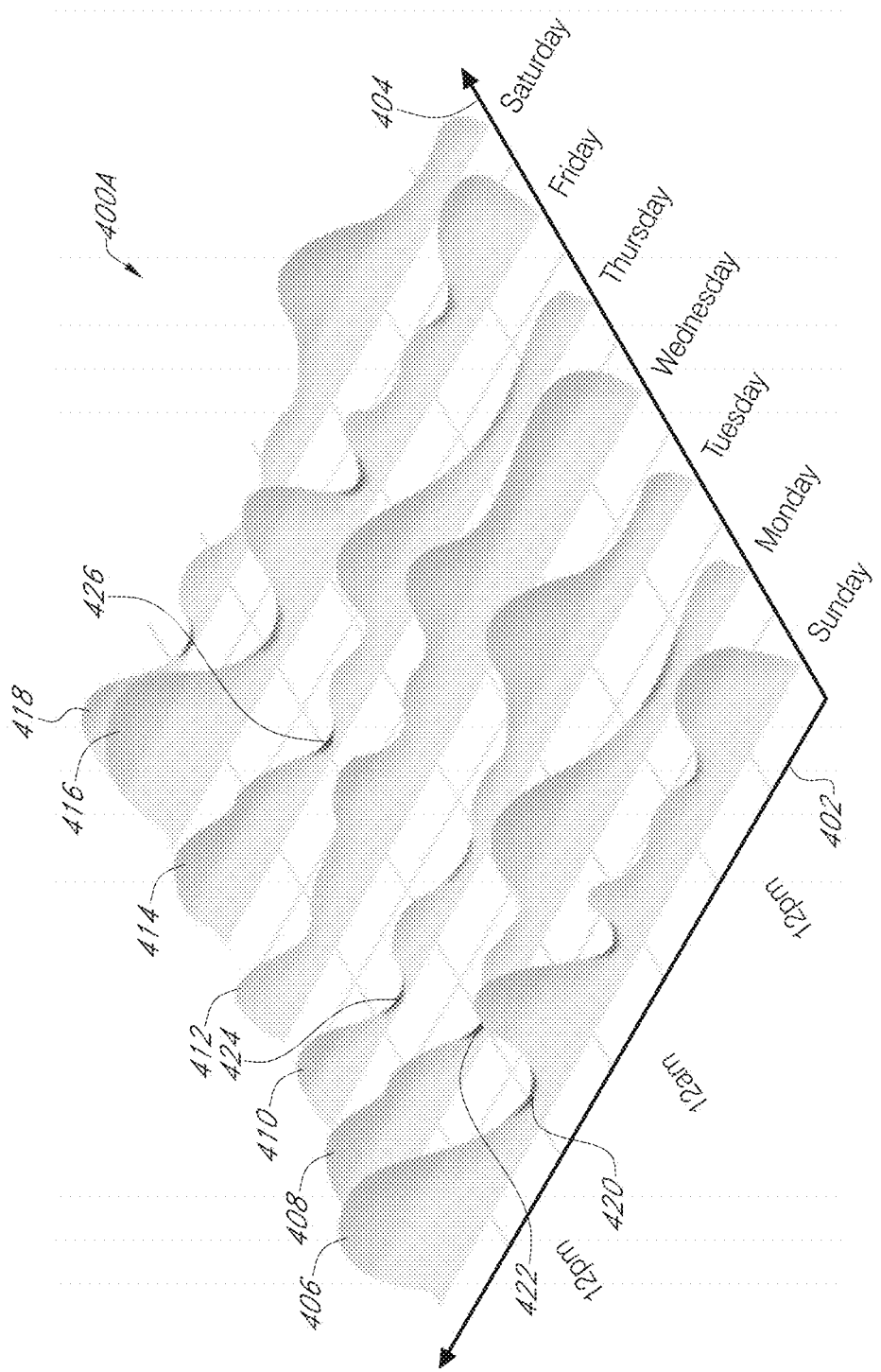
FIG. 4A is an illustration of a modified graphical display where the analyte concentration values are arranged and presented over a plurality of time intervals.

FIG. 4A is an illustration of a modified graphical display where the analyte concentration values are arranged and presented over a plurality of time intervals such that a viewer can easily detect patterns in the analyte data over the plurality of time intervals. The data structures or arrangements of analyte data produced by the embodiments described herein can generate modified graphical displays using color, shape, shading, size or other visuals to make detecting patterns in the analyte data easier for a viewer. The analyte application 330 can receive intermittent analyte concentration values corresponding to raw datasets and generate data structures or arrangements of analyte data capable of producing modified graphical displays, such as the graph 400A. The graph 400A illustrates the analyte concentration values over a first direction 402 according to a first time scale. The graph 400A also illustrates the analyte concentration values along a second direction 404 according to a second time scale. In the example shown in FIG. 4A, the first time scale is an hourly time scale over a day (24 hour period) and indicates the analyte concentration values throughout a day or multiple days over the daily time scale. The second time scale is a daily time scale over one week (7 days) and indicates the analyte concentration values throughout a week or multiple weeks over the weekly time scale. In the exemplary graph 400A, the concentration of analyte values for 24 hour periods over a week are shown, but other time intervals can be used. For example, the first direction 402 can be an hourly time scale over a daily period and the second direction 404 can be a monthly period (e.g., days of a particular month), weekday period (e.g., 5 days of Monday-Friday), weekend period, or other select period, e.g., including periods selected by the user on the user interface of the display device 310. Averaging or other numerical/statistical techniques can be used to extend or include additional data. For example, on the daily scale 404 averages or other statistically driven data of analyte concentration values of a particular day over a particular period in time can be represented as that day's analyte concentration values (e.g., analyte concentration values of Sundays over the past three months). In this manner, the graph 400A or other 7 day/24 hour period graphs are not limited to only the past 7 days values and an amalgamation of data over any period of user or system's choosing can be used to implement the graph 400A and other graphical displays described herein.

The exemplary graph 400A can be an isometric graph where the magnitude of analyte concentration values are represented by shapes along a vertical axis perpendicular to the first and second directions 402 and 404. The size of each shape can correspond to the magnitude of the analyte concentration value. In some implementations, color can be used to further indicate the magnitude of analyte concentration values or convey additional information about the analyte data. In other embodiments, various shading can be used to identify different magnitudes of analyte concentration values. For example, shades 406, 408, 410, 412, 414, 4116, 418, or if color is used, color yellow can be used in areas of the graph 400A where analyte concentration values exceed a high threshold. Shades 420, 422, 424 and 426 can be used to indicate areas of the graph 400A where the analyte concentration values drop below a low threshold. If color is used, color red may be used to indicated the regions where the analyte concentration values drop below a low threshold. In the arrangement of analyte concentration values in the exemplary graph 400A, a viewer can, at a glance determine the times in which the analyte concentration values are above a high threshold by observing the peaks in the data, or if color is used, the viewer can observe areas in yellow to quickly determine the times in which the analyte concentration values exceed a high threshold. The arrangement of analyte data as shown in the exemplary graph 400A enables a viewer to easily observe patterns in the analyte data. For example, in the exemplary graph 400A, areas 406, 408, 410, 412, 414, 416 and 418 corresponding to analyte concentration values around 6 pm show peaks, or if shading is used, the areas 406, 408, 410, 412, 414, 416, and 418 may be shown in darker shades (relative to other regions), indicating that the analyte concentration values tend to rise around 6 p.m. for the periods shown. Similar pattern can be observed if color is used. Observing such patterns in the analyte concentration values can enable a patient or the patient's caregivers to make better decisions in managing the patient's health.

Figure 4B:
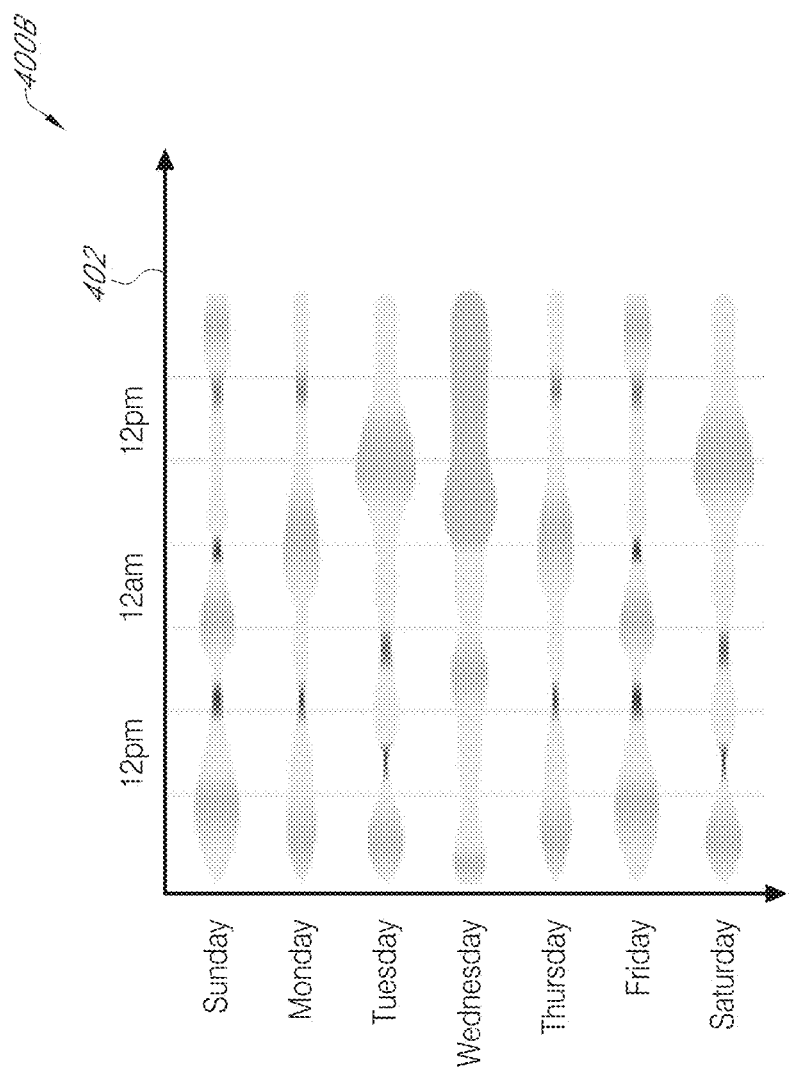
FIG. 4B is a modified graphical representation composed of the aerial view of the graph in FIG. 4A.

FIG. 4B is a graphical representation composed of the aerial view of the graph 400A, shown as graph 400B. Using the graph 400B, a user can readily observe patterns in the analyte data. In some implementations, the graph 400A can be displayed on display 345 in an interactive manner that allows the user to rotate, twist, yaw, and/or zoom in or out of the displayed graph 400A to manipulate the viewing of the graph 400A. In this regard, the display 345 may present the graph 400A, and allow the user to change the display to graph 400B. Like in graph 400A, the graph 400B is modified to represent the magnitude of analyte concentration values by shapes on the planar graph (e.g., along one or both of the first and second directions 402 and 404) to identify features in the analyte data, such as high analyte concentration levels illustrated by an enlarged width of the plot for each day at the particular time of day, and as low analyte concentration levels illustrated by a shrunken width of the plot for each day at the particular time. Similar to graph 400A, the graph 400B can also be modified to present shading or other visuals associated with the features, e.g., creating an effect that allows the viewer, at a glance, to determine the times in which the analyte concentration values are above or below high or low thresholds by observing the modifications of the graphical display in the data.

Figure 5:
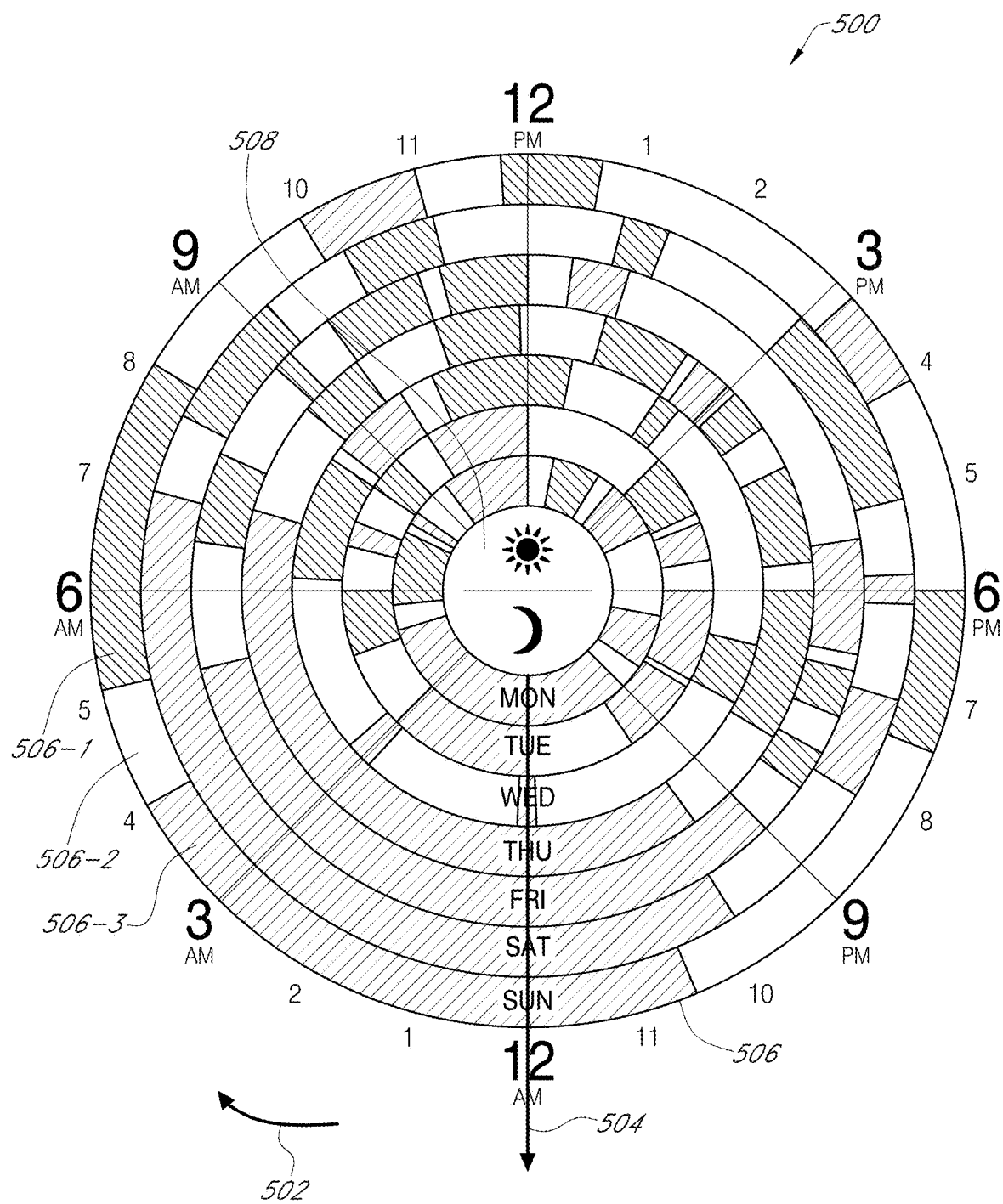
FIG. 5 is an illustration of an exemplary graphical display where the analyte concentration values are arranged and presented over a plurality of time intervals in a ring-shaped graph.

FIG. 5 is an illustration of an exemplary graphical display where the analyte concentration values are arranged and presented over a plurality of time intervals in a ring-shaped graph 500. In such implementations, a viewer can readily and easily detect one or more patterns in the analyte data over the plurality of time intervals based on the features produced by the graph 500. The graph 500 includes concentric rings where each ring represents analyte concentration values over a first direction 502 according to a first time scale. The concentric ring-shaped structure of the graph 500 allows for illustration of the analyte concentration values along a radial direction 504 according to a second time scale. In the example of the graph 500 shown in FIG. 5, the first time scale along the first direction 502 is an hourly time scale over a day (24 hour period) that can, for example, indicate hourly analyte concentration values, and the second time scale along the second time direction 504 is a daily time scale over one week (7 days) that can, for example, indicate daily analyte concentration values. In the exemplary graph 500, the analyte concentration values for 24 hour periods over a week are shown. Other time intervals can be used.

In the exemplary graph 500, each ring can be shaded, or if color is used, color coded to represent the magnitude of analyte concentration values relative to a high threshold, low threshold and a target region. For example, for the ring 506 which represents an exemplary display of analyte concentration values for a 24 hour period on a Sunday (or in some embodiments an amalgamation of Sundays over a period of time), a first shade 506-1 can be used to indicate times in which the analyte concentration values have dropped below a low threshold, a second shade 506-2 can be used to indicate times in which the analyte concentration values have been within a target range, and a third shade 506-3 can be used to indicate times in which the analyte concentration values have exceeded a high threshold. In some implementations, color can be used in addition to or instead of shades 506-1, 506-2 and 506-3. For example, the color red can indicate times in which analyte concentration values drop below a low threshold, the color white can indicate times in which analyte concentration values are within a target range, and the color yellow can indicate times in which the analyte concentration values exceed a high threshold. In some embodiments, one or more broken lines can be used in the display of graph 500 to indicate the presence of unreliable or tentative data.

The arrangement of analyte data as shown in the exemplary graph 500 enables a viewer to observe patterns in the analyte data. For example, by glancing at the exemplary graph 500, a viewer can quickly observe that for several days in a week, the analyte concentration values exceed the high threshold around 12 am.

In some embodiments, the data structures or arrangements of analyte concentration values can be configured to produce modified graphical displays in a central region 508 of the graph 500. For example, one or more additional visuals may be included in the central region 508 to indicate whether the data corresponds to day time or night time. As described above, the GUI 340 of the display device 310 may be configured to receive inputs from the user of the system 302 via, for example a touch-sensitive display. When such inputs are present, the user can touch or indicate a point on any of the concentric rings in the graph 500. Subsequently, a measurement of analyte concentration value corresponding to the touched point can be displayed in the central region 508. In some embodiments, if no input data from a user is received, an average value or other statistically driven representative data value corresponding to the entire time period shown in the graph 500 can be displayed in the central region 508. For example, a weekly average of analyte concentration values can be shown if the user does not indicate a point on the graph 500. In some examples, one or more additional graphical icons can be shown in the central region 508 to indicate additional information about the analyte concentration values represented in the graph 500. The graphical icons can indicate whether the data relates to day time, night time, weekend, workday or other temporal indication of the graphed data.

Figure 6:
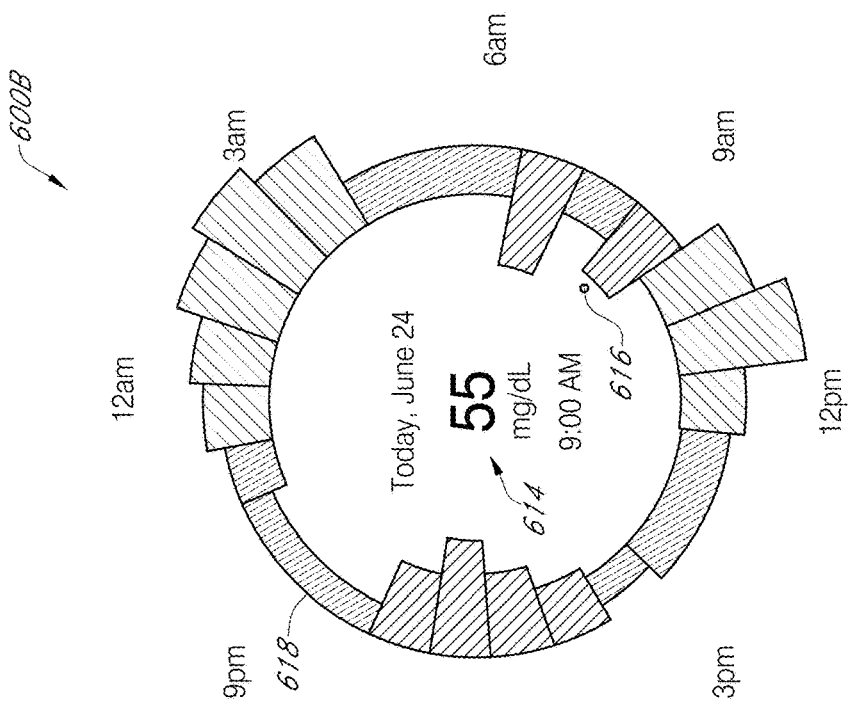
FIG. 6 illustrates a modified graphical display corresponding to the data structures and arrangements of analyte concentration values over a time interval.
Figure 6:
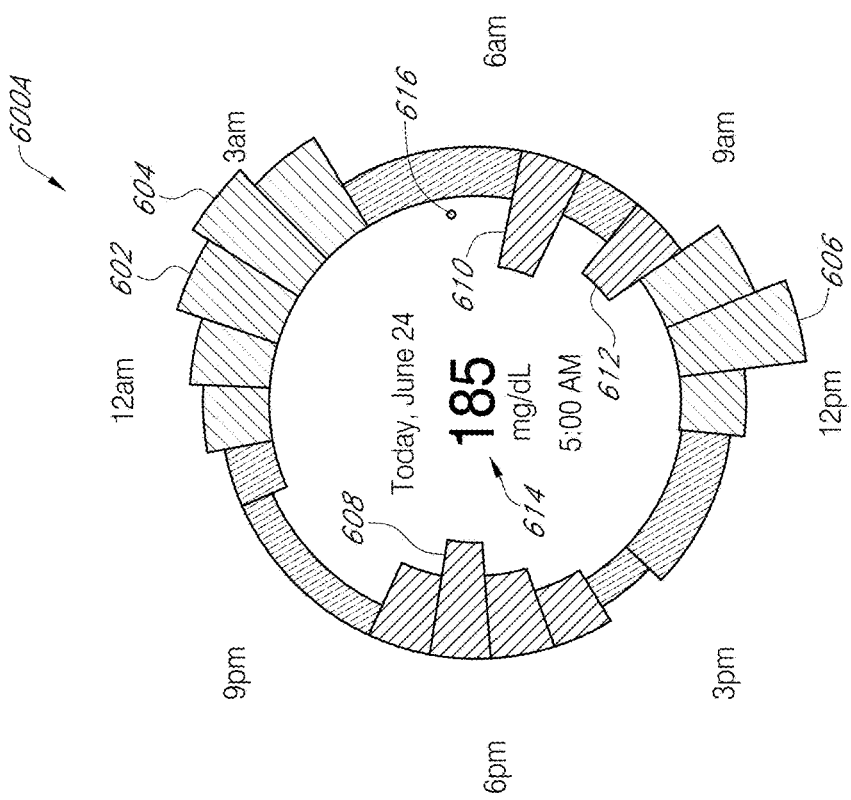

In some embodiments, the user can obtain additional information about a given day by providing an input to the analyte sensor app 330, for example by touching one of the rings of the graph 500. An additional graph indicating more details of the day corresponding to the touched ring can be shown instead of or in addition to the graph 500. FIG. 6 illustrates modified graphical displays corresponding to the data structures and arrangements of analyte concentration values over a time interval. The data structures and arrangements of analyte concentration values can generate the graphs 600A or 600B where the analyte concentration values are shown in shapes relative to a high and low threshold and a target region. The time intervals shown in the graphs 600A or 600B can be 24 hour periods corresponding to a touched ring in the graph 500. Other time intervals can be used. The graphs 600A or 600B can be displayed in parallel to, instead of, or in conjunction with the graph 500 when the user indicates a point on the graph 500. Additionally, the user can indicate different points along the graph 600A with a pointing device or via a touch screen, and the graph 600A can be updated and modified to display analyte data corresponding to the user's indicated point in a central region 614 of the graph 600A. The updated analyte data can include analyte concentration value, time and date corresponding to the point indicated by the user. In the example shown in the graph 600A, the user has indicated a desire to see analyte data corresponding to 5 a.m., June 24, by touching a touch display or by rotating a point 616 on the display of the graph 600A. The graph 600B is a modified graph 600A where the user has indicated a desire to see analyte data values corresponding to 9 a.m., June 24. The analyte concentration value and the corresponding time are accordingly modified and updated in the central region 614.

In the graphs 600A or 600B, analyte concentration values exceeding a high threshold can be shown by protrusions extending outward from the outer perimeter of the ring of the graphs 600A or 600B. Some examples of high threshold protrusions can include outward protrusions 602, 604 and 606. Analyte concentration values below a low threshold can be indicated by protrusions extending inward from the inner perimeter of the graphs 600A or 600B. Some examples of the low threshold protrusions can include inward protrusions 608, 610 and 612. As described above, in some embodiments, a user can touch a point 616 on or along the ring-shaped graph 600A and a measurement of analyte concentration value corresponding to the touched point can be shown in a central region 614 of the graph 600A.

In some embodiments, the graphs 600A or 600B can utilize shades, gradients or colors corresponding to the magnitude of analyte concentration values. For example, the graphs 600A or 600B can be generated or be modified to utilize various intensities and/or contrast of shading to indicate analyte concentration values. Shades 602, 604, 606 and similar shading can be used to indicate where the analyte concentration values exceed a high threshold. The intensity of the shading can correspond to the magnitude of analyte concentration values. Shades 608, 610, 612, and similar shadings can be used in the areas of the graphs 600A or 600B where the analyte concentration values are below a low threshold. A neutral shade, for example, shade 618 can be used to indicate analyte concentration values within a target range. A person of ordinary skill in the art can appreciate that the shades as described above are exemplary and other visuals including other shades, textures, gradients and/or colors can be used.

Figure 7:
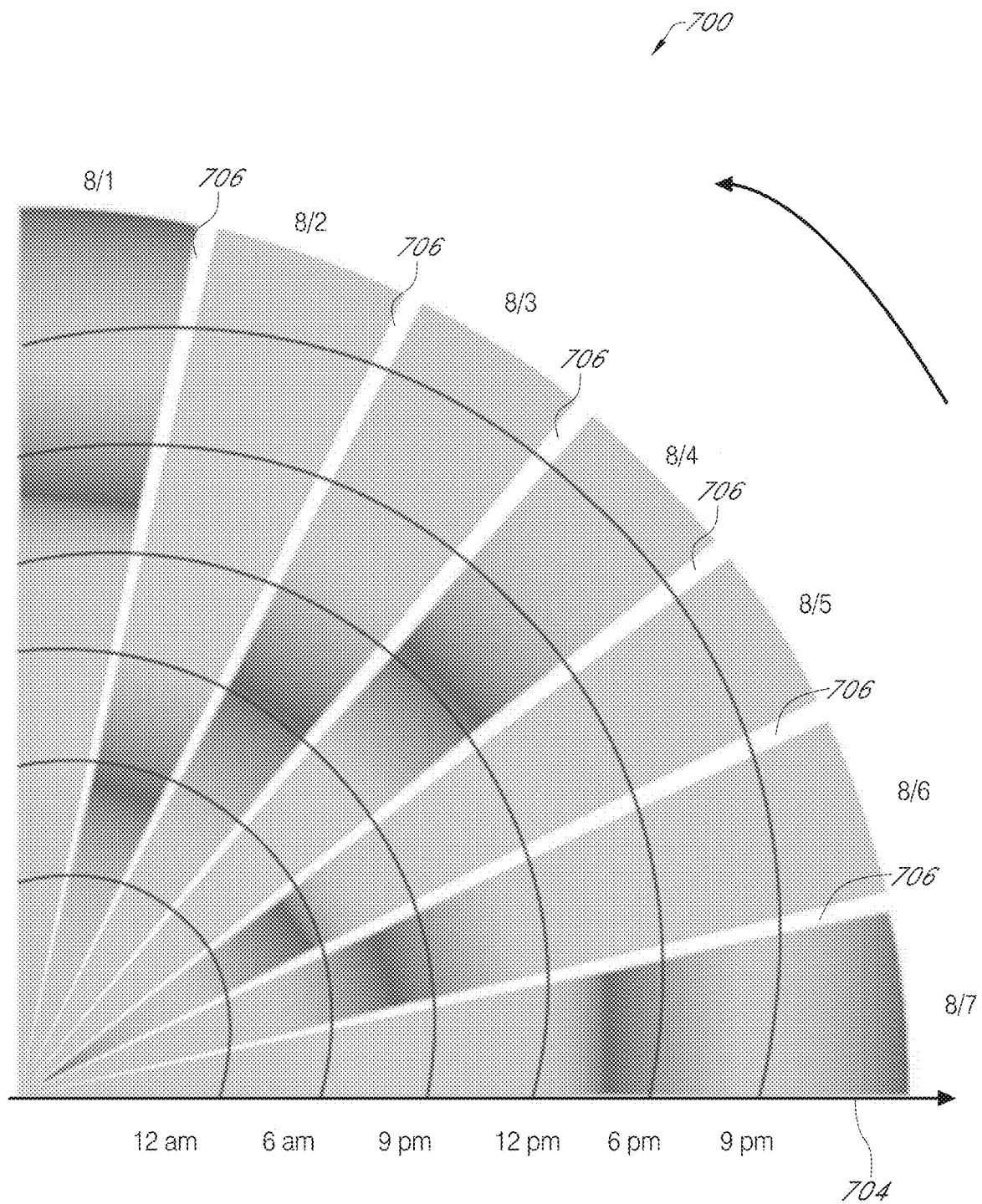
FIG. 7 is an illustration of a modified graphical display generated by the data structures and arrangements of analyte data over a plurality of time intervals.

FIG. 7 is an illustration of a modified graphical display generated by the data structures and arrangements of analyte data over a plurality of time intervals. The data structures and arrangements of analyte concentration values can generate a sectional graph 700 where the analyte concentration values are shown in a curved direction and in a radial direction in one or more sections. In such implementations, a viewer can readily and easily detect one or more patterns in the analyte data over the plurality of time intervals based on the features produced by the graph 700. The graph 700 illustrates the analyte concentration values over a first direction 702. The first direction 702 can be a curved direction according to a first time scale. The graph 700 also illustrates the analyte concentration values along a second direction 704 according to a second time scale. The second direction 704 can be a radial direction.

In the example of the graph 700 of FIG. 7, the first time scale is a daily time scale along the first direction 702 over one week (7 days) that can, for example, indicate daily analyte concentration values in 7 sections. The second time scale is an hourly time scale over a day (24 hour period) that can, for example, indicate hourly analyte concentration values. Other time intervals can be used. Each section of the graph 700 can represent hourly analyte concentration values over a 24 hour period with analyte concentration values of other 24 hour periods shown adjacent to it. In some embodiments, the sections of the graph 700 can optionally be separated by one or more buffer zones 706. The analyte data represented in the graph 700 need not be limited to analyte data over a 7 day period. An amalgamation of analyte data for each day displayed can also be used to generate the graph 700.

The graph 700 can be shaded or color-coded, as described above in relation to the embodiments of FIGS. 5 and 6 to convey additional information about the analyte concentration values.

A user can click on any section of the graph 700 to obtain an exclusive view of the time interval corresponding to that section. In some embodiments, upon selection of a section, the graphical display 700 can be modified to show the remaining sections collapsing into the chosen section where only the chosen section is subsequently displayed to provide a graphical display focused on the chosen section. While the remaining sections are in the motion of collapse, a graph of highs and lows corresponding to the analyte data relative to a high and low threshold can also be displayed in tandem with the graph 700.

Figure 8:
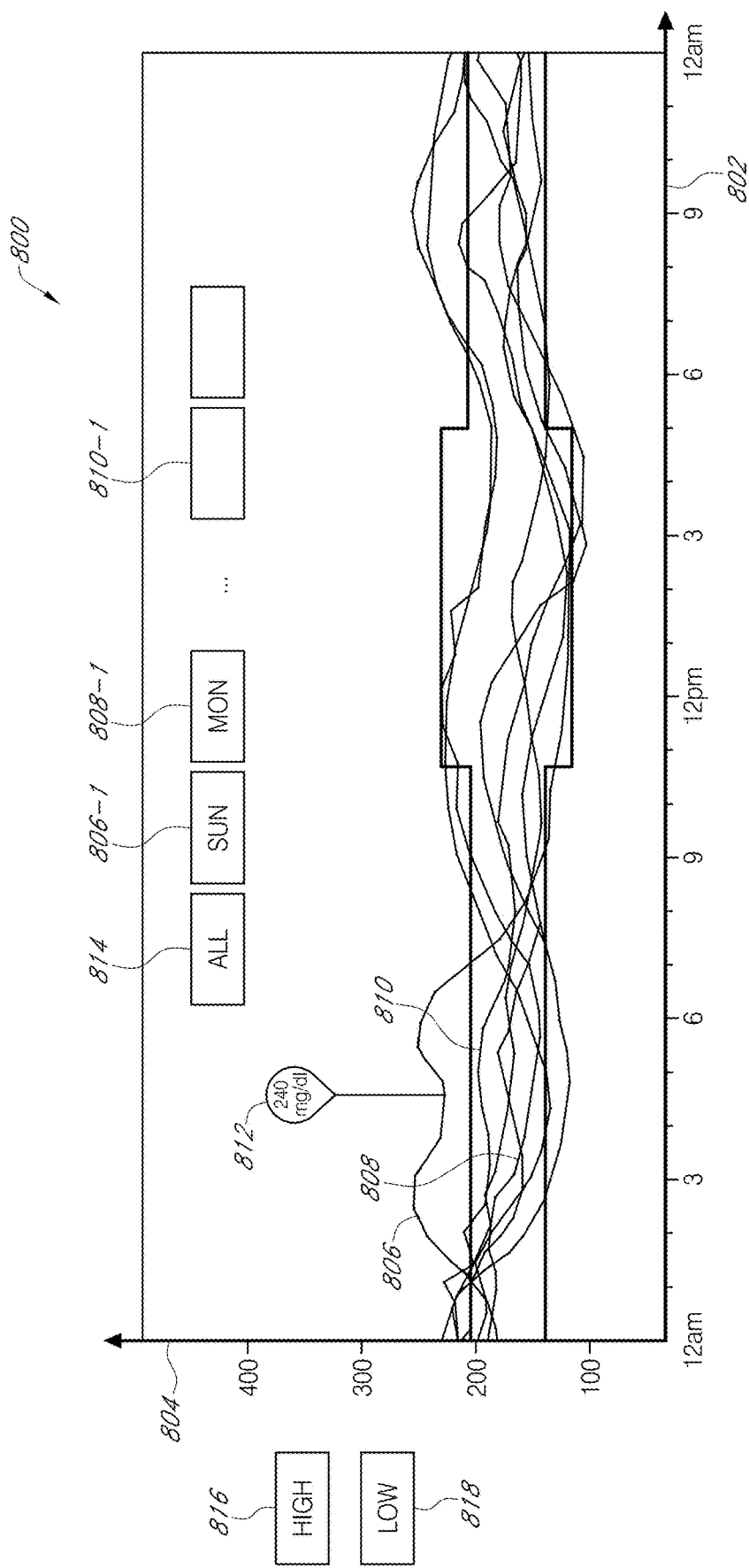
FIG. 8 is an illustration of a modified graphical display generated by the data structures and arrangements of analyte data over a plurality of time intervals.

FIG. 8 is an illustration of a modified graphical display generated by the data structures and arrangements of analyte data over a plurality of time intervals. The data structures and arrangements of analyte concentration values can generate a graph 800 where the analyte concentration values are shown for multiple time intervals over a time scale 802. The magnitude of analyte concentration values can be represented on the vertical axis 804. The time scale 802 can represent a 24 hour period. Although other time periods may be configured and displayed. Each line graph, 806, 808, 810 and the like, represents the analyte concentration values over a different 24 hour period. For example, analyte concentration values over a week can be represented by the line graphs 806, 808, 810 and so forth. An amalgamation of analyte data for each day displayed can also be used to generate the line graphs 806, 808, 810 and so forth. Each line graph can utilize areas under the curve shaded in different opacities to visually distinguish the analyte concentration values of different time intervals. A user can indicate a point on the graph 800 by a pointing device or via a touch screen and a call-out window 812 can be shown including the measurements of the analyte concentration value corresponding to the chosen point on the graph 800.

In some embodiments, one or more side tabs can be utilized to visually isolate analyte data and present a more focused view. For example, if the line graphs 806, 808, 810 and the like represent a week of analyte data, a collection of side tabs or buttons 806-1, 808-1, . . . , 810-1 can be used, where activating a side tab or button 806-1, more prominently displays the line graph 806 and its corresponding area under the curve and opacity relative to the other displayed analyte data. The unselected analyte data can be shown in less prominent shades. A side tab or button 814 can activate and prominently display all analyte data.

In some embodiments, one or more buttons or icons can be used to isolate the analyte data relative to high and low threshold values. For example, in the graph 800, a user can point to a high threshold button 816 via a pointing device or by touching a touch screen. The graph 800 can be modified to visually distinguish the areas of analyte data with a magnitude higher than one or more high thresholds. The visual distinction can be created by using different shades, gradients or if color is used, by using different intensity or gradients of colors. Similarly, a user can point to a low threshold button 818 via a pointing device or by touching a touch screen. The graph 800 can be modified to visually distinguish the areas of analyte data with a magnitude lower than one or more low thresholds. The buttons or icons 816 and 818 can be displayed as depressed thereby activating their corresponding display or they may be displayed as undepressed thereby deactivating their corresponding display. In some embodiments, cumulative information about the analyte data corresponding to the analyte data captured by the graph 800 can be shown. For example, one or more icons or visuals indicating the percentages of the analyte data above the high thresholds, below the low thresholds and within the high and low thresholds can be shown respectively. The percentage icons can be shown simultaneously as their corresponding high or low threshold button has been depressed. In one embodiment, the percentage icons can be circular in shape where the thickness, color intensity, or opacity of the circle is determined based on the percentage shown in the center of the circle.

The high or low threshold values can be inputted by a user or be derived from the patient data or multiple patient data available to the system 302. Multiple thresholds can be inputted, defined or derived for different time intervals, time periods or dates. The graph 800 can be rendered in color as described above in relation to the embodiments of FIGS. 5 and 6.

Figure 9:
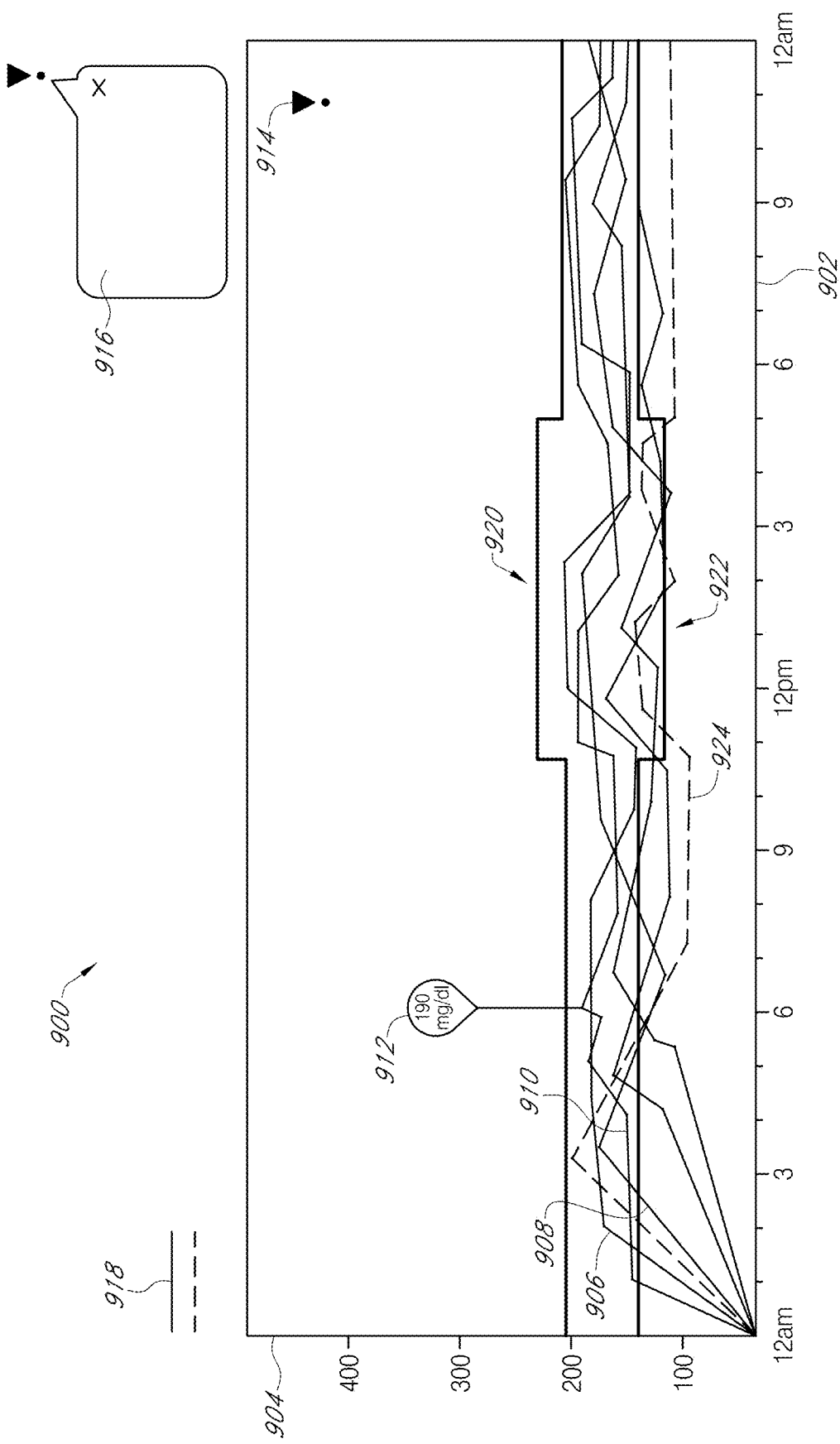
FIG. 9 is an illustration of a modified graphical display generated by the data structures and arrangements of analyte data over a plurality of time intervals.

FIG. 9 is an illustration of a modified graphical display generated by the data structures and arrangements of analyte data over a plurality of time intervals. The data structures and arrangements of analyte concentration values can generate a graph 900 where the analyte concentration values are shown for multiple time intervals over a time scale 902. The magnitude of analyte concentration values can be represented on a vertical axis 904. The time scale 902 can represent a 24 hour period. Although other time periods may be configured and displayed. Each of the example line graphs 906, 908, 910 and the like represent the analyte concentration values over a different 24 hour period. For example, analyte concentration values over a week can be represented by line graphs 906, 908, 910 and so forth. A user can point to any portion of the graph 900 via a pointing device, for example by moving a mouse pointer over the graph 900 or by touching a display of a touch screen displaying the graph 900. An icon or an over-lay graphical display, for example, a call-out window 912 can be shown on the graph 900 where a user has pointed, where the call-out window can display the measurement of the analyte data corresponding to the point chosen by the user. If a user clicks or points to a portion of the graph 900 where overlapping or future data is detected, a graphical display 914 can appear within the area of the graph 900 directing the user to click for more information. If the user clicks on the graphical display 914, an additional graphical display, for example a text box 916 can appear within the area of the graph 900 providing additional information to the user.

In some embodiments, the line graphs 906, 908, 910 and the like can be rendered in different line shapes or styles depending on the reliability of the underlying analyte data which they represent. For example, a dashed line style can indicate uncertain analyte data. A continuous line can indicate reliably tracked analyte data. A dotted line 924 can indicate projected future analyte data. A graph key 918 along with descriptions of each line graph styles can be included with the display of the graph 900.

In some embodiments, one or more buttons or icons can be used to isolate the analyte data relative to high and low threshold values. For example, in the graph 900, a user can point to a high threshold button or other virtual menu or button option via a pointing device or by touching a touch screen. The graph 900 can be modified to visually distinguish the areas 920 of analyte data with a magnitude higher than one or more high thresholds. The visual distinction can be created by using different shades, gradients or if color is used, by using different intensity or gradients of colors. Similarly, a user can point to a low threshold button or other virtual menu or button option via a pointing device or by touching a touch screen. The graph 900 can be modified to visually distinguish the areas 922 of analyte data with a magnitude lower than one or more low thresholds. The buttons or icons can be displayed as depressed thereby activating their corresponding display or they may be displayed as undepressed thereby deactivating their corresponding display.

Figure 10:
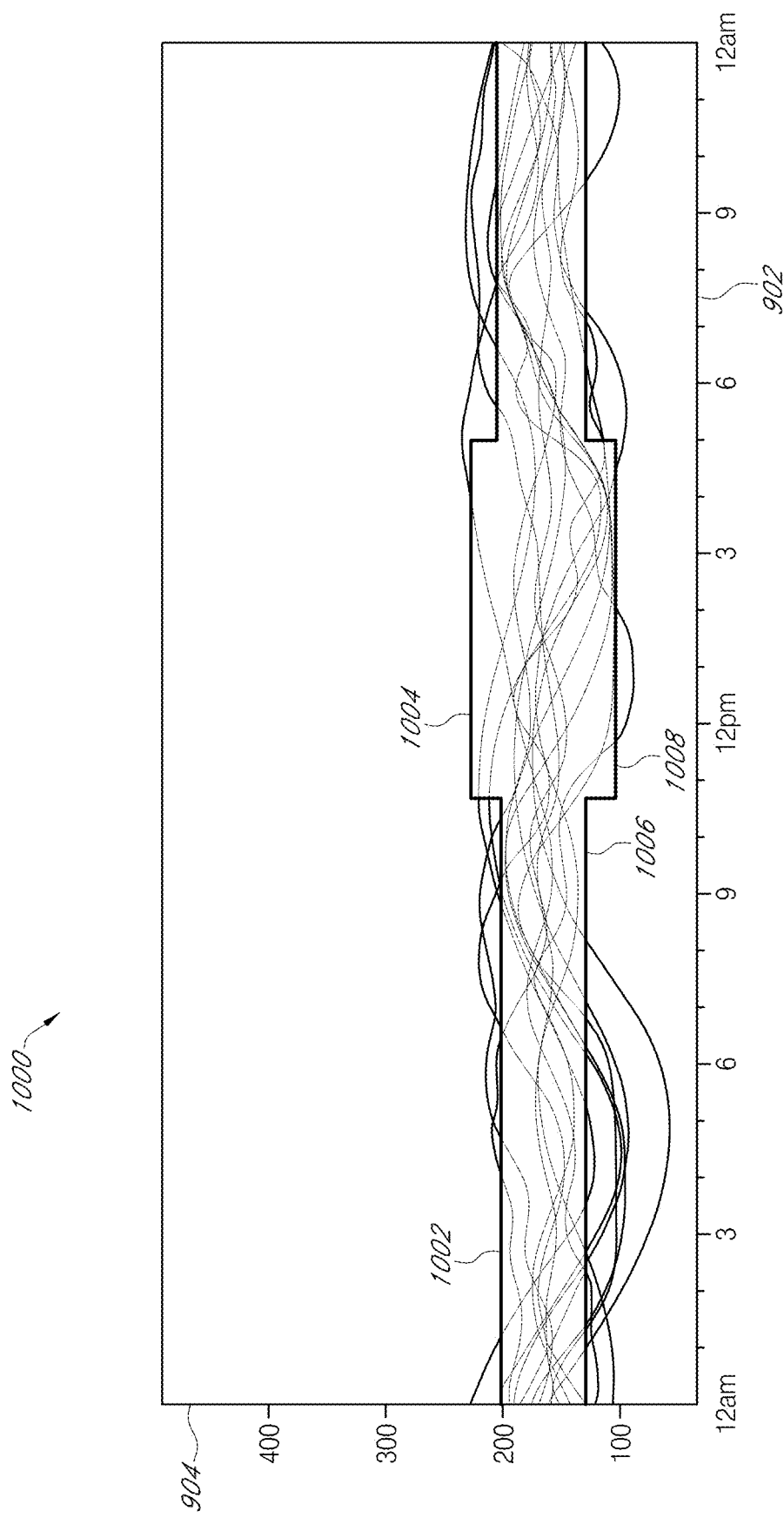
FIG. 10 is an illustration of the modified graphical display of FIG. 9.

FIG. 10 is an illustration of the modified graphical display of FIG. 9. The graph 1000 is similar to the graph 900 where the threshold view buttons or other virtual menu or button options are depressed or activated. Areas above one or more high threshold values 1002 and 1004 are visually distinguished by a first style of shading to indicate the times in which analyte data values have exceeded the high thresholds 1002 and 1004. Areas below one or more low thresholds 1006 and 1008 are visually distinguished by a second style of shading to indicate times in which analyte data values have dropped below the low thresholds 1006 and 1008. As discussed above in relation to FIG. 9 other means of visually distinguishing the high and low excursions of analyte data can be used. For example, if color is used, color gradients or different intensities of color can be used.

Figure 11:
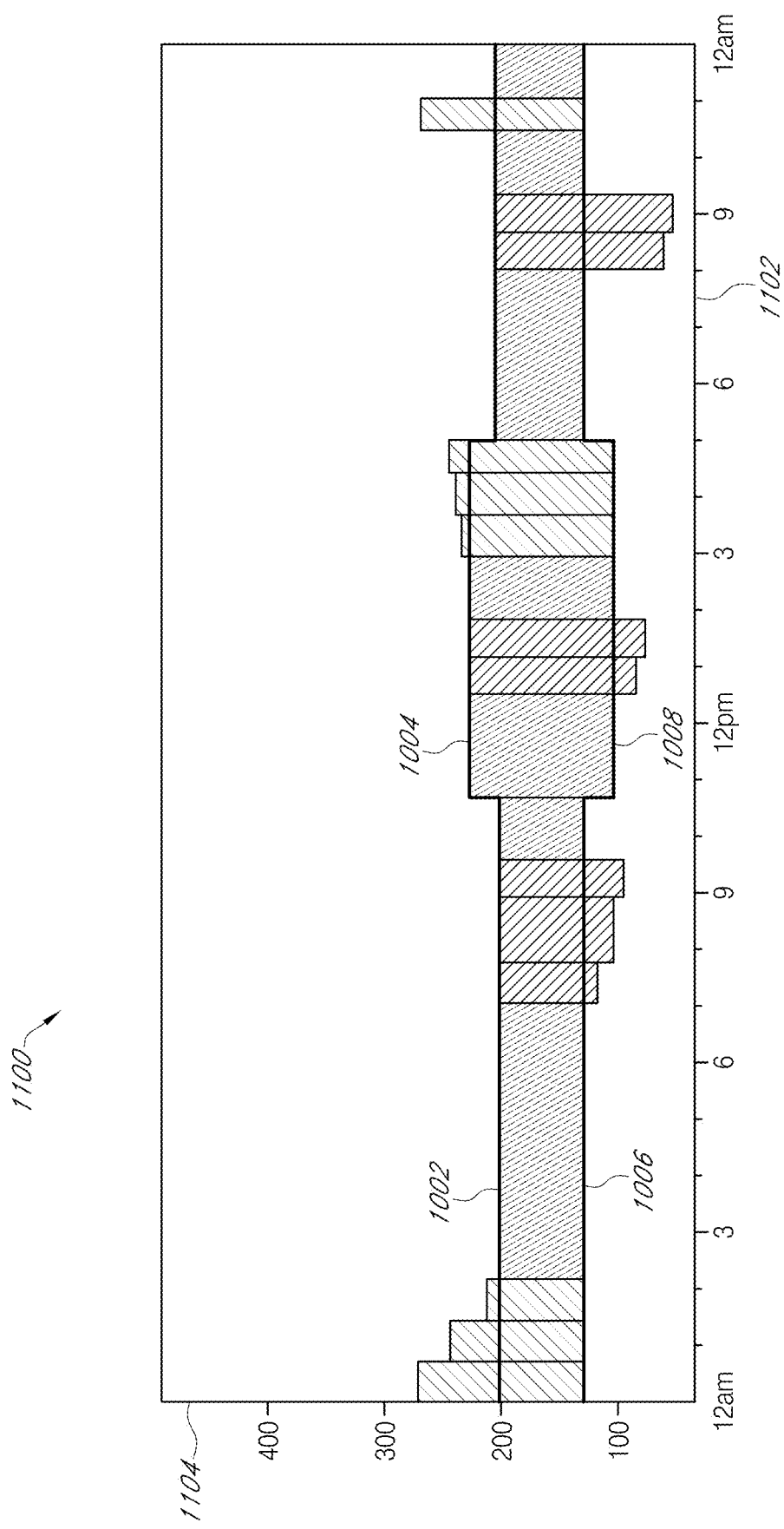
FIG. 11 is a modified graphical display of FIG. 10 providing a daily breakdown of analyte values.

An example graph 1100, as shown in FIG. 11 can be used to provide a daily break down of any of the line graphs 906, 908, 910 or the like from the graph 900, and similarly of features 602, 604, 606, 608 and the like from the graph 600A or 600B. Other time intervals can alternatively be used. In the exemplary graph 1100, a bar graph is used to view the daily break down of analyte data. An axis 1102 indicates time. The magnitude of analyte concentration values can be represented on a vertical axis 1104. A user can trigger the display of the graph 1100 by pointing to a particular line graph 906, 908 or 910 via a pointing device or by touching a touch screen. One or more lines can indicate the range of average analyte concentration values of the underlying analyte data used to generate the graph 1100 and/or threshold levels. In the example shown in FIG. 11, the high threshold levels 1002 and 1004 and low threshold levels 1006 and 1008 are displayed on the graph 1100.

Figure 12:
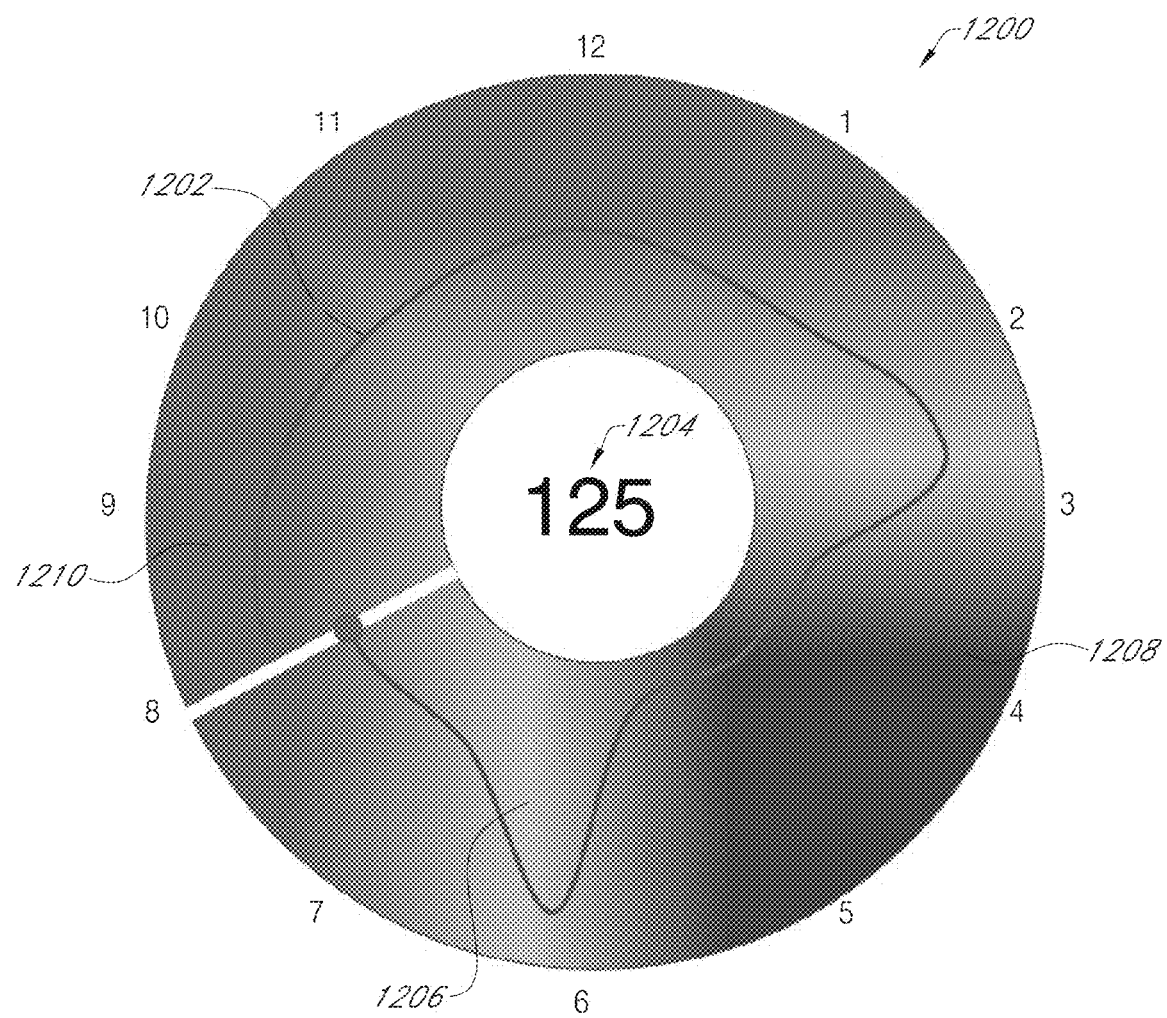
FIG. 12 is an illustration of an exemplary graphical display where the analyte concentration values are shown on a clock dial graph.

FIG. 12 is an illustration of an exemplary graphical display where the analyte concentration values are arranged and presented over a plurality of time intervals and are shown on a clock dial graph 1200, such that a viewer can easily detect one or more patterns in the analyte data over the plurality of time intervals. In one implementation, the graph 1200 can utilize different shades each corresponding to analyte concentration values above a high threshold, below a low threshold, or in-target values. Analyte concentration values of several time intervals (for example several days) can be superimposed to make up the graph 1200. In this scenario, a gradient can be created to indicate a pattern over the plurality of time interval depicted in the graph 1200. For example, if a dark shade 1208 is used to indicate analyte concentration values below a low threshold, and the analyte concentration values for times between 12 a.m. and 12 p.m. for a seven day period are superimposed to make up the graph 1200, a gradient of the shade 1208 for times between 3 a.m. and 6 a.m. can indicate a drop in analyte values during that time over the seven day period. The user can conveniently spot this pattern in the analyte data over the 7 day time period and take appropriate action to better manage their health. In some embodiments, an analyte trend graph can also be included in the graph 1200 indicating changes in the analyte concentration values with a line graph 1202.

In some implementations, the line graph 1202 can be an analyte level trace overlaid on the clock dial graph 1200 such that higher analyte levels are closer to an outer curved region of the graph 1200 and lower analyte levels are closer to an inner curved region of the graph 1200, or vice versa. As described, in the graph 1200, various gradient and/or contrasting shades may be used to represent various analyte level values. The higher analyte levels can be in a first shade 1206, the lower analyte levels can be in a second shade 1204, and the analyte levels between the higher and lower analyte levels can be in a third shade 1208. The analyte level trace 1202 can include an average analyte level of daily analyte concentration values or alternatively a current analyte level over an hourly time scale.

In some implementations, a most recently detected analyte concentration value or an average value of analyte concentration values can be displayed in the center 1204 of the graph 1200. In some implementations, additional icons can indicate whether the data depicted in the graph 1200 corresponds to day time or night time values.

In some embodiments, a graphical display 1200 implemented can be rendered on the display 345. The display device 310 can receive an input from the user (for example a tap on the touch screen 345) and flip the graph 1200 to show a display graphic depicting the percentages of the times the user has experienced analyte concentration values above the high threshold, below the low threshold or within the two thresholds for the time periods depicted in the graph 1200.

Figure 13A:
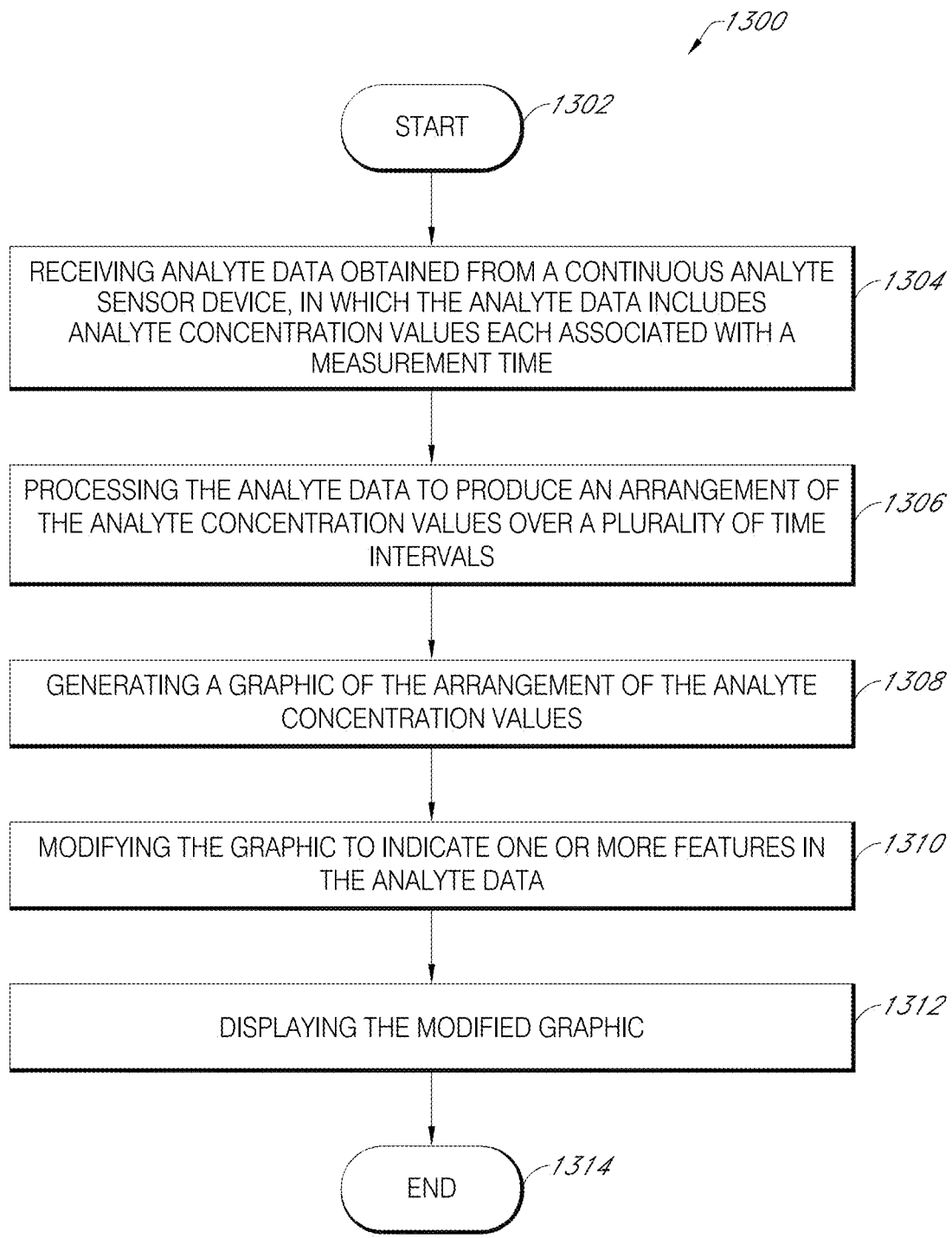
FIG. 13A illustrates a flow chart of an exemplary method by which the disclosed system can produce and display modified graphical displays.

FIG. 13A illustrates a flow chart 1300 of an exemplary method by which the system 302 can produce and display modified graphical displays 400A, 400B, 500, 600, 700, 800, 900, 1000, 1100 and 1200 according to some embodiments. The process 1300 starts at block 1302. At block 1304, the analyte sensor application 330 can receive at the display device 310, analyte data obtained from the continuous analyte sensor device 375, or from the sensor measurement circuitry 370. The analyte data received at the analyte sensor application 330 can include analyte concentration values associated with analyte measurements during a time period. At block 1306, the analyte sensor application 330 can cause the processor 335 to process, at the display device 310, the analyte concentration values to produce an arrangement of the analyte concentration values over a plurality of time intervals. At block 1308, the analyte sensor application 330 can cause the processor 335 to generate a graphic of the arrangement of the analyte concentration values. At block 1310, the analyte sensor application 330 can cause the processor 335 to modify the graphic to indicate one or more features in the analyte concentration values. For example, the modification of the graphic to indicate one or more features in the analyte concentration values can modify the graphic to indicate one or more patterns of the analyte concentration values. At block 1312, the analyte sensor application 330 can cause the processor 335 to display at the display 345 of the display device 310 the modified graphic. The method ends at block 1314.

Figure 13B:
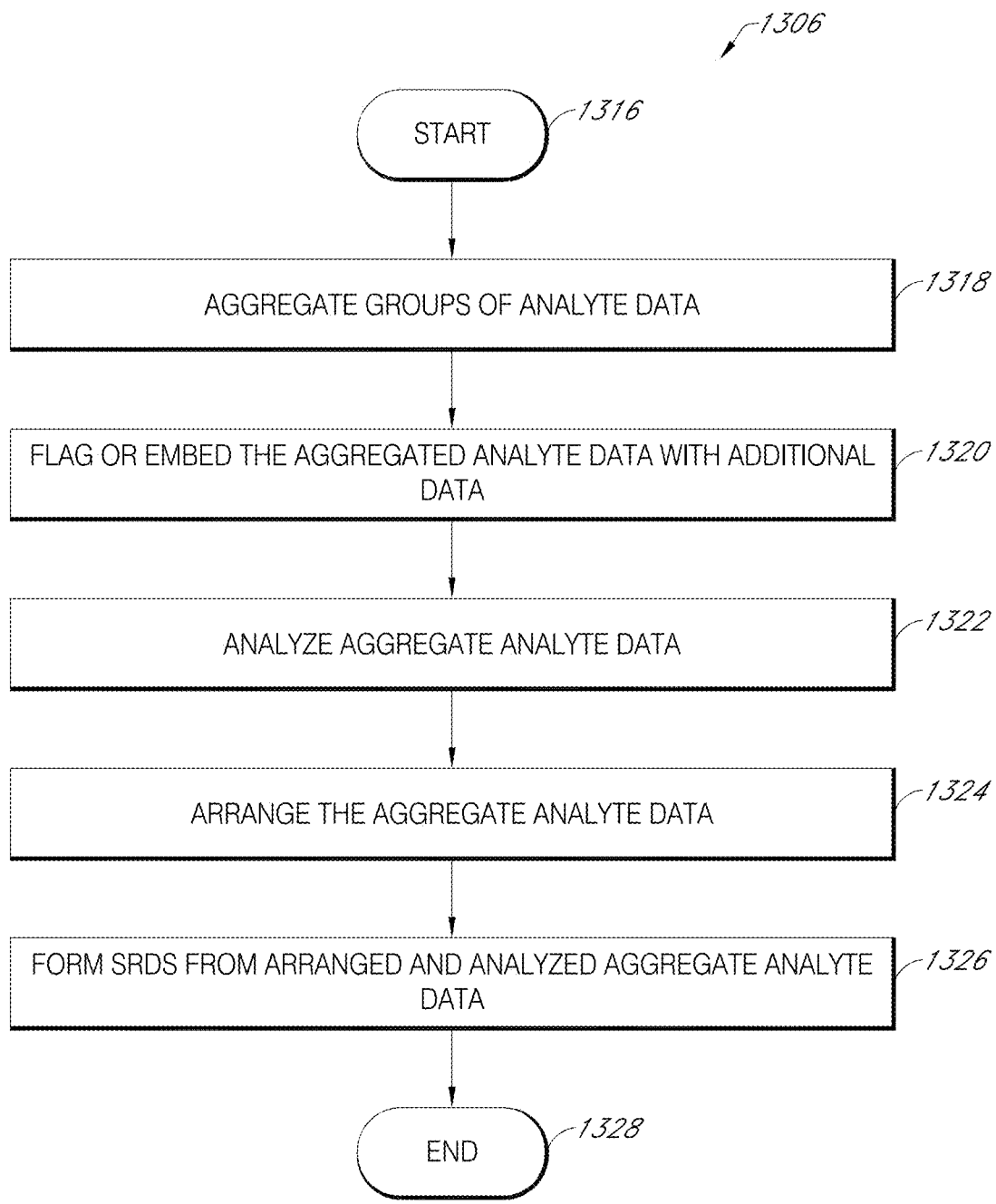
FIG. 13B illustrates a flow chart of an exemplary method to implement a process identified in the process of FIG. 13A.

FIG. 13B illustrates a flow chart 1306 of an exemplary method to implement the process identified in block 1306 of FIG. 13A to process analyte data, such as the analyte concentration values, to produce an arrangement of the analyte concentration values over a plurality of time intervals. While this exemplary method is described where the processor 335 of the display device 310 implements the method, it is understood that other devices of the system can be configured to implement the method. The process 1306 begins at block 1316. In some implementations, at block 1318, the processor 335 aggregates groups of analyte concentration values based on their time values for a time of day. For example, days, weeks, months or other time periods of analyte data can be aggregated based on every 5, 10, 15 or other time points throughout the day, e.g., such as analyte concentration values grouped at 12:00 pm, 12:10 pm, 12:20 pm, 12:30 pm, etc. In some instances, the analyte concentration values may not all align with the same time of day time value, such as 12:00 pm, 12:01 pm, 11:59 pm. In such instances, the processor 335 can associate the analyte concentration values to a particular time point (e.g., 12:00 pm) for all values falling within a range, e.g., ±5 min.

At block 1320, the processor 335 can flag or embed the analyte data with additional data used for generating graphics at the block 1308 of FIG. 13A or generating modified graphic at the block 1310. The graphics can, among other graphics, include the graphical displays described above in relation to the graphs 400A, 400B, 500, 600, 700, 800, 900, 1000, 1100 and 1200. The additional data can include flagging or tabulating the analyte data based on one or more time scales, relationship of the tagged or tabled analyte data with one or more sets of high and low thresholds of analyte data in the host or a group of hosts, contextual information related to the aggregated analyte data collected at the block 1318, and any other information that may be later recalled or otherwise used to generate or modify a graphical display of the graphs described above. In some implementations, the process of flagging or embedding additional data with the analyte data is performed after analyzing the data, as shown at block 1322.

At block 1322, the processor 335 analyzes the grouped analyte concentration values. In some implementations, the processor 335 can determine the max and/or min value(s) for the grouped values. In some implementations, the processor 335 can determine the mean, median, standard deviation, or other statistical metric for the grouped values. Additionally, the processor 335 can perform Fourier transforms, Laplace transforms and/or sampling techniques on the grouped analyte concentration values to aid in forming a modified graphical display indicative of patterns in the analyte data, for example, at block 1310 of FIG. 13A. In some implementations, the process at block 1320 is performed on the analyzed groups of analyte concentration values after block 1322, in which the analyzed groups of analyte concentration values can be flagged or embedded with additional data for use in modifying the graphic at the block 1310. For example, a group of analyzed analyte concentration values may have a mean, median, standard deviation, etc. that exceeds a predetermined threshold or is outside a predetermined range, and could be flagged or embedded with additional data.

At block 1324, the processor 335 arranges the analyzed groups of analyte concentration values based on spatial or temporal parameters associated with types of modified graphics as described above in relation to the graphs 400A, 400B, 500, 600, 700, 800, 900, 1000, 1100 and 1200. For example, if a graphic includes a second time scale, the processor 335 can arrange the analyzed groups of analyte concentration values according to their time of day time values for a second time scale, such as days of a week, days of a month, selected days of a time period (such as working days, vacation days, or other user-selected time frame).

At block 1326, the processor 335 forms a dataset of the arranged, analyzed groups of analyte data. The dataset is structured such that it can be processed by the processor 335 as a basis to form a graphic display displayable on the display 345, e.g., at block 1308 of FIG. 13A. As described above, the dataset generated at the block 1326 is self-referential and includes the information to generate the graphic at the block 1308 of FIG. 13A or the modified graphic at the block 1310 of FIG. 13A.

Some advantages of the method and system can include the following. The self-referential dataset (SRDS) generated at the block 1326 obviates the need for the processor 335 to search for and recall the necessary information from various parts of the system 302 to generate the graphics of the blocks 1308 and 1310. Otherwise, for example, without the self-referential dataset generated at the block 1326, the processor 335 would have to search, query and/or call various parts of the system 302, every time the user requests a different graphic or requests a modification of the displayed graphic. As such, the self-referential dataset generated at the block 1326 improves the operation of the system 302 by reducing complexities in data processing and data transmission between various parts of the system 302. For example, using the SRDS, the system does not have to store or process additional algorithms, e.g., such as pattern recognition algorithms, to produce outputs such as displays to convey pattern information to the user. Additionally, self-referential dataset generated at the block 1326 can reduce the amount and frequency of data to be transmitted for the purpose of generating graphical displays of blocks 1308 and 1310 of FIG. 13A. Associated processing or graphing algorithms to be stored and operated are also accordingly reduced and the performance of the system 302 is increased.

The process 1306 ends at the block 1328 and further processing is handed over to the block 1308 of FIG. 13A.

Figure 13C:
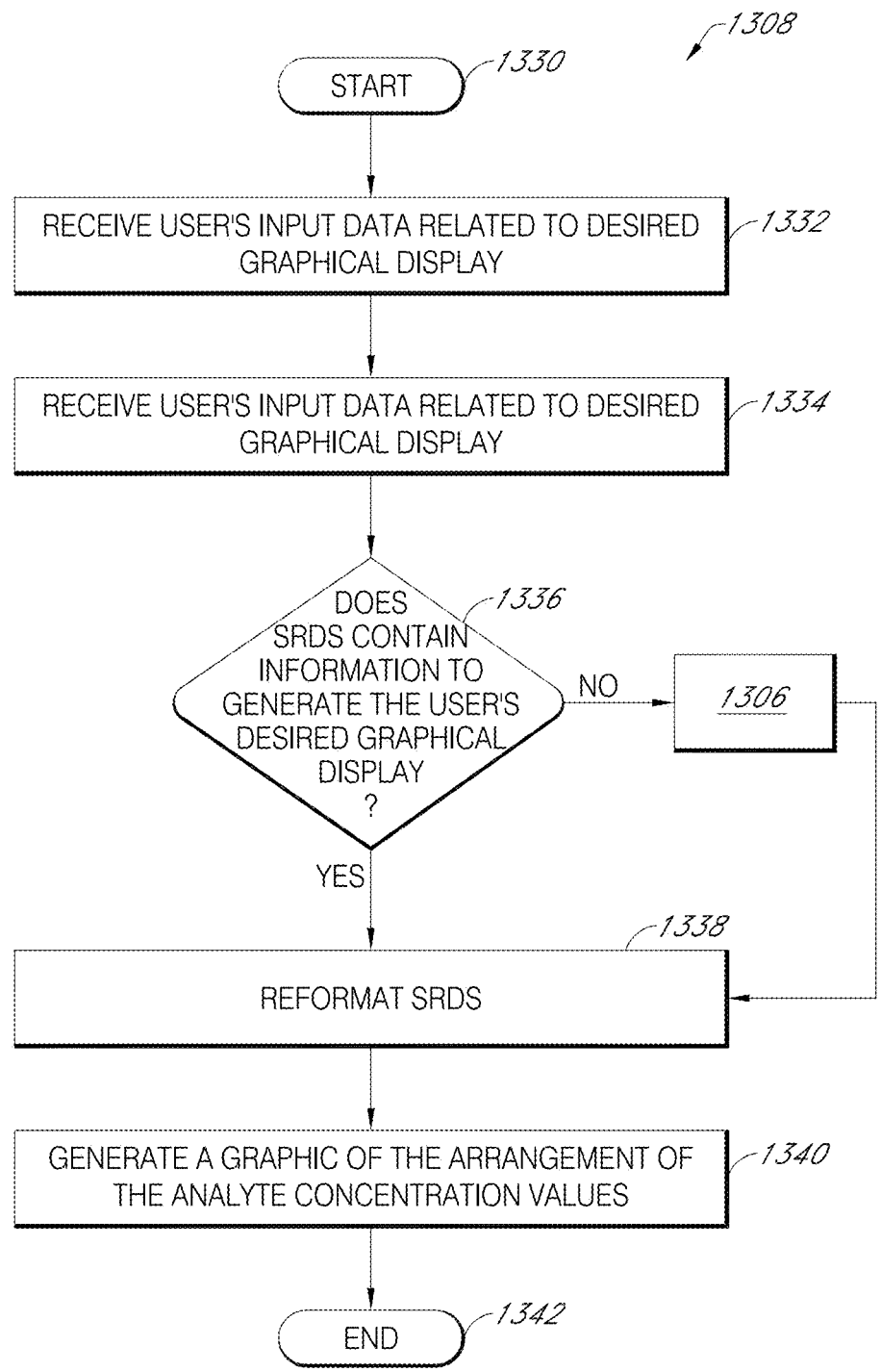
FIG. 13C illustrates a flow chart of an exemplary method to implement a process identified in the process of FIG. 13A.

FIG. 13C illustrates a flow chart 1308 of an exemplary method to implement the process identified in block 1308 of FIG. 13A to generate a graphic of the arrangement of the analyte concentration values. While this exemplary method is described where the processor 335 of the display device 310 implements the method, it is understood that other devices of the system can be configured to implement the method. The process 1308 begins at block 1330. At block 1332, the processor 335 receives user's input data related to the user's desired graphical display. These can include, the type of graphical display desired (e.g. text, charts such as bar, pie, or other charts, and/or graphical displays such as 400A, 400B, 500, 600, 700, 800, 900, 1000, 1100 and 1200, or other graphical displays), and/or the ranges for which the user desires to see a graphical display with respect to one or more time scales in which the datasets of the process 1306 have been formed.

At block 1334, the processor 335 can receive hardware or software data related to the display device 310 or display 345. The display data can, for example, include: size, dimensions or resolution of the available viewing area, available orientations and available input devices. At block 1336, the processor 335 can determine whether the self-referential dataset formed at the block 1326 contains all the information needed to generate the user's desired graphic. As an example, the user might have requested a display of analyte data falling outside of the range captured in the self-referential dataset. In these instances, the process 1306 can be repeated and a more comprehensive self-referential dataset can be formed. In most cases however, the self-referential dataset is formed in a manner to contain all the necessary information and data for generating a user's desired graph.

At block 1338, the processor 335 reformats the self-referential data set based on the user's input data and the display device data and produces a formatted self-referential data set. For example, if a user's desired range of display is smaller than the range of data captured in the self-referential dataset, the processor 335 at the block 1338 can filter the unwanted or out of range data by erasing that data from the self-referential data set. At block 1340, the processor 335 generates a graphic of the arrangement of the analyte concentration values based on the formatted self-referential data set. The processing involved at the block 1340 can depend on the type of the graphic chosen by the user and the display device data. For example, if the user desires a graph 400A as described above in relation to FIG. 4A, the processor 335 can determine the correct scale for generating the graph 400A based on the available viewing area and the orientation of the display device 345.

The process 1308 ends at the block 1342 and further processing is handed over to the block 1310 of FIG. 13A.

Figure 13D:
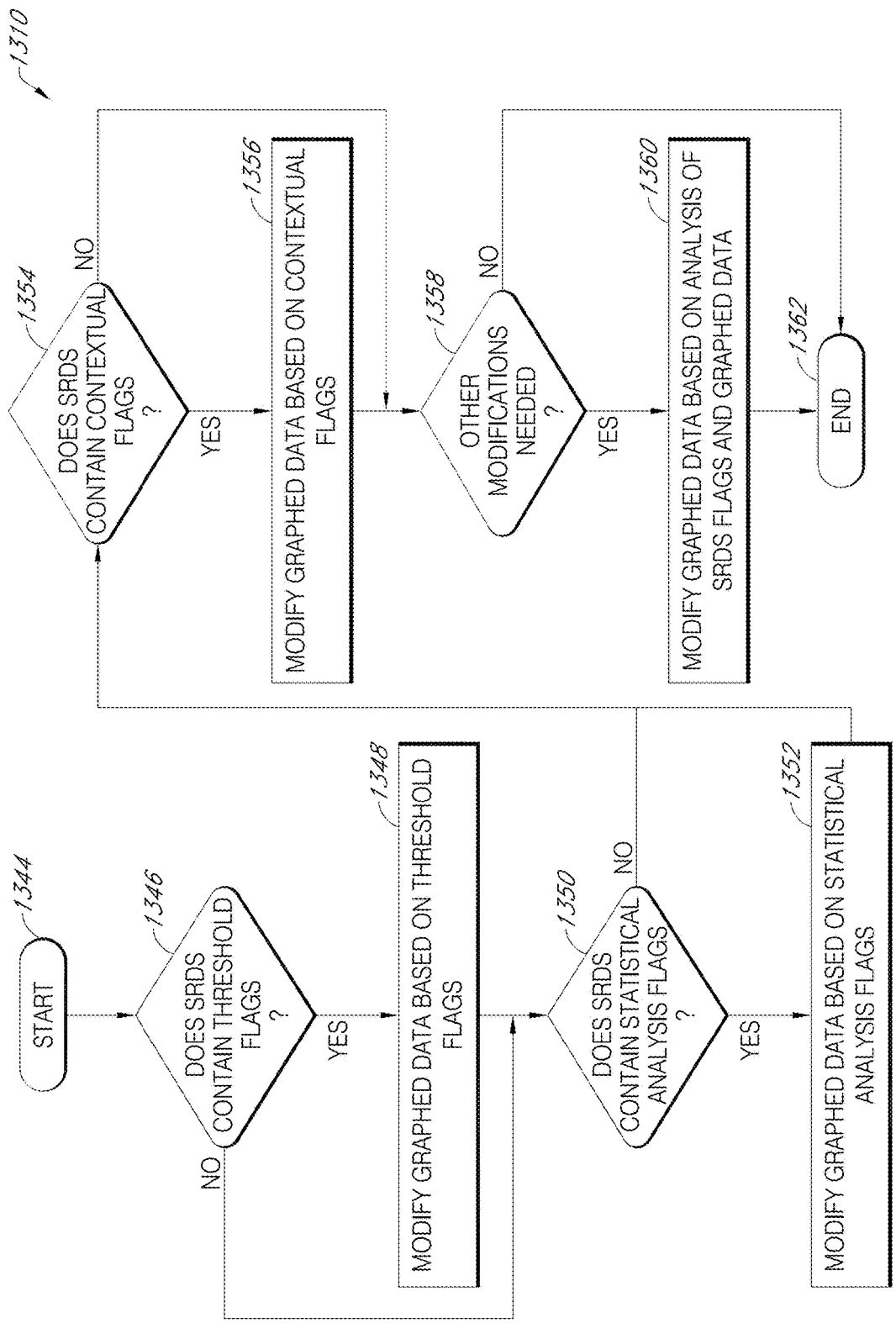
FIG. 13D illustrates a flow chart of an exemplary method to implement a process identified in the process of FIG. 13A.

FIG. 13D illustrates a flow chart 1310 of an exemplary method to implement the process identified in the block 1310 of FIG. 13A to modify the graphic to indicate one or more features in the analyte concentration values. While this exemplary method is described where the processor 335 of the display device 310 implements the method, it is understood that other devices of the system can be configured to implement the method. Depending on the graphical display chosen by the user, the processor 335 can modify the graphic produced by the process 1308 to indicate one or more features and/or patterns in the analyte data. Additionally, the modified graphic can present data in a form that reduces information overload and possible user's misinterpretation of the presented data. For example, if the user choses a three dimensional graph, for example the graphical display 400A, certain portions of the graphed analyte data can block other portions of the graphed data. The process 1310 can detect such instances and modify the graphed data accordingly, for example, by making portions of the graphed analyte data transparent in the overlapping regions.

The process 1310 can use color to modify the graphic generated by the process 1308. For example, the process 1310 can add various shades of color to the graphed analyte data in relation to one or more sets of high and low thresholds. The process 1310 can utilize the flagging or additional embedded information obtained at the block 1320 of the process 1306 to color-code the graphed data. For example, the processor 335 can detect portions of the graphed data corresponding to the analyte values which are 20%-30% above a high threshold. The color yellow or a shade can be used to modify the graphed analyte data to indicate these values. If the graphed analyte data in another portion is 40%-50% above the high threshold, a contrasting shade (e.g., a darker shade of a gray gradient or a darker shade of the color yellow if color is used) can be used to indicate that portion of the analyte data. The processor 335 can consult the flags or embedded additional data in the self-referential dataset to detect and modify the portions of the graphed data relative to the high and low thresholds.

In some examples, the process 1310 can utilize the statistical analysis obtained at the block 1322 of the process 1306 to modify the graphic produced by the process 1308. For example, the self-referential dataset (SRDS) can include flags or embedded data indicating which analyte values fall outside of an acceptable multiplier of the standard deviation of the analyte data or which analyte values are statistically unreliable. The processor 335 can modify the graphed data based on statistically derived flags in the SRDS.

In some implementations, the SRDS can include flags or embedded information based on the context of analyte data. The context of the analyte data can be obtained or derived from variety of sources. For example, if analyte values obtained on a particular day of the week coincide with the mobile display device 310 being detected at a restaurant, the SRDS can include flags or embedded information indicating this correlation. The frequency of the detected correlations between the analyte data and the context of the data can also be included in the SRDS. The processor 335 can modify the graphed data to include features according to the context-based flags found in the SRDS to visually indicate patterns of user's behavior in relation to the analyte data over a period time. The user can make health or diabetes related decisions in part based on the modified graphed analyte data and the features described therein.

In some implementations, the processor 335 can modify the graphed data where the modification is based on detecting a pattern of the flags or embedded information in the SRDS. For example, the SRDS can include flags indicating peaks and valleys of the analyte data. The processor 335 can detect that in a two-dimensional graph, with numerous concentrated peaks, different sections of the graphed analyte data can visually merge together and make the identification of these peaks difficult for a viewer. In such instances, the processor 335 can increase or introduce a buffer zone between the various sections of the graphed analyte data to remedy this scenario. The processor 335 can consult the flags or additional embedded data in the SRDS to detect peaks and valleys of the data and determine whether patterns exist where the peaks are graphed too close together, such that modifying the graphed data to include a new or increased buffer zone can aid in convenient visual interpretation of the graphed data.

The process 1310 begins at the block 1344. The process 1310 then proceeds to a series of decisions followed by modifications of the graphed data to indicate features in the analyte data. For example, the modification of the graphic to indicate one or more features in the analyte concentration values can modify the graphed data to indicate one or more patterns of the analyte concentration values. Persons with ordinary skill in the art will readily recognize that the present technology is not limited to the series of decisions and modifications disclosed herein and additional series of decisions and modifications can be devised and implemented without departure from the spirit of the present technology. Nor are all the disclosed decisions and modification steps required in every implementation. Depending on the user's desired graphical display, one or more decisions and modification steps may be eliminated or other ones added.

At the decision block 1346, the processor 335 scans the SRDS to detect whether flags or embedded additional data related to the relationship between the analyte data and one or more high and low thresholds exist. A variety of such flags or additionally embedded information may be included in the SRDS. For example, analyte data in the SRDS can be flagged or correlated with threshold values where different time scales within the analyte values of SRDS can have their own associated threshold values. The analyte data in the SRDS can be flagged based on the percentage or range by which the analyte data exceeds or falls below high or low thresholds. At block 1348, depending on the composition of the threshold flags and the type of graphic requested by the user, the processor 335 modifies the graphed data to indicate features and/or patterns in the analyte data.

In some implementations, the modification can include using colors, gradients of colors, shades, various degrees of transparency or opacity, varying the colors, gradients or transparencies based on overlapping and underlying regions to allow for visual detection of features and/or patterns in the analyte data as described above in relation to the modified graphical displays 400A, 400B, 500, 600, 700, 800, 900, 1000, 1100 and 1200.

At the block 1350, the processor 335 scans the SRDS to detect whether flags or embedded additional data related to the statistical analysis performed in the process 1306 exists within the SRDS. The processor 335 can modify the graphed data based on flags or embedded additional data in the SRDS, where the flags or embedded additional data are based on statistical analysis. For example, the analyte data in the SRDS can be flagged based on the relationship of the analyte data to standard deviation, mean, variance or other statistical parameters related to the underlying analyte data. In some implementations, the analyte data in the SRDS can be flagged if the analyte data falls outside of an acceptable multiplier of the standard deviation of the analyte data. A corresponding graphical modification of the graphed analyte data can be based on these flags. Or analyte data within two multipliers of the standard deviation of analyte data can be flagged to later modify the graphed data with a color.

If the SRDS contains statistically-based flags or embedded information and their corresponding graphical modification, at the block 1352, the processor 335 can modify the graphed data accordingly. In some implementations, the modification can include using colors, gradients of colors, shades, various degrees of transparency or opacity to allow for visual detection of features and/or patterns in the analyte data as described above in relation to the modified graphical displays 400A, 400B, 500, 600, 700, 800, 900, 1000, 1100 and 1200.

At block 1354, the processor 335 can scan the SRDS to detect whether flags or embedded additional data related to the context of analyte data exists. Some examples of context of analyte data can include, the contextual information related to the location of the user when the analyte data was collected (e.g. whether the user was at a restaurant, at the gym, at home or at work or school, the frequency at which the user appeared in this location), the relationship of the analyte data with various activities of the user (e.g. whether the analyte data was collected when the user had just taken a meal or had engaged in exercise, or was awake or asleep, whether and how much insulin was taken). The contextual analyte data can be obtained automatically without user intervention or can be inputted by the user.

The contextual analyte data is not limited to the examples enumerated herein and persons of ordinary skill in the art can readily determine other contextual analyte data which may be flagged, embedded or otherwise referenced in the SRDS. At block 1356, the processor 335 can modify the graphed data based on contextual flags or embedded data in the SRDS. Various graphical modifications corresponding to various contexts can be programmed in the process 1310. Contextual modifications can include using colors, gradients of colors, shades, various degrees of transparency or opacity to allow for visual detection of features and/or patterns in the analyte data as described above in relation to the modified graphical displays 400A, 400B, 500, 600, 700, 800, 900, 1000, 1100 and 1200.

The graphical modifications of the process 1310 are not limited by the examples enumerated above. Variety of graphics can be used for modification to indicate features, patterns or trends in the analyte data and conveniently alert or convey health or diabetes related data to a user. The processor 335 can use graphics or graphical techniques such as graphical icons, animations, texts or text boxes, fonts and stylized texts or numbers, arrows, gradual fading or other techniques to modify the graphed data in the process 1310.

At block 1358, the processor 335 can scan the flags in the SRDS and the graphics produced by the process 1308 to determine whether other modifications to the graphed data can further improve readability, reduce clutter and better indicate features and/or patterns in the analyte data. For example, as described above, if the processor 335 detects numerous concentrated peaks in the graphed data and the associated flags in the SRDS, based on the type of graphed data, at block 1360, the processor 335 can modify the graphed data by introducing or adding one or more buffer zones to improve readability and to better indicate features and/or patterns in the analyte data. The processor 335 can also analyze the graphed data produced by the process 1308 and the flagged data in the SRDS to detect if overlapping regions are rendered in a manner that the conveyance of information in the graphed data is reduced. At block 1360, the processor 335 can modify colors, shades, gradients, spacing or transparency in the overlapping regions to visually distinguish the overlapping regions and improve the graphed data's ability to convey features, patterns or trends in the analyte data. Persons of ordinary skill in the art can readily determine additional analysis of flags and the graphed data and their associated modifications in order to improve conveyance of health or diabetes related data. The process 1310 ends at the block 1362 and further processing is handed over to the block 1312 of FIG. 13A.

Although in some implementations, the processes of generating the SRDS, the graphed data and the modified graphed data are described in relation to past or collected analyte data, the systems and methods of the present technology can be used with future or predicated analyte data or a combination of past, collected and future analyte data.

Insulin Visualization

The embodiments described herein are not limited to generating data structures based on analyte data. Raw data on other compounds relating to a patient's health can also be received and the system can generate data structures and arrangements of data capable of producing modified graphical displays based on such data. For example, the system can receive data corresponding to a patient's insulin on board (JOB) level and generate data structures or arrangements of data capable of producing modified graphical displays to conveniently indicate useful information about the patient's health. The methods associated with FIGS. 13A-13D can be implemented to produce the modified graphical displays associated with insulin data.

Figure 14:
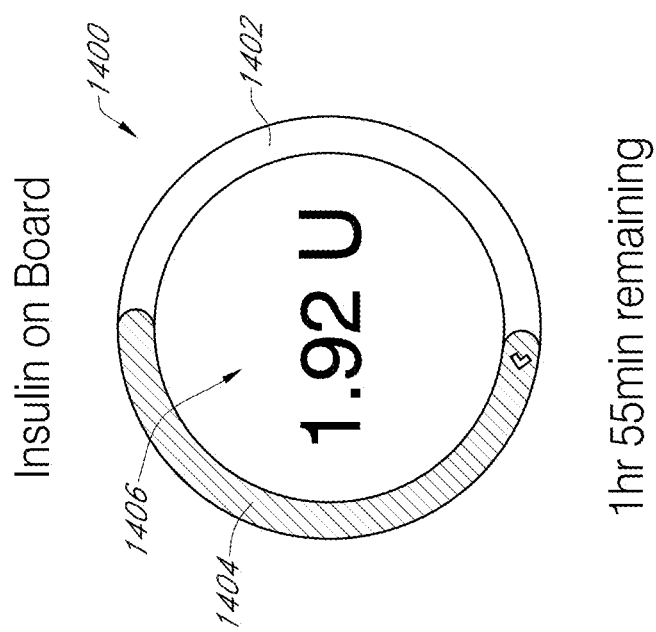
FIG. 14 is an illustration of a modified graphical display generated from data structures and arrangements of insulin data.

FIG. 14 is an illustration of a modified graphical display 1400 generated from the data structures and arrangements of insulin data. The display 1400 can include a ring 1402 where the full circle ring can represent a duration of insulin action (DIA). An overlay ring 1404 can represent the time remaining for the mount of insulin on board. The size of the overlay ring 1404 can be determined as a fraction of the full circle DIA. For example, if one hour remains of a four hour DIA, the remaining time would be ¼th of the total DIA. In this case, the overlay ring 1404 can overlay only ¼th of the ring 1402. When a user takes a dose of insulin, the overlay ring 1404 overlays the entire ring 1402. As time passes and insulin metabolizes, the overlay ring 1404 gradually reduces. In some embodiments, the ring 1402 and the overlay ring 1404 can be each rendered in different shades to better visually distinguish the two. In some embodiments, color is used to visually distinguish the two. A graphical representation 1406 corresponding to the time remaining can be shown in the center of the ring 1402. In some embodiments, the graphical representation 1406 includes a number representing the amount of insulin on board.

If the overlay ring 1404 is gradually reduced over a long period of time, the gradual reduction may be difficult to discern for some viewers. In some embodiments, when the graphical display 1400 is generated, the overlay ring 1404 is first shown to completely overlap the ring 1402 and the graphical representation 1406 is shown to correspond to the DIA. Over a short amount of time, the overlay ring 1404 is reduced quickly in size to correspond to the time remaining for a current amount of insulin on board. Over the same amount of time the graphical representation 1406 can be shown to reduce to settle at the current amount of insulin on board. For example, if numbers are used for the graphical display 1406, the numbers can reduce similar to a rapid counter counting down and settle at the current amount of insulin on board. Showing such a graphic for the overlay ring 1404 and the graphical representation 1406 over a short amount of time can aid a viewer to discern what information the graphical display 1400 conveys.

The SRDS generated based on insulin data can be flagged, according to some embodiments of the process 1306, to include appropriate triggers for animations, overlay graphs and textual information, as described above. In some implementations, when the graphical display 1400 is initiated, the processes 1308 and 1310 parse the SRDS for flags related to the generation of the graphic 1400 and modify the graphic produced by the process 1308 to generate the modified graphic 1400.

In some embodiments, the analyte sensor app 330 can be configured to receive events data, where events data can include information on a user's actions and activities related to health management or diabetes. For example, the events data can include: meals taken, exercise type, duration and intensity, and amount and type of insulin taken. The analyte sensor app 330 can be configured to generate data structures and arrangements of analyte data, which in turn can produce modified graphical displays capable of visually representing one or more relationships of the analyte data, insulin data and event data with each other and/or with or in relation to a time period. For example, based on visual constructs produced from the SRDS, a user of the system 302 can conveniently make health-related decisions, or detect features and/or patterns without excessive mental activity.

Figure 15:
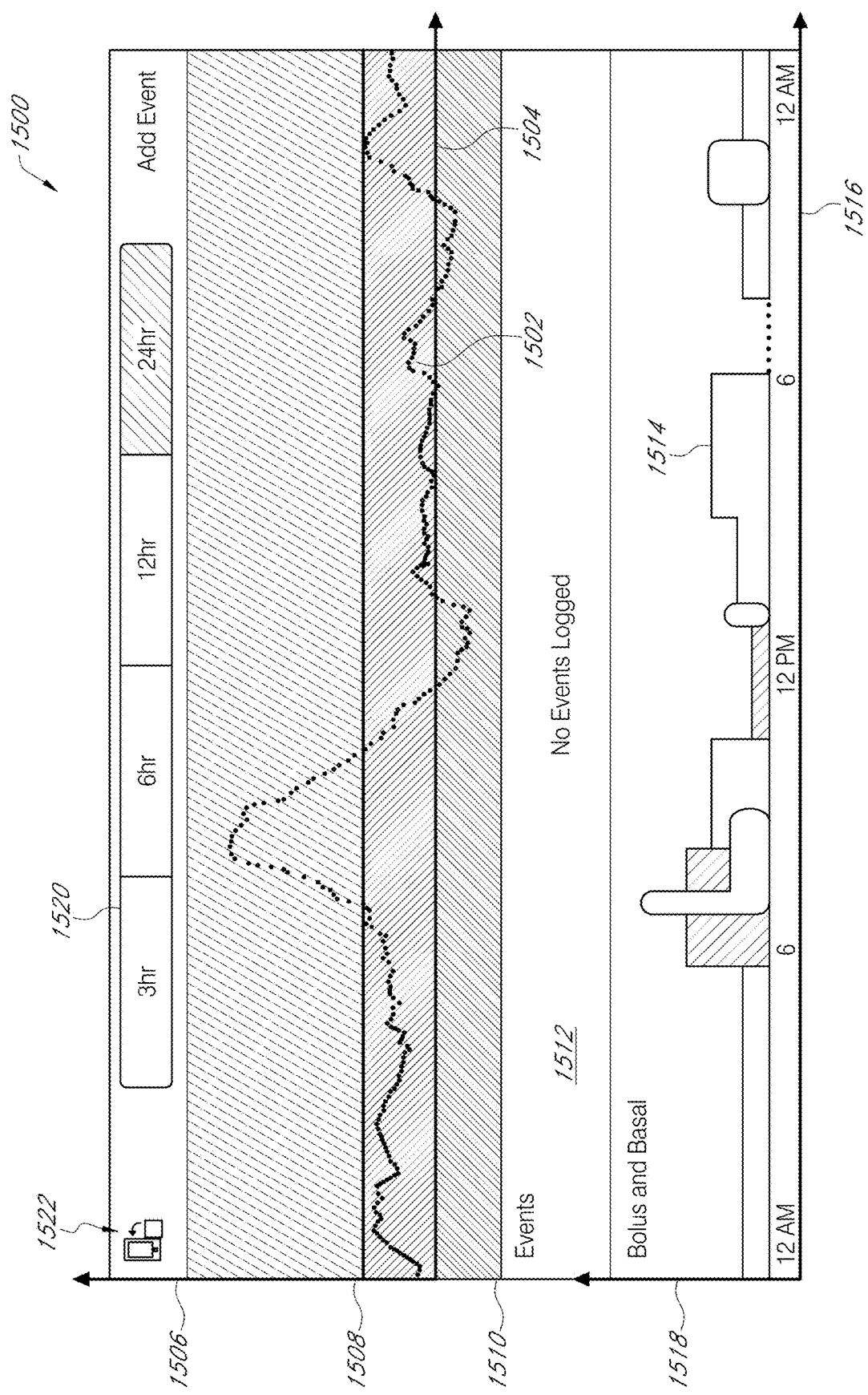
FIGS. 15 and 16 illustrate modified graphical displays which include visuals indicating one or more relationships of the insulin data, the analyte data and the event data with each other and/or with or in relation to a time period.
Figure 16:
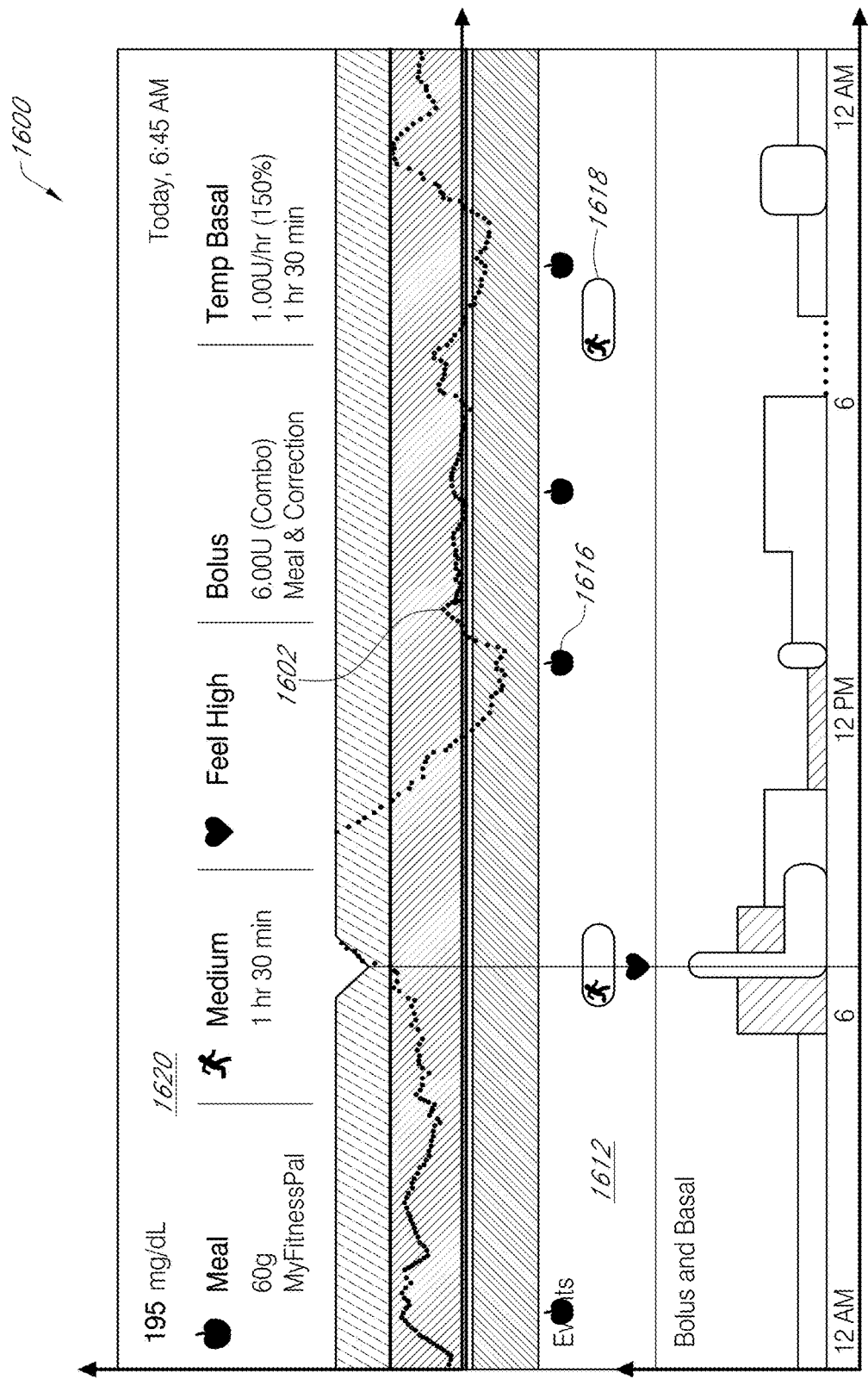

FIGS. 15 and 16 illustrate modified graphical displays 1500 and 1600 generated from the data structures and arrangements of data according to an embodiment where the graphical displays 1500 and 1600 include visuals indicating one or more relationships of the insulin data, the analyte data and the event data with each other and/or with or in relation to a time period. In various implementations of the modified graphical displays 1500 and 1600, the displays can include a display of one or more of insulin data, analyte data or the event data, wherein these displays can be modified to further display a visual indicating one or more relationships of the insulin data, the analyte data or the event data with each other or in relation to a time period. The visual can be shaped and configured or scaled such that the visual does not obscure the display of the insulin data, analyte data, or the event data. Furthermore, the visual can be displayed in its entirety within the display of the insulin data, the glucose data or the event data.

The graphical display 1500 can include an analyte trend graph 1502. On a horizontal axis 1504, time is represented. On a vertical axis 1506, the magnitude of analyte data is represented. The analyte trend graph 1502 can be represented in relation to high and low thresholds 1508 and 1510. While not all embodiments are shown, the analyte trend graph 1502 can be rendered in various colors, line styles or shades in relation to the high and low thresholds 1508 and 1510 to visually indicate the relationship between the analyte data and the high and low thresholds 1508 and 1510. The graphical display 1500 can additionally include an event data display area 1512. In the example of FIG. 15, no event data is shown in the event data display area 1512, but could be presented there. Examples of event data are shown later in FIG. 16, where various icons and graphical displays are shown in the event data display area 1612. Referring back to FIG. 15, the graphical display 1500 can additionally include a graph of insulin data 1514. A horizontal axis 1516 can represent time. A vertical axis 1518 can represent the magnitude of the insulin data. A user can expand or contract the time period in which the analyte trend graph 1502 and insulin graph 1514 are displayed via different time period tabs 1520. A graphical display or icon 1522 can indicate to the user that by changing the orientation of the mobile computing device from portrait to landscape or vice versa, the user can obtain different visuals of the relationships between the analyte data, the insulin data, event data and time. The event display area 1512 can include: a display of a graphical arrangement of the event data including one or more of an amount of carbohydrate intake, an amount of time spent exercising, an amount of calories burned, or a heart rate level reaching a threshold or time associated thereof.

Referring to FIG. 16, the graphical display 1600 is similar to the graphical display 1500. The event data display area 1612 can allow a user to easily access indicators of when the user took actions that may be considered relevant to the management of the user's diabetes. For example, taking of a meal can be indicated with the label or graphical icon 1616 or an exercise session can be indicated by a label or graphical icon 1618. The event display area 1612 can be generated and shown to the patient's caregivers for quick access to patient's actions relevant to management of diabetes. In some implementations, the user can be presented with an array of graphical icons of potential actions relevant to the management of diabetes and the user can drag and drop them onto the analyte trend graph 1602 or event display area 1612 to indicate when the user has taken those actions. For example, the user can drag a meal event graphical icon 1616 and drop that icon on the analyte trend graph 1602 around 12 p.m. The event display area 1612 can be subsequently updated to show the graphical icon 1616 corresponding to the user having taken a meal around 12 p.m. Similarly, the user can add an exercise icon around 6:30 p.m. In some embodiments, the user can also input event information via voice recognition, or keyboard entry and the event display area 1612 can automatically update based on the user's input showing relevant icons such as the meal icon 1616 and the exercise icon 1618.

The user can also utilize a pointing device, or a touch screen to point to or touch a point on the analyte trend graph 1602 and activate a callout window 1620. The callout window 1620 can include more details related to the event data displayed in the event data display area 1612. The callout window 1620 can, for example, include a timestamp, type or amount of meals the user has taken, type, intensity and duration of any exercise the user has performed, some indication of the general feelings of the user, and types and amounts of insulin the user has taken. The call-out window 1620 can include a graphical arrangement of the insulin data, for example: insulin data including one or more of a bolus or basal amount of insulin, a dosing time of a bolus insulin, a dosing time of basal insulin, or an insulin on board value.

Figure 17:
FIG. 17 illustrates an insulin key chart of the FIGS. 15 and 16.
Figure 17:
Figure 17:
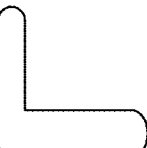
Figure 17:
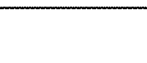

Some implementations of the graphical displays 1500 or 1600 can include a chart key. FIG. 17 illustrates an example of an insulin chart key 1700, which can optionally be generated and displayed along with the graphical displays 1500 or 1600. The chart key 1700 can include graphical displays 1702, 1704, 1706, 1708 and 1710 corresponding to different types of insulin a user can take; these, for example, can include: temp basal, bolus, extended bolus, combo bolus, and basal, respectively.

Figure 18:
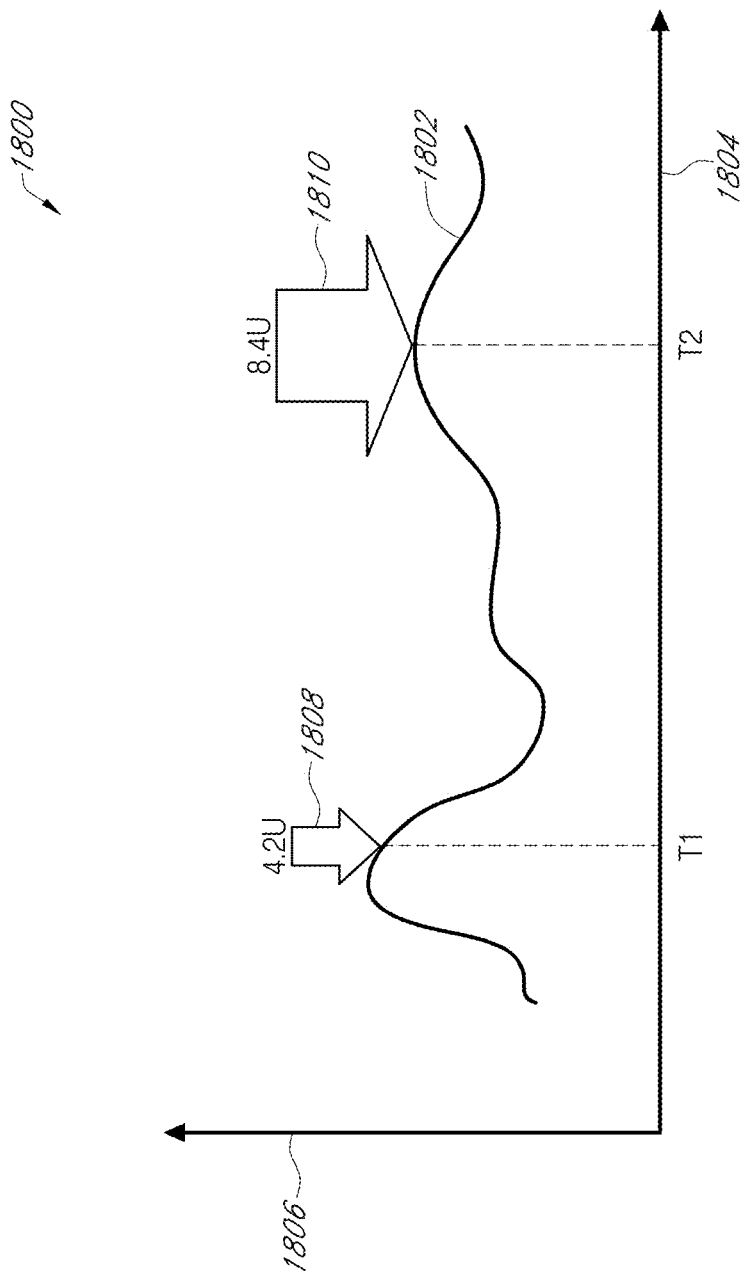
FIG. 18 illustrates a modified graphical display of a trend graph of analyte data.

FIG. 18 illustrates modified graphical display 1800 generated from the data structures and arrangements of data according to an embodiment where the graphical display 1800 includes visuals indicating one or more relationships of the insulin data and the analyte data. The modified graphical display 1800 can include an analyte trend graph 1802. On a horizontal axis 1804 time is represented. On a vertical axis 1806 the magnitude of the analyte data is represented. One or more amounts of insulin on board (JOB) data can be represented above or on the analyte trend graph 1802 by utilizing one or more arrows 1808 and 1810, where the sizes of the arrows 1808 and 1810 correspond to the amount of insulin on board (JOB) to which each arrow refers. Optionally, one or more numerical representation of the amounts of insulin on board (JOB), for example as text, can be displayed on or above the arrows 1808 and 1810.

In an illustrative example of use of the modified graphical display 1800, the data set construct can be formed to allow intuitive visualization of the meaning or effects of the IOB data it includes and displays. For example, instead of just a number, the insulin on board is visualized as a down arrow above the glucose trend chart. This could be intuitive because, physiologically, it is understood that insulin pushes down on glucose. The more insulin on board, the larger the arrow (the more force pushing down). The number of units could optionally be also displayed with the arrow. In an example use case where a user ate a meal and took insulin, it could be a useful reminder that the user may not necessarily need to dose more insulin again because the insulin hasn't acted, which could in turn prevent insulin stacking. In the opposite use case, for example, if the user forgot to take insulin, the absence of an arrow (or a small arrow) could be a reminder that they forgot.

Algorithm Visualization and Decision Support

Diabetes can be a complex disease where patients find themselves having to make frequent treatment decisions at all times. As such, the mental demands and stresses of managing diabetes can be taxing on the patients. The system 302 can utilize the available data to present graphical displays that depict one or more relationships between the analyte data and past, current and future actions of the user to aid in analysis and health management of a patient.

Figure 19A:
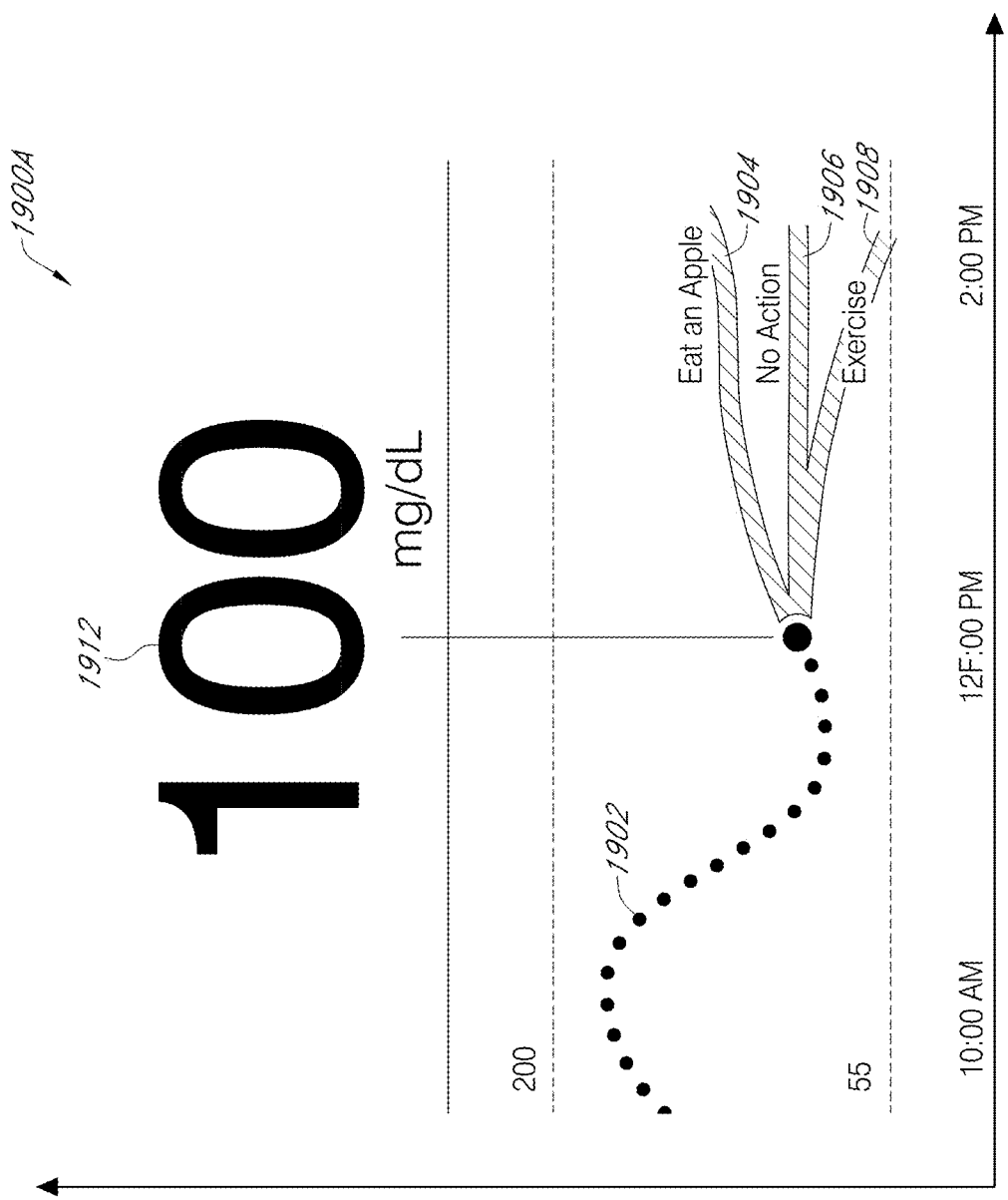
FIGS. 19A and 19B illustrate modified graphical displays based on historical, current and predicted analyte values.
Figure 19B:
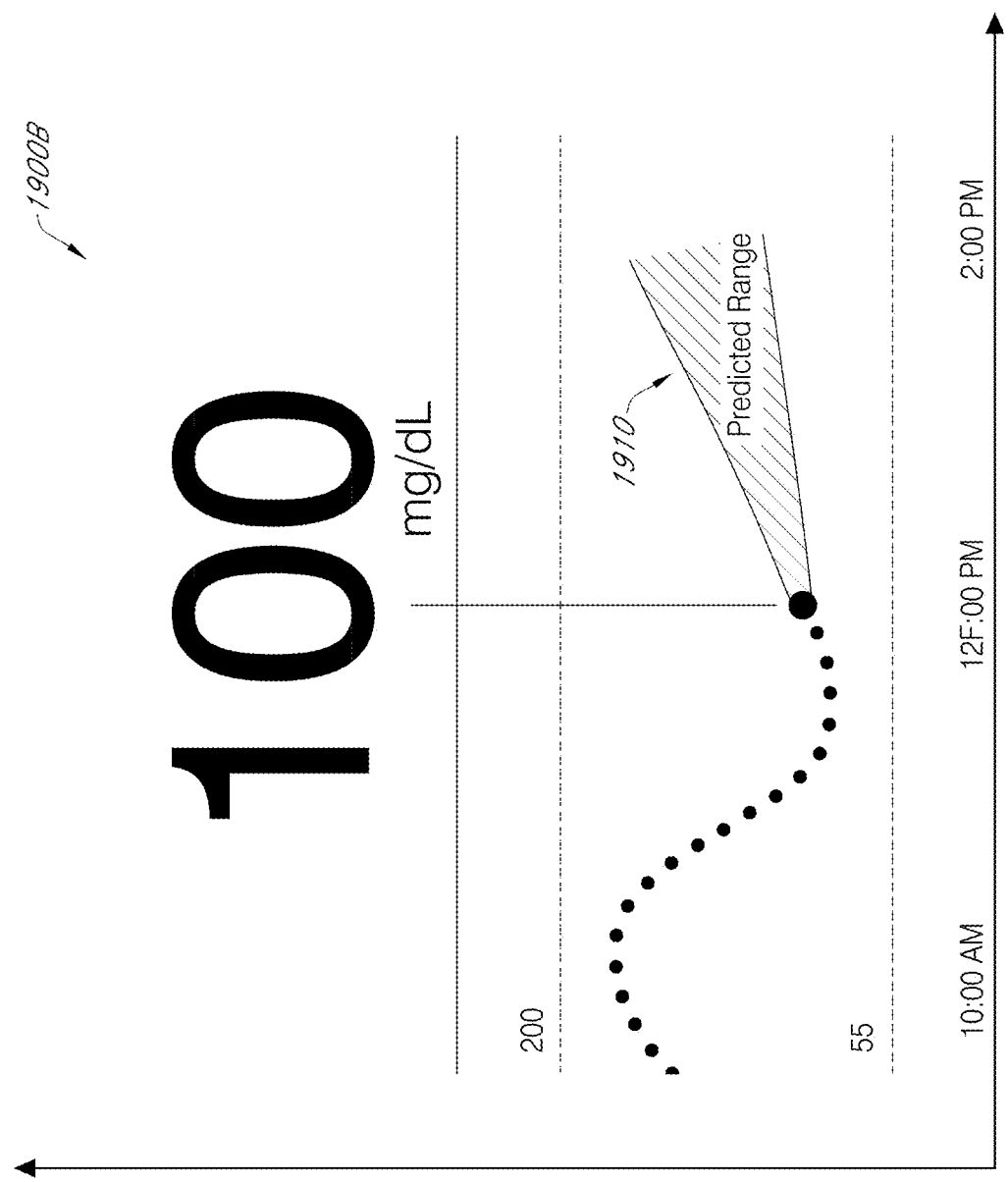

FIGS. 19A and 19B illustrate modified graphical displays 1900A and 1900B generated from the data structures and arrangements of data according to an embodiment where the graphical displays 1900A and 1900B include visuals indicating one or more relationships of the insulin data and the analyte data based on historical, current and predicted analyte values. The modified graphical display 1900A can include analyte trend graph 1902. On a horizontal axis time is represented and on a vertical axis the magnitude of the analyte data is represented. The graphical display 1900A can include a current value of the analyte data 1912. The graphical display 1900A can be an action-based prediction trend graph and can include one or more prediction graph lines 1904, 1906 and 1908 based on the user's actions. These actions can include, for example, eating, exercising or taking no action. The prediction graph lines 1904, 1906 and 1908 can be based on actions the user has already taken or can be based on actions the user is considering. Alternatively, the prediction can be depicted as a range 1910 as illustrated in the graphical display 1900B. Depending on one or more reliability parameters, underlying prediction algorithms, the graphical displays 1900A and 1900B can be displayed as general range predictions similar to hurricane estimated path visualization or the graphical displays 1900A and 1900B can be displayed as single or multiple lines. The graphical displays 1900A and 1900B can be modified according to the process 1310, as described above based on flags in the SRDS corresponding to parameters related to the certainty or reliability of predictions. The modifications can include fading out the predicted range where one or more certainty parameters deteriorate. The graphical display of the predictions can visually convey the relationship between a user's actions and their likely effect on the analyte data thereby relieving the patient's stress in making treatment decisions.

Figure 20:
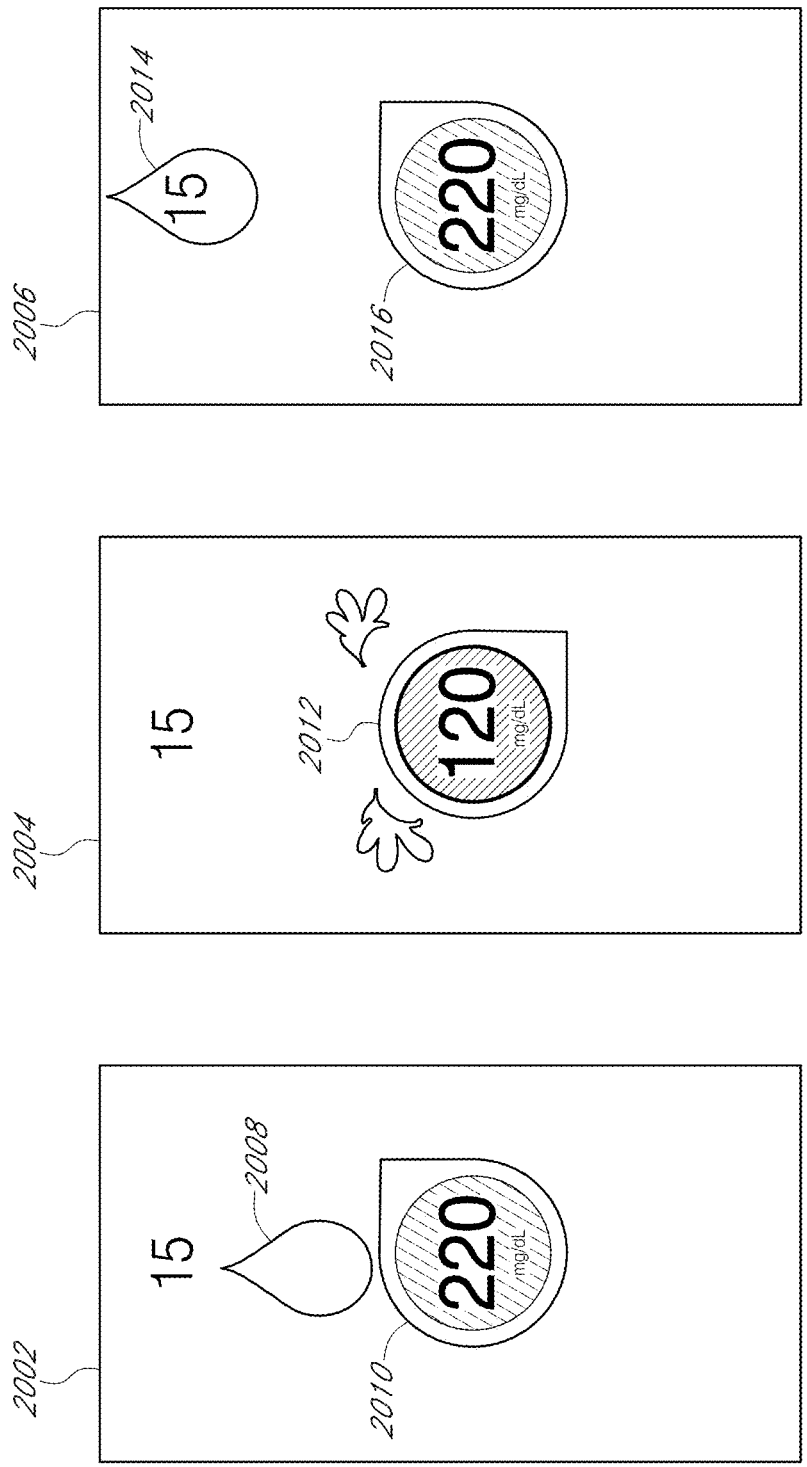
FIG. 20 illustrates a modified graphical display where effect of an insulin dose on analyte data is shown.

In another implementation, a predictive bolus calculator can be used to visually inform the user of the effect of administrating bolus on the future trend of analyte values in the host. FIG. 20 can include modified graphical displays 2002, 2004 and 2006, where an amount of recommended (or intended) bolus is represented by a graphical display 2008. A graphical display 2010 can depict a current value of the analyte data and an indication of a future trend of the analyte data. Through a user interaction with the graphical display 2008 or by an initiating action of the system 302, the graphical displays 2008 and 2010 can interact. The graphical display 2010 can be modified based on the effect of the recommended (or intended) amount of bolus on the future trend of analyte values in a host. After the modification, the graphical display 2012 can depict the predicted trend of analyte values resulting from administration of the recommended (or intended) bolus. In the graphical display 2006, the graphical displays 2014 and 2016 can be restored to their previous shapes, 2008 and 2010, respectively.

Figure 21:
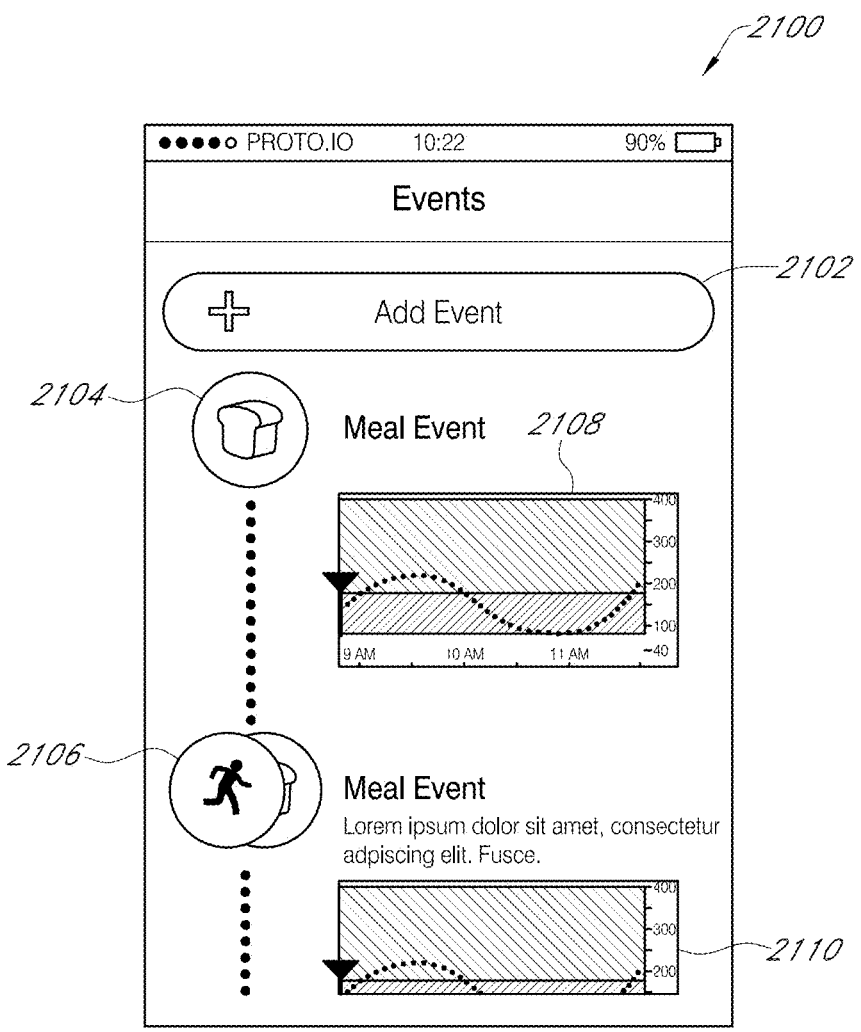
FIG. 21 illustrates a modified graphical display where a scrollable list of user's action data and future analyte value trends are depicted.

FIG. 21 illustrates a modified graphical display 2100 according to an embodiment where a scrollable list of user's action data and future analyte value trends are depicted. In some implementations, the user can be provided with a graphical interface module including a button 2102 to enable adding events (e.g. actions the user has taken including meals, bolus, exercise, stress, etc.). The system 302 can produce modified graphical displays such that for the current time or for a recent timeframe, a scrollable list view of the inputted events (e.g., Meal Event 2104 or Meal+Exercise Event 2106) and one or more snapshots of analyte trend values 2108 and 2110 for a time period after the event time, are displayed. The user can visualize the cause-and-effect relationship between their actions (inputted events) and their analyte levels. The user's clinical team can recognize patterns and react accordingly to better manage the user's health. Optionally, in some implementations, an algorithm could be used to infer or automatically suggest and/or link multiple events according to patterns of analyte data to determine one or more trends for future analyte data.

Figure 22:
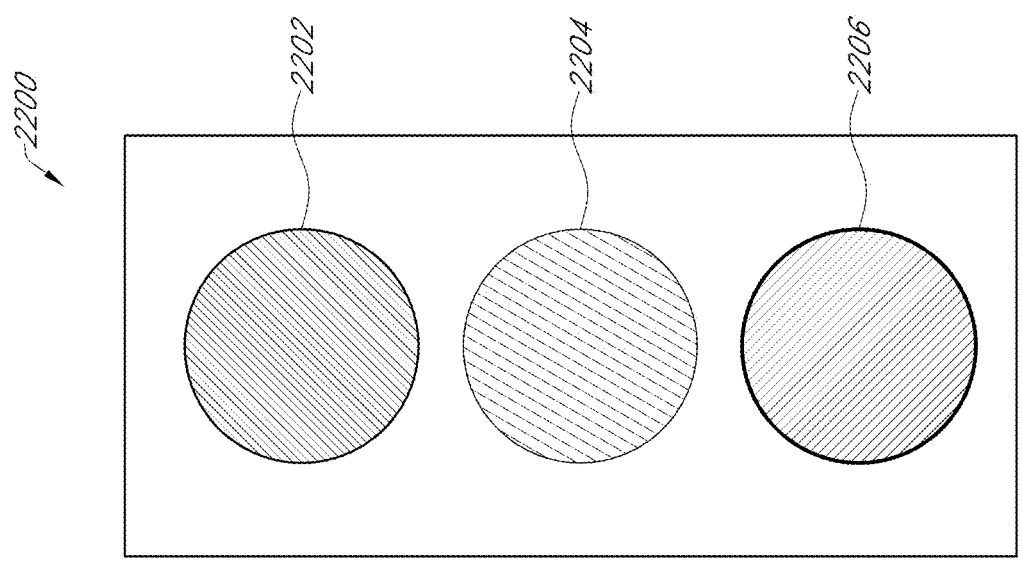
FIG. 22 illustrates a modified graphical display depicting a relationship between multiple variables related to analyte data trend and user actions.

FIG. 22 illustrates a modified graphical display which depicts a relationship between multitudes of complex variables in a simplified, display 2200. Diabetes patients often have to consider a multitude of complex variables and consider their relationship as they make decisions about their diabetes management. The modified graphical display 2200 simplifies the mental processes associated with analyzing the complex multitude of variables that inform a diabetes patient's decision making. In some implementations, the current analyte value can be compared against a high and low analyte threshold and an analyte score generated. The amount of insulin on board can be compared against a high and low insulin on board threshold and an IOB score generated. An insulin state score can be generated by multiplying the analyte score and the IOB score. In some implementations, other diabetes parameters can be analyzed and a score can be determined for each. The scores can become part of the insulin state score as additional multipliers. These diabetes parameter scores can, for example, include: an analyte trend score, GPS location based scores (e.g. bars or restaurants or physical locations where past data can indicate an influence of the location on the analyte values), food related scores, physical exercise scores and others.

The insulin state score can be ranked and categorized based on the ranked score. In some implementations, three categories of insulin state score can simply be good (indicating the patient is in a good state as far as diabetes parameters), caution (indicating the patient should proceed with caution and continue to monitor the diabetes parameters and make appropriate decisions) and bad (indicating a corrective action may be needed to remedy the situation). The display visual 2200 can include a visual behaving similar to a traffic light including three circles 2202, 2204 and 2206. Each circle can be filled with a distinct color, shading or gradient different than the other circles. Depending on the ranked insulin score, one of the shades in the traffic light 2200 can be depicted more prominently, similar to an operation of a traffic light. For example, the shading in the circle 2206 in the traffic light 2200 can indicate a good state, the shading in the circle 2204 in the traffic light 2200 can indicate caution and the shading in the circle 2202 in the traffic light 2200 can indicate a bad state.

In some implementations, a look-ahead module allows a user to selectively increase or decrease data related to current amounts or types of: insulin, exercise (intensity, type, etc.), food intake (composition, amounts, etc.), stress, illness, or other parameters affecting the health management of a diabetes patient and glucose values. For example, a user can use a sliding action on a touch screen or otherwise indicate increases or decreases in an inputted current or future event, activity or glucose related parameter and watch a projected effect on a glucose trend graph in real time. The predicted effects can be generated using a model based on a population of the patients and their glucose-related data and/or be based on machine learning over time for a specific user. The look-ahead module helps a user make better diabetes related decisions by observing predictions based on cumulative effects of a combination of factors on glucose values. For example, a patient can observe a current glucose value of 100 mg/dL and contemplating eating a snack, going for a run or taking a small dose of insulin. The look-ahead module would allow the user to play around with snack size/content, exercise type, duration or intensity and insulin dose type and size to find a desirable combination for proper glucose control. The look-ahead module can work in combination with other devices. For example, Time Travel on Apple Watch can trigger the predictions.

Figure 23:
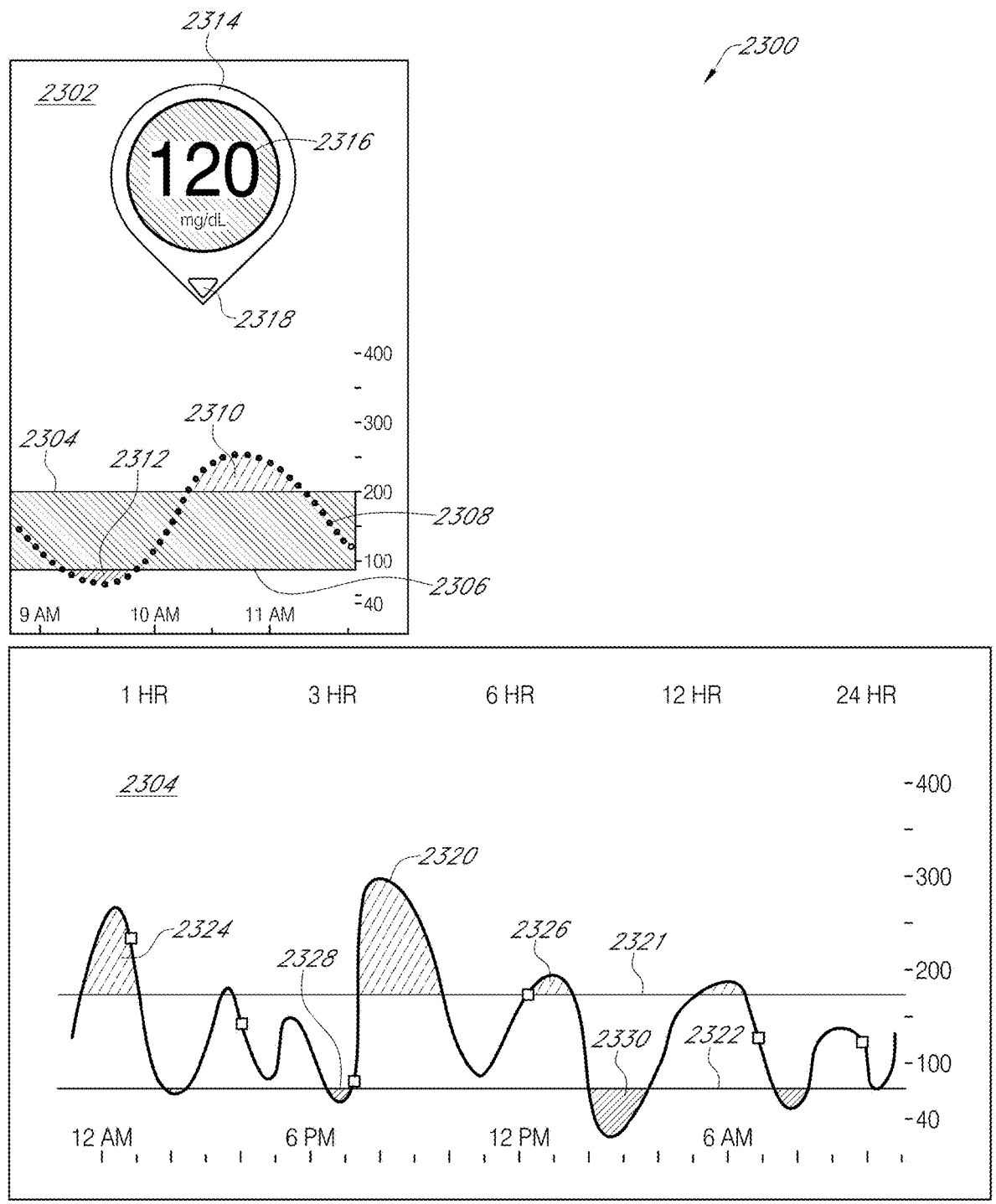
FIG. 23 illustrates glucose trend graphs were excursions outside of high and low thresholds are visually distinguished.

FIG. 23 illustrates an example of modified graphical displays 2300 providing efficiently information on a user's diabetes related data. FIG. 23 illustrates a glucose trend display 2302 were excursions outside of high and low thresholds 2304 and 2306 are visually distinguished by using one or more shaded areas 2310 and 2312 under the analyte trend curve 2308. Different shading, and if color is used, different colors, can be used to distinguish excursions above the high threshold 2304 and excursions below the low threshold 2306.

In some implementations, instead of or in addition to a trend graph of analyte values 2308, a simpler graphical representation of current and future analyte values 2314 can be depicted. For example, a numerical display of the current analyte value 2316 and a graphic 2318 of a prediction of the future trend in the analyte values can be depicted. In some implementations, the graphic 2314 can be in the shape of a tear drop. The graphic indicating the prediction can be a triangle 2318. The direction or the orientation of where the triangle 2318 is pointing can correspond to the prediction of future analyte values. For example, the triangle 2318 pointing sharply in an upward direction can indicate a prediction of an imminent rise in the concentration of analyte. The triangle 2318 pointing moderately in an upward direction can indicate a prediction of a moderate rise in the concentration of analyte. The triangle 2318 pointing in a horizontal direction can indicate predicting no significant changes in the concentration of analyte. The triangle 2318 pointing moderately downward can indicate a prediction of a moderate drop in the concentration of analyte. The triang1e2318 pointing sharply downward can indicate a prediction of significant or eminent drop in the concentration of analyte. Same or similar correlations between the direction of the triang1e2318 and the prediction of concentration of analyte can also be envisioned by one of ordinary skill in the art.

The analyte trend display 2304 can convey analyte concentration values over a 24 hour period or other time interval chosen by the user or automatically chosen by the system 302. A line graph of magnitude of analyte concentration values versus time can be utilized to generate analyte trend graph 2320. The trend graph 2320 can be depicted in relation to high threshold 2321 and low threshold 2322. Excursions above the high threshold 2321 can be depicted by shading the area under the curve between the trend graph 2320 and the high threshold line 2321. In the display 2304, examples of above threshold shading of area under the curve include areas 2324 and 2326. Excursions below the low threshold line 2322 can be depicted by shading the area under the curve between the trend graph 2320 and the low threshold line 2322. In the display 2304, examples of below threshold shading of area under the curve include areas 2328 and 2330.

Interactive UI Display

Some graphical displays depicting glucose, insulin, or diabetes related data can be too cluttered with scientific looking graphs and displays. The present technology envisions modified graphical displays which are friendly, uncluttered and easy-to-understand.

Figure 24A:
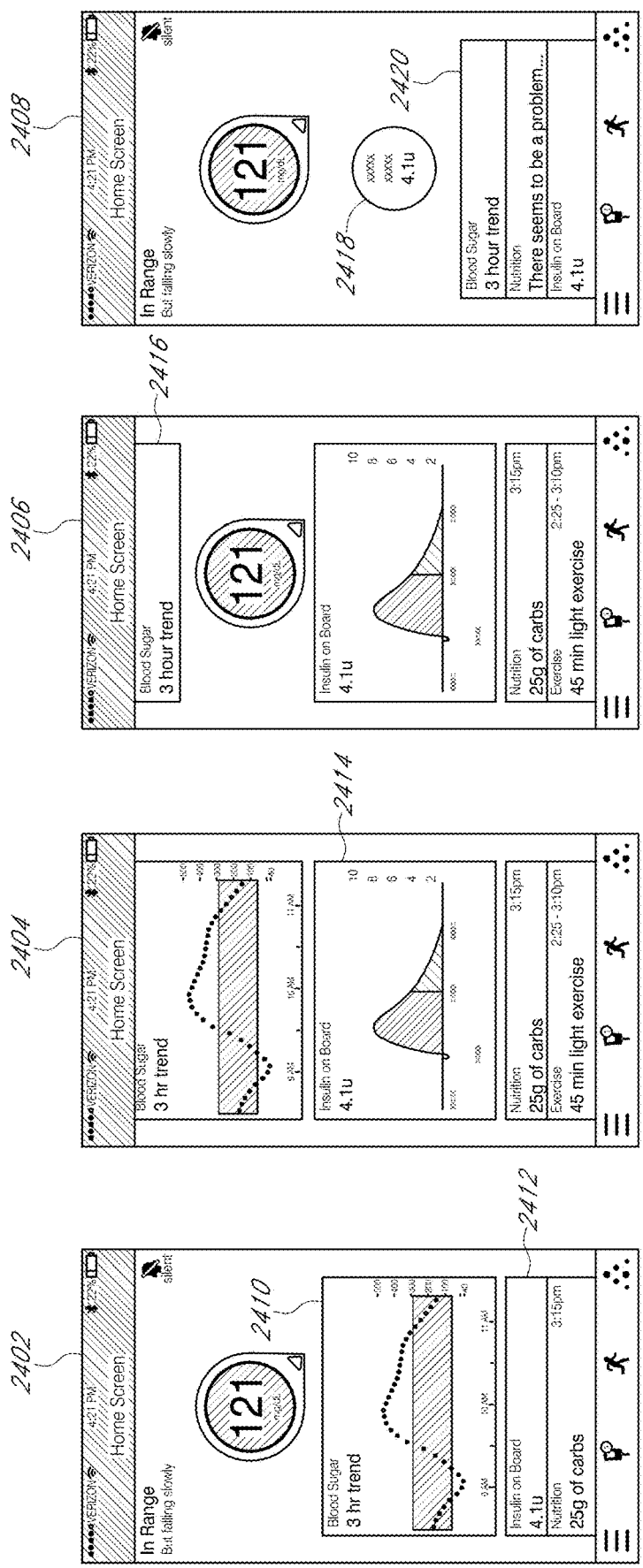
FIG. 24A illustrates modified graphical displays where a collapsible design layout is utilized.

FIG. 24A illustrates modified graphical displays where a collapsible design layout is utilized when the user desires to see more details. The user can view one or more modified graphical displays one at a time or at once if they wish. For example, the modified graphical display 2402 depicts a three-hour analyte trend graph 2410 in expanded view and IOB data 2412 in collapsed view. The user can click or touch the collapsed IOB view 2412 and obtain an expanded IOB view 2414 in the modified display 2404. The user can click or touch the expanded analyte trend graph 2410 and obtain a collapsed view 2416 in the modified display 2406 or the collapsed view 2420 in the modified display 2408. Some depictions of data can cycle through various display forms to depict the same data in multiple easy to understand format. For example, the user can click the expanded IOB view 2414 to obtain a different graphical representation 2418 of the IOB data as shown in the modified graphical display 2408. A subsequent user click or touch can collapse the IOB view 2418 back to the IOB view 2412 as shown in modified display 2402.

Figure 24B:
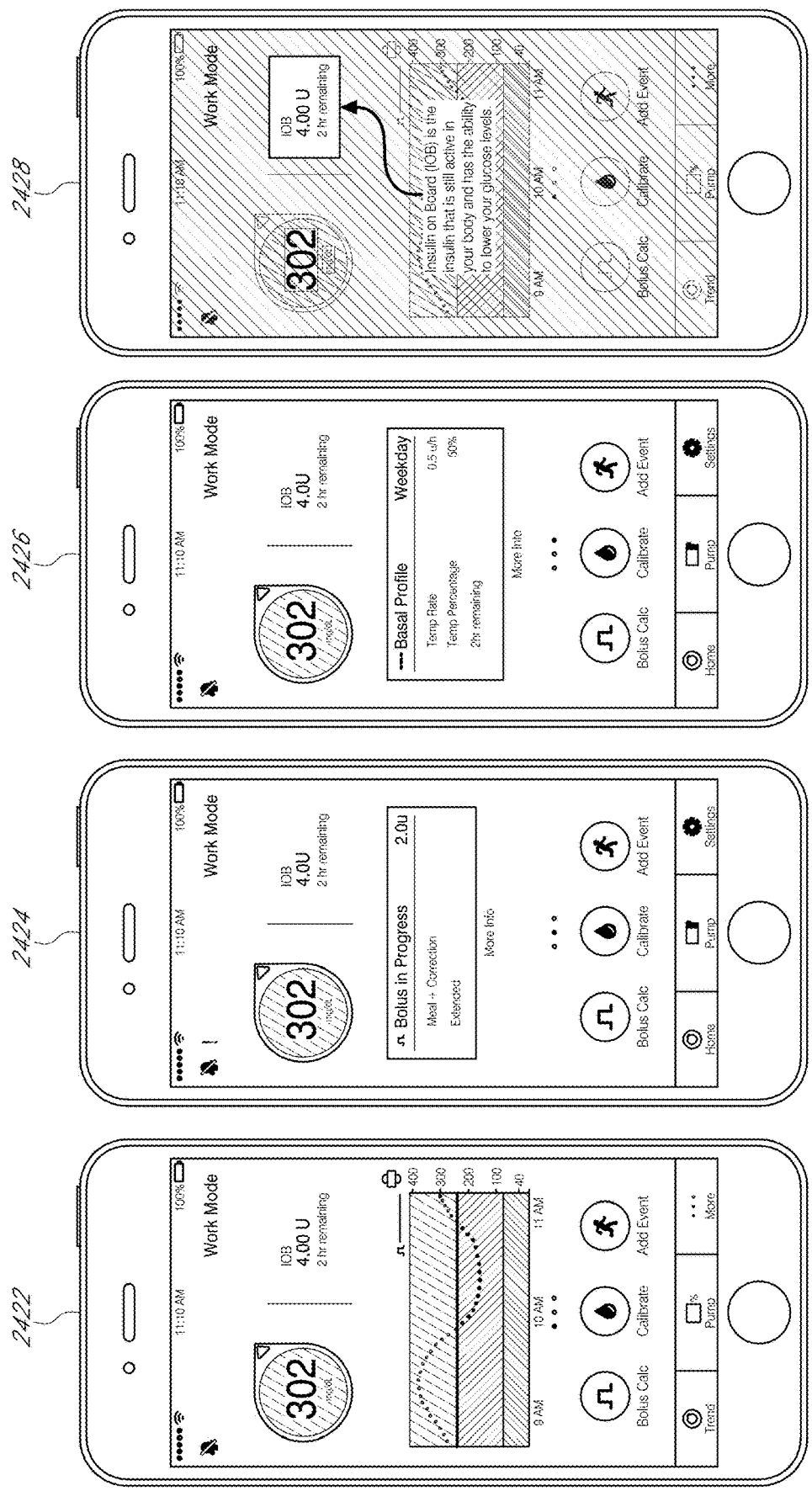
FIGS. 24B and 24C illustrate display screens presenting modifiable graphics based on user interaction with the display screen.
Figure 24C:
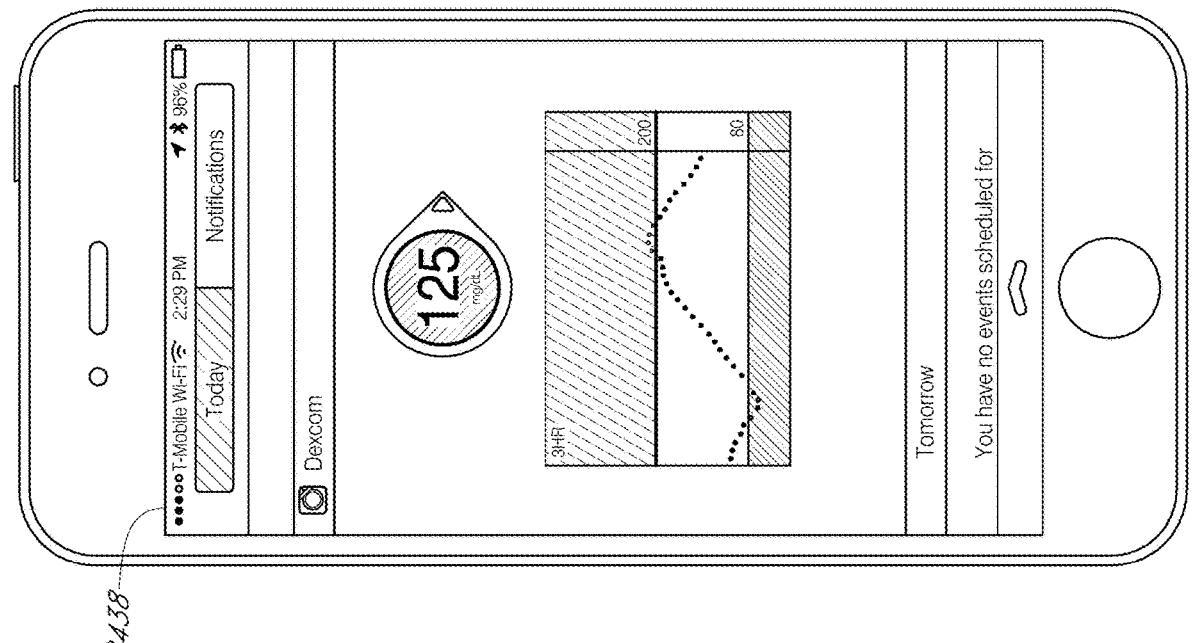
Figure 24C:
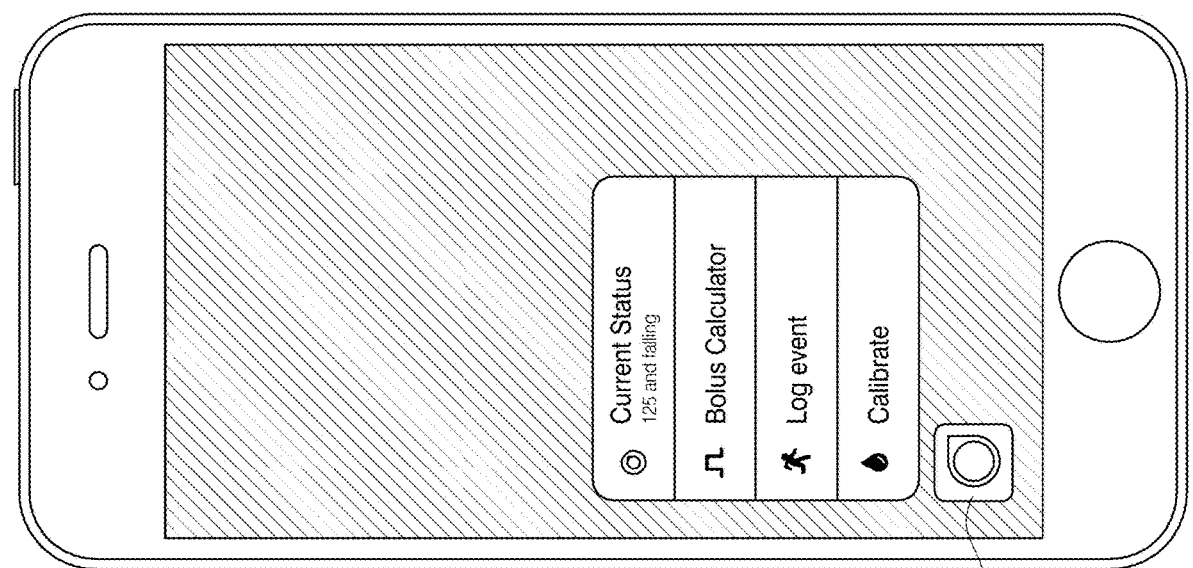

FIGS. 24B and 24C illustrate display screens presenting graphics that can be produced and modified in accordance with embodiments of the disclosed methods and systems. In the example shown in FIG. 24B, the display screens 2422, 2424, 2426 and 2428 include example graphic displays presenting current glucose 2430, a glucose trend graph 2434 or insulin on board 2432 information among other health related information. Features of the display 2422 allow user interaction to receive user input (e.g., through touch of a particular graphical feature of the display) and produce additional information based on the feature selected. For example, if the user were to select the IOB feature 2432, the display 2422 can be modified to produce the display 2428, where the display 2428 would present an enhanced view of the IOB data (e.g., in some implementations formatted differently, and/or in some implementations enlarged) with descriptive information about what insulin on board is and what it means, e.g., which can be in the context of the user's present glucose information. In the example shown in FIG. 24C, the display screens that include the graphic displays can be operable via the software application icon (e.g., icon 2436) and/or an event or notification display screen 2438 of the operating system of the mobile computing device.

Figure 25:
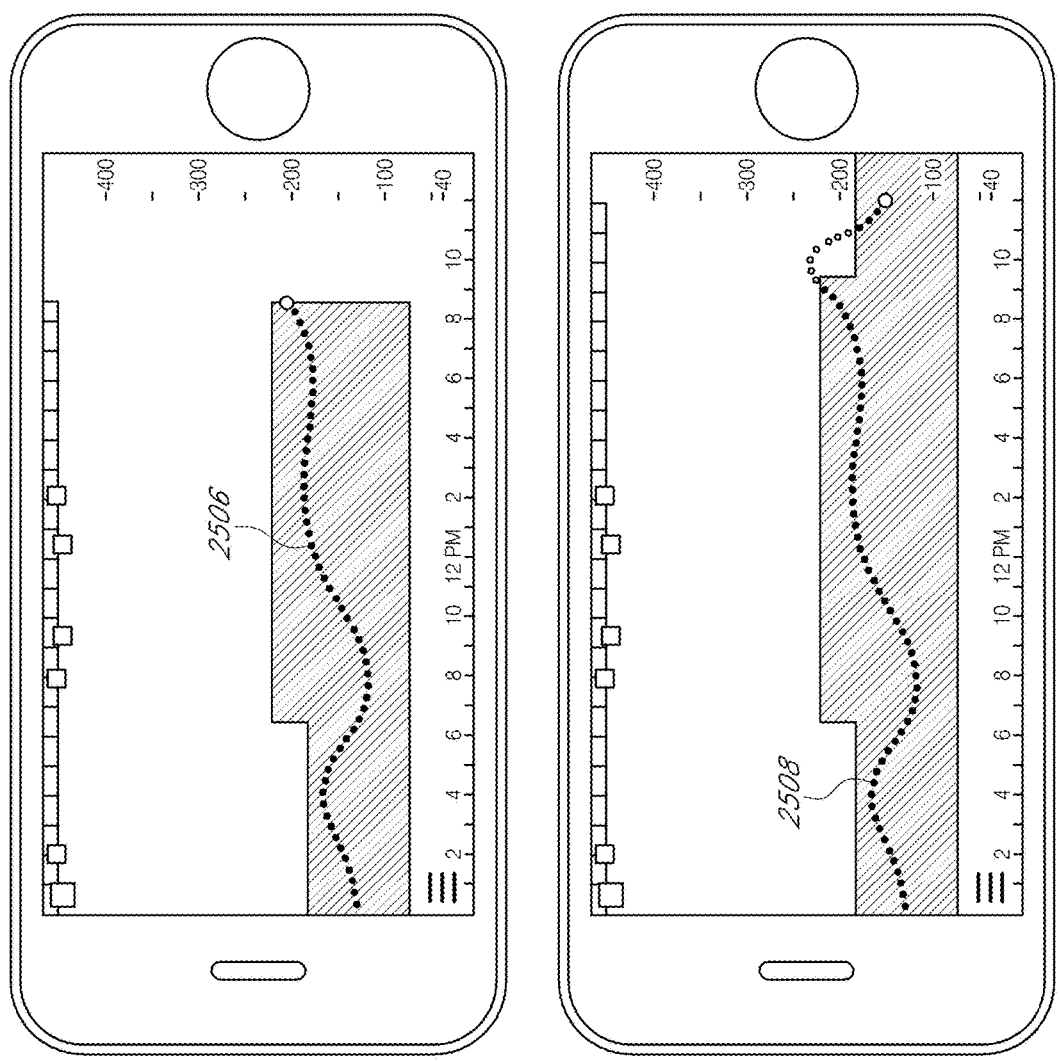
FIG. 25 illustrates modified graphical displays where animation can be used to convey health related information.
Figure 25:
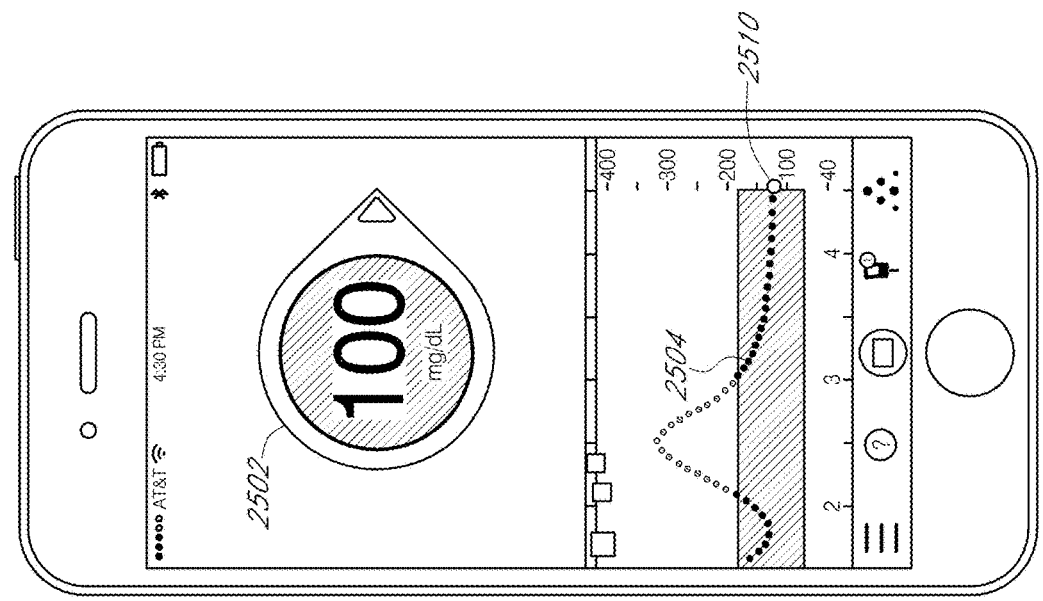

Modified graphical displays of the present technology can utilize animations to better convey information. In some implementations, various animations including pulsating and blinking can be used in combination with the graphical displays as described above. FIG. 25 illustrates modified graphical displays where animation can be used to convey health related information. Various rates and speeds of pulsating or blinking can be used to convey different information. For example, pulsating in the pattern of a heartbeat can indicate that the modified graphical display is depicting live data. Utilizing such animations can present the graphical displays in a more dynamic, alive and human-like light; thereby, eliminating or reducing the possibility of user error because of misinterpretation of the graphical displays. In some implementations, an arrow in a modified graphical display comprising a mag glass 2502 (numerical value of current glucose concentration value in a center of a circle with a small arrow in the perimeter of the circle pointing to the future trend of glucose values) can pulsate at different rates of speed to indicate information. For example, pulsating at a high rate can indicate urgency. In some implementations, the various points on the glucose trend graphs 2504, 2506 and 2508 can pulsate at different rates indicating additional information. For example, a most recent point 2510 on the trend graph 2504 can pulsate to indicate the current value. The pulsating can be different at different times of day, for example pulsating at a slower rate at night when the user is asleep. Modifying the graphical displays with animation can also reassure the user that the system is alive and the monitoring is current. Alternatively, a lack of animation can indicate to the user that the system is off-line, or the illustrated data may be stale.

Figure 26:
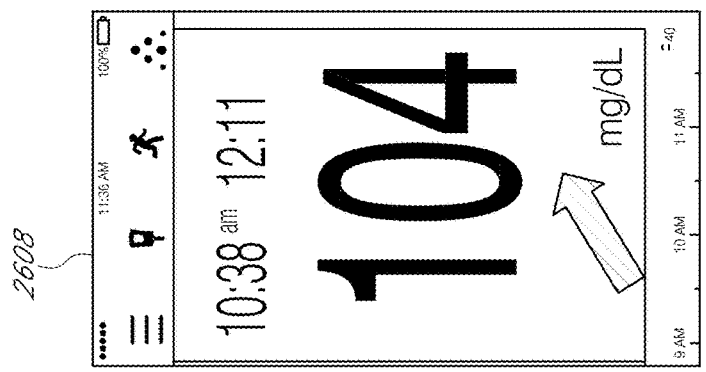
FIG. 26 illustrates a modified graphical display where a user can customize a background image.
Figure 26:
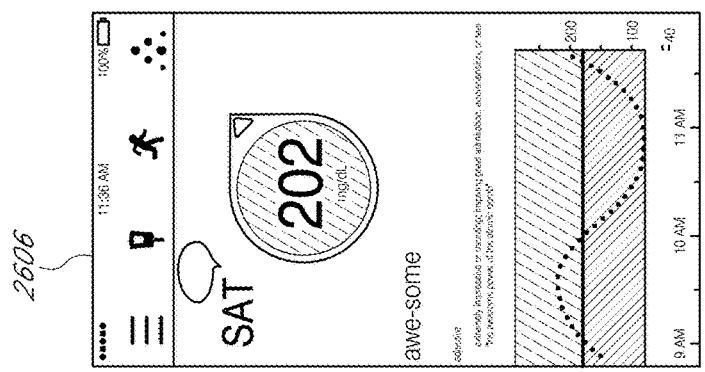
Figure 26:
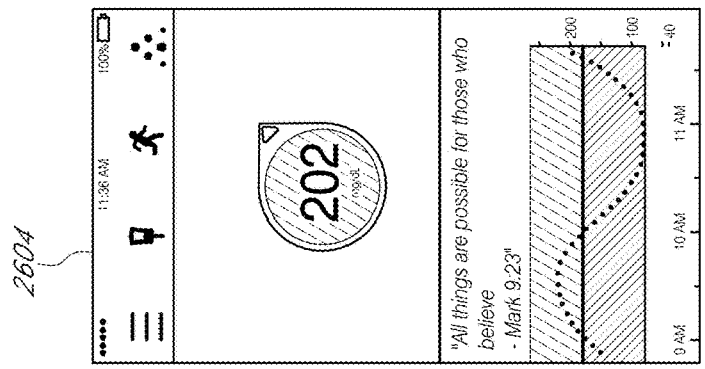
Figure 26:
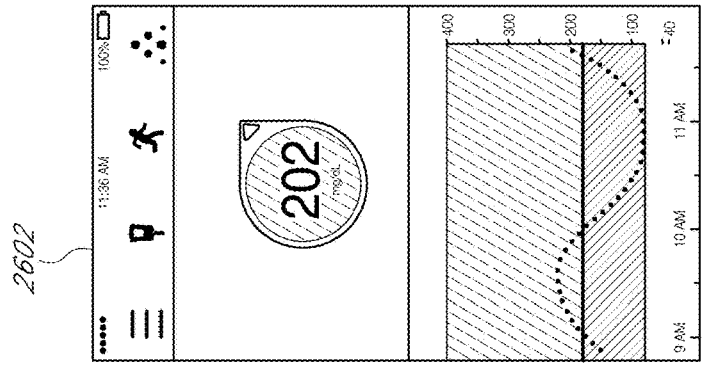

The user is more likely to interact with a modified graphical display with interest and attention if the modified graphical display includes personalized customization from the user. FIG. 26 illustrates modified graphical displays 2602, 2604, 2606 and 2608 where a user can customize a background image of one or more of the graphical displays to illustrate the health data of a user in the user's chosen theme. The background in display 2602 has been customized to a Star Wars® theme background. The background in the display 2604 has been customized to nature, religious or motivational theme. The background in the display 2606 has been modified to reflect or assist a study in the SAT exam. The background in the display 2608 has been customized to reflect a retro look and feel. The SRDS can be generated with the customized background image or other user customizations. When one or more of the graphical displays as described above are modified, the customized background image or the user's chosen theme can be incorporated into the modified graphical displays and presented to the user.

Figure 27:
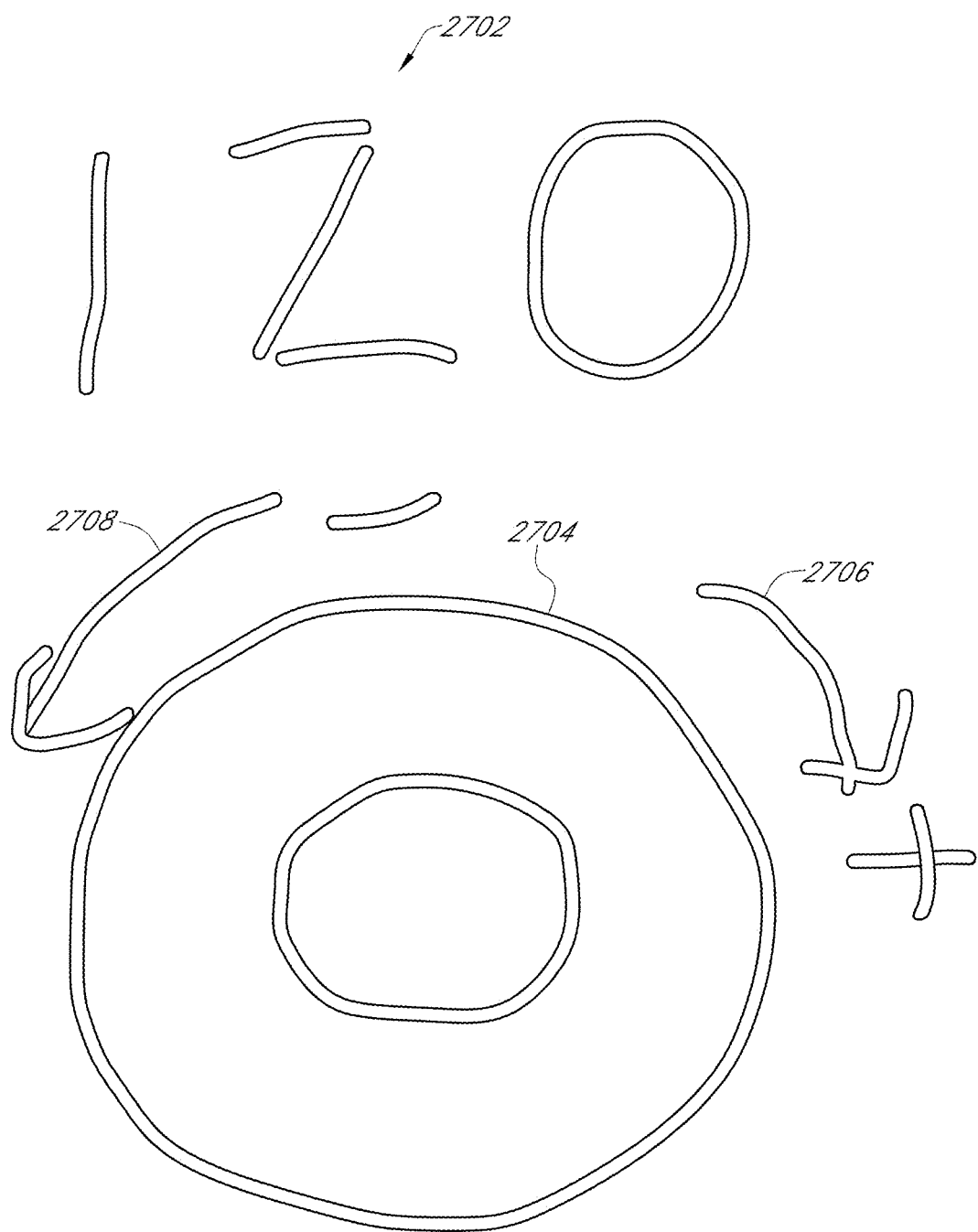
FIG. 27 illustrates a modified graphical display enabling a user to input numerical data using a scroll wheel.

To improve a user's ability to input data into the system, various graphical user input interfaces can be used. In some implementations, a graphic 2702 indicating a numerical keypad can be used. FIG. 27 illustrates a modified graphical display enabling a user to input numerical data into the system 302 using a scroll wheel 2704 and by hand gestures interacting with the scroll wheel 2704. The scroll wheel 2704 can be programmed to only cycle through numerical ranges that are acceptable. Moving one's fingers in a clockwise direction 2706 on the scroll wheel 2704 can increase the numerical values inputted, while moving one's fingers counterclockwise 2708 on the scroll wheel 2704 can decrease the numerical values inputted.

Figure 28:
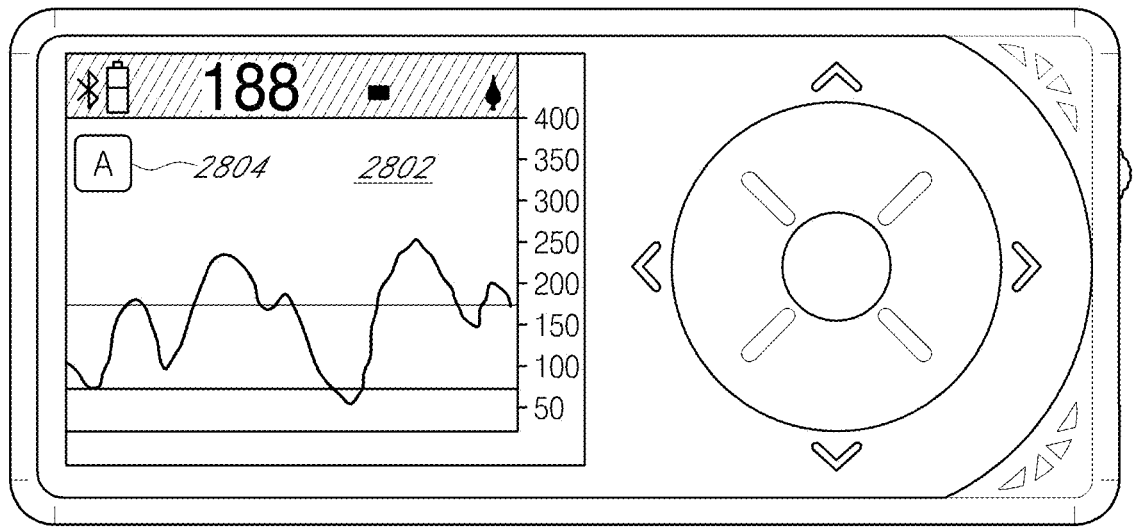
FIG. 28 illustrates an exemplary modified graphical display where a user's identifier is incorporated in the modified display.
Figure 28:
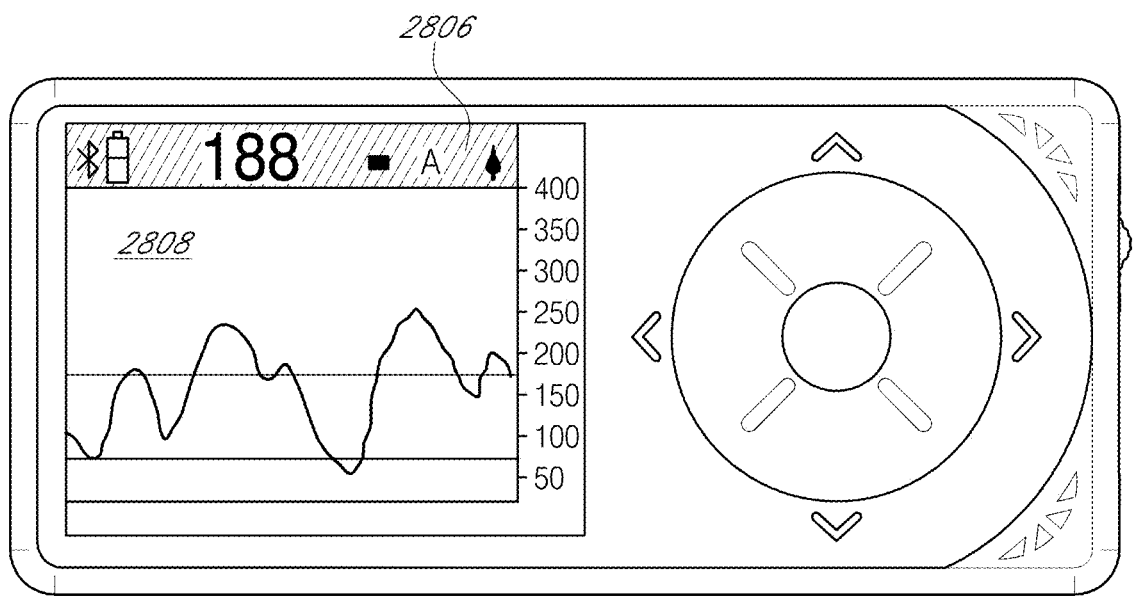

In households where multiple analyte sensor systems 308 or displays 310 are present, the users need to be able to identify their respective devices. Some diabetes monitoring and management systems currently in use do not provide a visual aid other than requiring such households to use different-colored cases to distinguish between the different units. The present technology can allow for modified graphical displays where an indication of the source of the collected analyte, glucose or insulin data can be generated and flagged in the appropriate SRDS and subsequently incorporated as part of one or more of the modified graphical displays described above and presented to the correct user. FIG. 28 illustrates an exemplary modified display where a user's initials are incorporated in the display to identify the source of analyte data.

In some implementations, as part of the setup procedure for a new receiver or a receiver being used by a new user, the user will be asked to select a unique identifiable mark such as an initial, a screen-background, a color theme, a screen-saver, an animation or a combination of the above. The user's selection can be displayed as part of the modified graphical displays as described above. If an initial is selected, for example the initial 2804 in the modified display 2802 of FIG. 28, the initial 2804 can be displayed in a corner of the screen 2802 or in a status bar 2806 of the modified display 2808. A screensaver can be applied when the screen is not displaying a modified graphical display. A selected theme can be flagged in the SRDS and applied to entities fonts, backgrounds, etc. when generating a modified graphical display as described above. The selected animations can also be flagged and referenced in the SRDS to be displayed when generating the modified graphical displays as described above.

Other Example Graphical Displays Generated from SRDS

Figure 29:
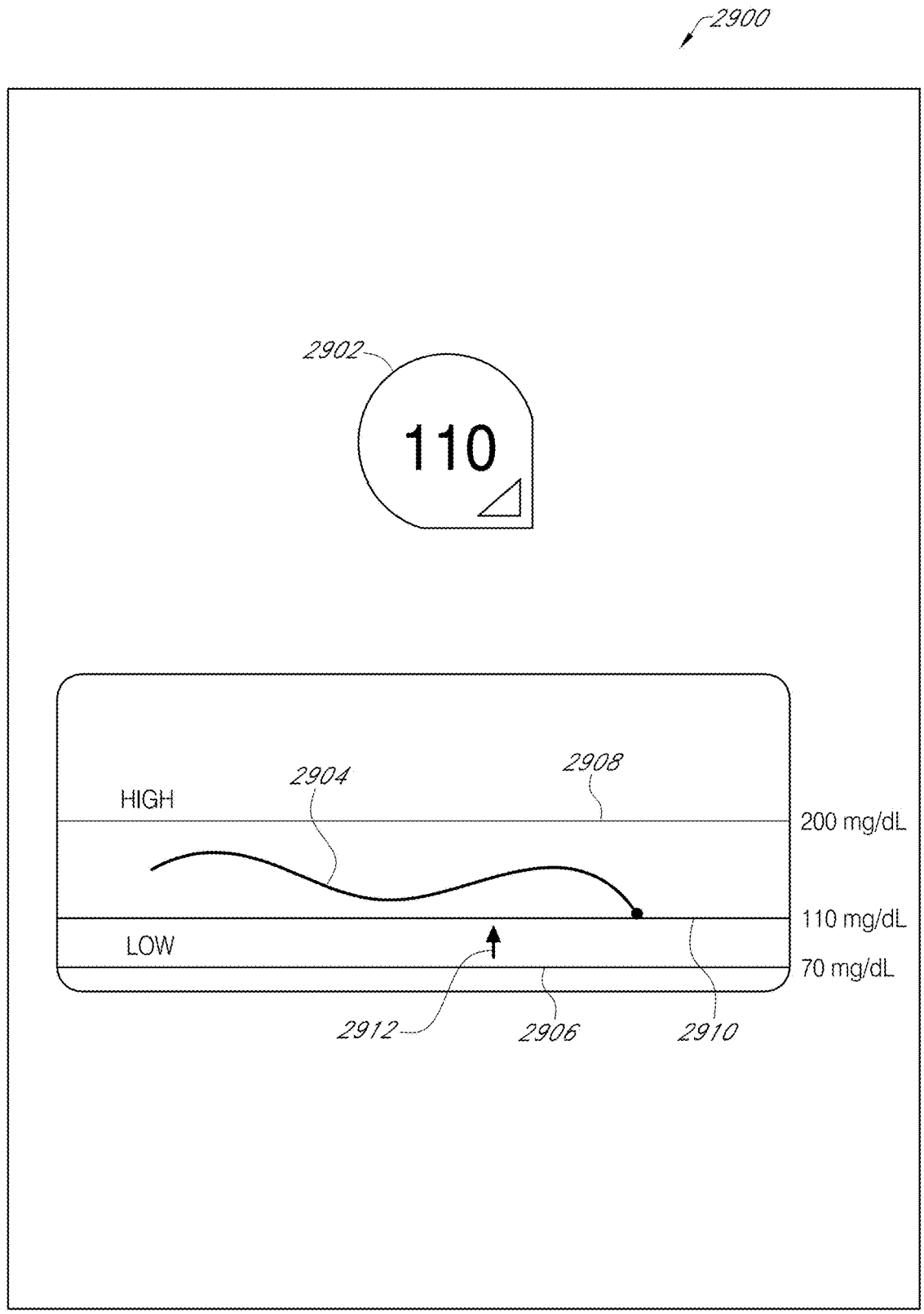
FIG. 29 illustrates a display conveying changes in analyte threshold values via animation.

FIG. 29 illustrates a modified graphical display 2900 according to an embodiment where a graphical display 2900 can automatically be modified when a user's health state is predicted to approach an undesirable state. In the context of diabetes management, for example, CGM readings from a user can indicate the user is approaching a hyperglycemic or hypoglycemic condition for which an alert can be generated. Undesirable health conditions such as hyperglycemic or hypoglycemic can be detected when magnitude of analyte concentration values exceed above a high blood glucose level threshold or drop below a low blood glucose level threshold. Alarm conditions can be triggered when the analyte concentration values exceed the high threshold or drop below the low threshold. The high and low thresholds under which alarm conditions can be generated may be user-defined, defined by a member of the patient's support team, or may be defined automatically by the system 302 based on user's data, profile, habits, past glucose trend values or other parameters related to the management of diabetes. The graphical display 2900 may initially be generated conveying diabetes health management data, such as mag glass 2902 and glucose trend graph 2904 relative to the previously defined or default high threshold line 2908 and the low threshold line 2906. In some cases, the previously-defined alarm thresholds may allow too much time to pass before the user is notified. For example, a previously defined alarm threshold, can be old or defined based on user's health data no longer applicable. In such cases, the user can potentially approach a critical condition and experience negative health consequences before the user is notified. To encourage the user to promptly take corrective action, it is desirable to automatically modify the relevant thresholds linked to alarm conditions to timely generate one or more alarms. In some embodiments, the system 302 can determine a rate at which the concentration of analyte values is approaching a high or low threshold and determine a time by which the analyte concentration values may reach a threshold. If the determined time is equal to or less than a predetermined safety time, the system 302 can automatically modify the thresholds linked to alarm conditions from their previously set value to the current analyte value to immediately trigger alarm conditions, notify the user and spur corrective action.

For example, a hypoglycemic alarm condition may have been preset to trigger an alarm if the user's blood glucose level drops below a low threshold 2906 corresponding to a drop in blood glucose level 70 mg/dL or more. The graphical display 2900 is generated depicting an analyte trend graph 2904 and the low threshold line 2906 as well as other relevant diabetes management data, such as mag glass 2902.

The blood glucose readings and other data obtained regarding the condition of the user may enable the system 302 to predict that a modification of a previously set alarm condition is desirable. For example, user analyte measurements and event data may suggest that the user's blood glucose level is currently 110 mg/dL and dropping at a rate of 2 mg/dL per minute. At this rate, the user's blood glucose level can reach an alarm level, 70 mg/dL, in approximately 20 minutes. In some circumstances, it may not be desirable or safe to postpone corrective action for 20 minutes. For example, a safety time of 20 minutes or more may be needed to effectively take a corrective action and realize result before analyte concentration values reach unhealthy ranges. When the system 302 determines that the user will reach a threshold in less time than the safety time, it can overwrite the existing threshold values linked to alarm conditions, trigger the alarm conditions and notify the user immediately. The system 302 can modify the graphical display 2900 as described above to raise the low threshold level 2906 to a new low threshold level 2910 corresponding to the current blood glucose level of 110 mg/dL. An alarm is immediately generated and the user is notified. The user can take corrective measure to avoid a critical condition.

Modification of the graphical display 2900 and the threshold 2906 can be accompanied by audible alarms and visual cues to attract attention and inform the user of the changes made. For example, the low threshold line 2906 can move upward to its new position 2910, where the movement of the threshold line is accompanied by audible alarm, and blinking or sweeping motion of the lines 2906 to its new position 2910. An arrow 2912 can point in the direction of the move and blink, pulsate or otherwise call attention to the change.

Figure 30:
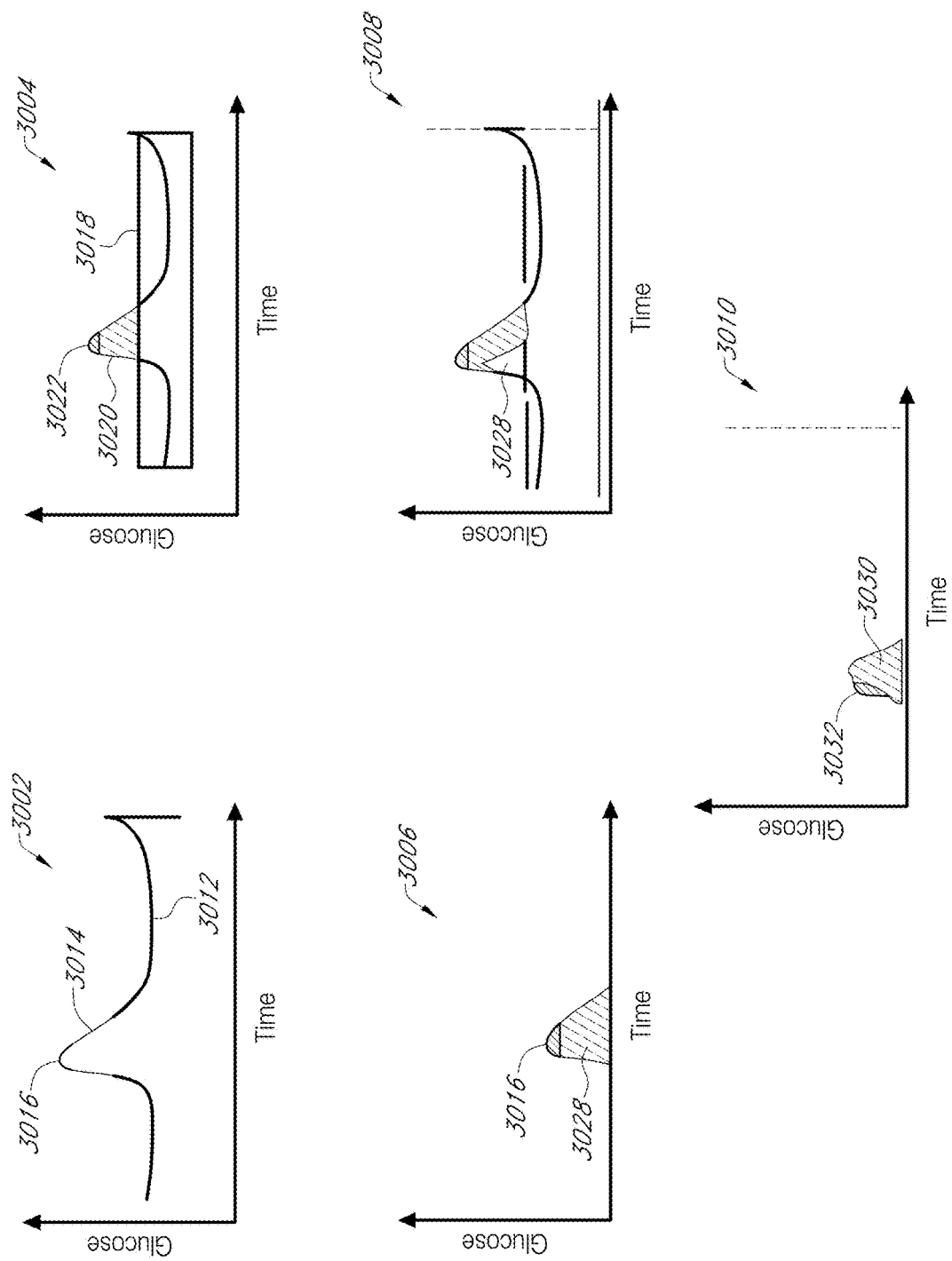
FIG. 30 illustrates analyte graphs depicting analyte measurements in relation to expected ranges of analyte values.

FIG. 30 illustrates modified graphical displays 3002, 3004, 3006, 3008 and 3010 generated from the data structures and arrangements of data according to an embodiment where the graphical displays 3002, 3004, 3006, 3008 and 3010 include visuals indicating ranges of analyte data. The system 302 automatically by default or via the user input can define various ranges of concentration of analyte data. For example, a target range of analyte concentration can be defined as when the analyte concentration value is a value between a desired high and low threshold. A caution range can be defined as when the analyte concentration value is a value between the desired high and low threshold, but close to one of those thresholds such that it may exceed the desired high threshold or drop below the desired low threshold in a short time. An outside-target range can be defined as when concentration of analyte value has exceeded a high threshold or fallen below a low threshold. High and low thresholds used to determine ranges of analyte data can be compiled based on anonymous data and/or analyte data of other users similarly situated to the user. Target range, caution range, and outside-target range can be user defined or automatically defined by the system 302 based on guidelines from health care organizations or authorities. For example, target range can be defined from the guidelines of American Diabetes Association (ADA) as fasting blood glucose level of less than 100 mg/dL and 2 hours postprandial glucose level of less than 140 mg/dL. In some implementations, analyte concentration value exceeding 20% of the ADA guidelines can be considered in caution range. For example, analyte concentration values below 80 mg/dL when fasting are considered in target range; analyte concentration values between 80 mg/dL and 100 mg/dL when fasting are considered in caution range and analyte concentration values exceeding 100 mg/dL are considered outside target range.

Graphical displays 3002, 3004, 3006, 3008 and 3010 illustrate magnitude of analyte data on the vertical axis and time on the horizontal axis. When generating graphical displays 3002, 3004, 3006, 3008 and 3010, various visual techniques can be used to modify the analyte data to indicate the ranges of analyte data. Graphical display 3002 illustrates a modified graphical display of a graph of magnitude of analyte concentration value versus time, where the graph is modified to illustrate ranges of analyte data with varying contrast or line styles. In other implementations, color coding can be used to distinguish the target, caution and outside-target ranges. The self-referential dataset generating the display 3002 can be modified where the analyte data is flagged by an indication of its range (e.g., target, caution and outside-target). When generating the graphical display 3002, each flag can be accorded a line style, contrast, thickness, or other distinguishing visual indicators and subsequent pixels can be generated on the display 3002 based on these indicators. In the example embodiment 3002, analyte data in target range can be flagged and shown with line style 3012. Analyte data in caution range can be flagged and their corresponding flags associated with the line style 3014. The outside-target range analyte values can be flagged and their corresponding flags can be assigned the line style 3016. As described, other visual indicators, such as color, gradient, other line styles or animation can be used. The visual indicators associated with caution or outside-target ranges can be chosen to quickly attract and draw attention to the information conveyed. For example, a darker contrast line 3016 can be used to indicate outside-target analyte values.

Graphical display 3004 is similar to the graphical display 3002. Analyte data in target range can be further indicated via a rectangle 3018 surrounding in target analyte values. Analyte values in caution range can be highlighted with an area under the curve shaded in style 3020. Outside-target analyte values can be highlighted with an area under the curve shaded in style 3022 different than the style 3020 to provide visual differentiation and attract the user's attention.

Graphical display 3006 is similar to the graphical display 3004. The analyte values in target range have been subtracted and are not shown to highlight analyte values in the caution and outside-target ranges that may pose health problems and may require attention and corrective action. Graphical display 3006 allows a user to view analyte values 3024 in caution range and outside-target analyte values 3026.

Graphical displays 3008 and 3010 use an adaptive target region technique whereby the graphical displays are modified to account for analyte data variation that are expected to happen regardless of presence or absence of diabetes. For example, a non-diabetic person, like a diabetic person, can experience a peak in blood glucose levels following consumption of a meal. For example, the graphical display 3008 can be modified to adjust the caution region 3028 based on event data obtained from the user and/or sensors. Such adjustments may be desired to avoid unnecessarily alarming a user. For example, if a meal event is detected, a rise in the user's blood glucose level may be expected and normal. The caution range 3028 in the relevant time frame can be adjusted to account for the expected rise in blood glucose level, for example by shading an area under the curve in the caution region 3028 with the same shade as used for in target analyte values. The graphical display 3010 uses the same adaptive target region technique as described in relation to the display 3008; however, the analyte values in target range have been subtracted and are not shown to further highlight and draw attention to analyte values in caution range 3030 and analyte values in outside target range 3032.

Figure 31:
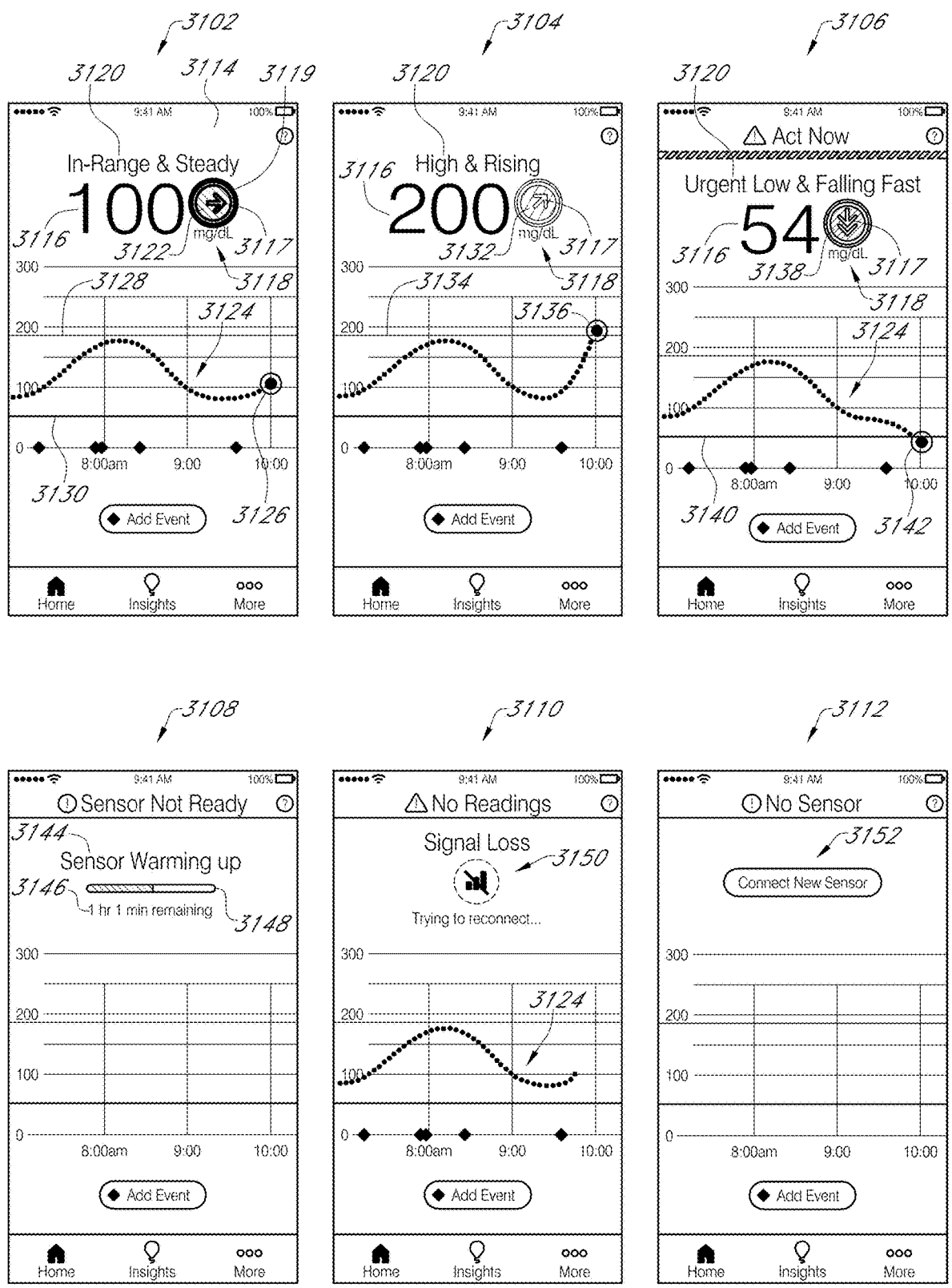
FIG. 31 illustrates exemplary modified graphical displays conveying information about the concentration of analyte values in a host, threshold values, related analyte graphs and/or analyte monitoring system status and reports.

FIG. 31 illustrates modified graphical displays generated from the data structures and arrangements of data according to an embodiment where the graphical displays 3102, 3104, 3106, 3108, 3110 and 3112 include visuals indicating status of analyte monitoring system, status of user's health, trends, alarms or other data relevant to the user's health. The graphical displays illustrated can for example use a reversed out or dark background 3114 to increase contrast and improve readability. Updated, current analyte value readings 3116 can be displayed via displaying a number, for example 100 mg/dL. An analyte trend indicator 3118 can be displayed nested next to updated current glucose 3116. The analyte trend indicator 3118 includes an arrow 3117 surrounded by a circle 3122 where the direction of the arrow 3117 indicates the future trend of analyte data. The circle 3122 surrounding the arrow 3117 can be filled with a shading style appropriate for indicating the trend or direction of future analyte values and/or to provide contrast with the background 3114 to improve readability. In some embodiments, the trend indicator 3118 includes a faded ring 3119 surrounding the circle 3122. A textual description 3120 of status and/or trend of analyte data values can be displayed near or above the current value of the analyte data 3116 (e.g., "In-Range & Steady"). Display 3102 can include an analyte graph 3124 where magnitude of analyte concentration values are depicted on the vertical axis versus time on the horizontal axis. A dot 3126 can indicate current analyte value on the analyte graph 3124. The dot 3126 is surrounded by a faded ring which in some embodiments can pulsate at the same rate and be rendered in the same style as the faded ring 3119 of the analyte indicator 3118. The analyte graph 3124 also depicts the high threshold line 3128 corresponding to the upper range of desirable analyte concentration values. The graph 3124 also depicts the low threshold line 3130 corresponding to the lower range of desirable analyte concentration values.

Display 3104 is similar to the display 3102. The user's current glucose level 3116 has reached 200 mg/dL, an upper range of desirable analyte concentration value. The trend indicator 3118 has been updated to indicate a current and feature trend of analyte concentration values. The arrow 3117 has been updated to point moderately upward. The circle 3122 is updated and filled with a shading style 3132 different than the shading style of circle 3122 to draw attention to the currently high analyte concentration values. The textual description 3120 has also been updated with appropriate text to indicate the analyte concentration values are high and rising. The high threshold line 3128 has been updated and rendered in the style 3134 different than the line style 3128 to draw attention to the high current value of analyte concentration. In some embodiments, the different style of line 3134 can include rendering that line in bolder, higher contrast style to draw attention of a user. The dot 3126 is updated and rendered in a style 3136 different than the style used to generate dot 3126 to further draw attention to the high value of analyte concentration. The dot 3136 and the circle 3132 can be rendered in the same style and the faded rings surrounding them can pulsate at the same rate to draw attention to the high analyte concentration value. In some embodiments, the high threshold line 3134 can pulsate at the same rate as the dot 3136, the circle 3132 or the faded rings surrounding them.

Display 3106 is similar to the display 3102. The user's current glucose level 3116 has dropped to 54 mg/dL, a lower limit of desirable analyte concentration value. The trend indicator 3118 has been updated to indicate a current and future trend of analyte concentration values. The arrow 3117 has been updated to change shape and dramatically point downward. The circle 3122 is updated and filled with a shading style 3138 different than the shading style of circle 3122 to draw attention to the currently low analyte concentration values. The textual description 3120 has also been updated with appropriate text to indicate the analyte concentration values are low and continue to drop fast. The low threshold line 3130 has been updated and rendered in the style 3140 different than the line style 3130 to draw attention to the low current value of analyte concentration. In some embodiments, the different style of line 3140 can include rendering that line in bolder, higher contrast style to draw attention. The dot 3126 is updated and rendered in a style 3142 different than the style used to generate the dot 3126 to further draw attention to the low value of analyte concentration. The dot 3142 and the circle 3138 can be rendered in the same style and the faded rings surrounding them can pulsate at the same rate to draw attention to the low analyte concentration value. In some embodiments, the low threshold line 3140 can pulsate at the same rate as the dot 3142, the circle 3138 or the faded rings surrounding them.

The user data, numbers, thresholds, graphs, and future predictions described above in relation to displays of FIG. 31 are exemplary and other user data may trigger different displays, texts, graphs and/or thresholds without departing from the spirit of the described technology.

As described, the analyte graph 3124 of analyte data values can be displayed where the magnitude of analyte values are plotted over a time period. The current value of analyte data can be indicated by a pulsating graphic 3126, for example, a graphic including one or two concentric circles with gradual fading out in the radial direction. The analyte graph 3124 and data structures generating the analyte graph 3124 can be dynamically updated based on current analyte sensor data. The data structures generating the displays 3102, 3104, 3106 or similar displays can be modified to display one or more pulsating animation, which may pulsate in sync to further draw the user's attention to information related to health management. Examples of display elements which can be modified or rendered with pulsating animation include, the trend indicator 3118, the current analyte value dot 3126, and the threshold lines 3128 and 3130.

Other status information relating to the operation of the analyte monitoring system can be conveyed via modified graphical displays 3108, 3110 and 3112. For example, the modified graphical display 3108 can indicate via texts 3144 and 3146 that the analyte sensor is warming up and how much time may be remaining before the sensor is ready. A status bar 3148 can also provide a visual of the status of the sensor. Graphical displays 3110 and 3112 are modified graphical displays reporting status of the system 302. For example, graphical display 3110 illustrates a situation where a loss of signal from the glucose sensor is encountered. Loss of signal can be indicated via text and graphical display elements 3150. The analyte graph 3124 no longer displays the current analyte value dot 3126. Other information such as current analyte concentration 3116 and analyte trend indicator 3118 are also not displayed. Text, graphical displays, icons and symbols 3150 are utilized to indicate a signal loss and alert the user. In graphical display 3112, no sensor is detected and text, graphical symbols and/or icons 3152 are used to indicate the absence of analyte sensor and to invite the user to connect an analyte sensor.

For ease of explanation and illustration, in some instances the detailed description describes exemplary systems and methods in terms of a continuous glucose monitoring environment; however, it should be understood that the scope of the invention is not limited to that particular environment, and that one skilled in the art will appreciate that the systems and methods described herein can be embodied in various forms. Accordingly, any structural and/or functional details disclosed herein are not to be interpreted as limiting the systems and methods, but rather are provided as attributes of a representative embodiment and/or arrangement for teaching one skilled in the art one or more ways to implement the systems and methods, which may be advantageous in other contexts.

For example, and without limitation, described monitoring systems and methods may include sensors that measure the concentration of one or more analytes (for instance glucose, lactate, potassium, pH, cholesterol, isoprene, and/or hemoglobin) and/or other blood or bodily fluid constituents of or relevant to a host and/or another party.

By way of example, and without limitation, monitoring system and method embodiments described herein may include finger-stick blood sampling, blood analyte test strips, non-invasive sensors, wearable monitors (e.g. smart bracelets, smart watches, smart rings, smart necklaces or pendants, workout monitors, fitness monitors, health and/or medical monitors, clip-on monitors, and the like), adhesive sensors, smart textiles and/or clothing incorporating sensors, shoe inserts and/or insoles that include sensors, transdermal (i.e. transcutaneous) sensors, and/or swallowed, inhaled or implantable sensors.

In some embodiments, and without limitation, monitoring systems and methods may comprise other sensors instead of or in additional to the sensors described herein, such as inertial measurement units including accelerometers, gyroscopes, magnetometers and/or barometers; motion, altitude, position, and/or location sensors; biometric sensors; optical sensors including for instance optical heart rate monitors, photoplethysmogram (PPG)/pulse oximeters, fluorescence monitors, and cameras; wearable electrodes; electrocardiogram (EKG or ECG), electroencephalography (EEG), and/or electromyography (EMG) sensors; chemical sensors; flexible sensors for instance for measuring stretch, displacement, pressure, weight, or impact; galvanometric sensors, capacitive sensors, electric field sensors, temperature/thermal sensors, microphones, vibration sensors, ultrasound sensors, piezoelectric/piezoresistive sensors, and/or transducers for measuring information of or relevant to a host and/or another party.

In this document, the terms "computer program medium" and "computer usable medium" and "computer readable medium", as well as variations thereof, are used to generally refer to transitory or non-transitory media such as, for example, main memory, storage unit interface, removable storage media, and/or channel. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module or a processor thereof or connected thereto to perform features or functions of the present disclosure as discussed herein.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system, comprising:
   a continuous analyte sensor configured to obtain analyte measurements of a host;
   a wireless transmitter configured to receive the analyte measurements from the continuous analyte sensor and at least partially process the analyte measurements to produce one or more datasets of analyte data, each dataset comprising an analyte concentration value associated with a time for one or more of the analyte measurements, wherein the wireless transmitter comprises an energy storage unit, a data converter unit, a processing unit and a transmitter unit; and
   an analyte data processing module operable on a mobile computing device in wireless communication with the wireless transmitter, the analyte data processing module configured to receive and process the one or more datasets from the wireless transmitter to produce a graphical display on the mobile computing device, wherein the graphical display comprises an arrangement of the analyte concentration values over a plurality of time intervals that is graphically modified to indicate one or more patterns in analyte data, and wherein the analyte data processing module is further configured to:
   aggregate groups of analyte data;
   flag the groups of analyte data based on additional information corresponding to one or more graphical displays;
   arrange the flagged groups of analyte data; and
   generate a self-referential dataset from the arranged groups of analyte data.

2. The system of claim 1, wherein generation of the self-referential dataset further comprises one or more of:
   flagging the analyte data based on one or more high and low thresholds of analyte in the host;
   flagging the analyte data based on performing statistical analysis of the analyte data; and
   flagging the analyte data based on contextual data related to when the analyte data was obtained.

3. The system of claim 2, wherein contextual data comprises: data indicative of one or more physical locations where analyte data was obtained, relationship between the host and the physical locations, frequency of visiting the physical locations, meals taken, type and intensity of exercise, type and amount of insulin administered and likelihood of the host being asleep or awake when the analyte data was obtained.

4. The system of claim 1, wherein the analyte data processing module is further configured to produce the graphical display on the mobile computing device by:
   receiving a user's input comprising the user's desired graphical display;
   receiving display configuration data;
   regenerating the self-referential dataset when the self-referential dataset does not contain data to form the desired graphical display; and
   reformatting the self-referential dataset based on the user's input and the display configuration data.

5. The system of claim 1, wherein the analyte data processing module is further configured to modify the graphical display by:
   scanning the self-referential dataset for threshold flags and modifying the graphical display based on threshold flags;
   scanning the self-referential dataset for statistical analysis flags and modifying the graphical display based on statistical analysis flags; and
   scanning the self-referential dataset for analyte contextual data flags and modifying the graphical display based on contextual data flags.

6. The system of claim 1, wherein the modification of the graphical display comprises displaying a clustering of colors, gradients of colors or shades, lining up of regions, or lighter or darker shades of overlapping regions to modify the arrangement of the analyte concentration values over the plurality of time intervals.

7. The system of claim 1, wherein the one or more patterns indicate the analyte concentration values relative to high and low analyte level thresholds for the host.

8. The system of claim 1, wherein the graphical display comprises concentric rings, or a fan-shaped graph, or an isometric graph plotted over 24 hour periods over 7 days, wherein the isometric graph is displayable in a three dimensional view.

9. A system, comprising:
a continuous analyte sensor configured to obtain analyte measurements of a host;
a wireless transmitter configured to receive the analyte measurements from the continuous analyte sensor and at least partially process the analyte measurements to produce one or more datasets of analyte data, each dataset comprising an analyte concentration value associated with a time for one or more of the analyte measurements, wherein the wireless transmitter comprises an energy storage unit, a data converter unit, a processing unit and a transmitter unit; and
an analyte data processing module operable on a mobile computing device in wireless communication with the wireless transmitter, the analyte data processing module configured to receive and process the one or more datasets from the wireless transmitter to produce a graphical display on the mobile computing device, wherein the graphical display comprises an arrangement of the analyte concentration values over a plurality of time intervals that is graphically modified to indicate one or more patterns in analyte data, wherein the arrangement includes a spatial-temporal organization of the analyte concentration values in which the analyte concentration values are positioned along a first direction according to a first time scale and along a second direction according to a second time scale, and an analyte level of the analyte concentration values is composed by one or more of a shape, color, shading, or size based on a magnitude of the analyte level.

10. The system of claim 9, wherein the first time scale is hourly and the second time scale is daily, wherein the graphical modification includes an analyte level trace overlaid on the graphical display such that higher analyte levels are closer to an outer curved region of the graphical display and lower analyte levels are closer to an inner curved region of the graphical display, or vice versa.

11. The system of claim 10, wherein the higher analyte levels are in a first color, the lower analyte levels are in a second color, and analyte levels between the higher and lower analyte levels are in a third color.

12. A computer-implemented method, comprising:
receiving, at a mobile computing device, analyte data obtained from a continuous analyte sensor device, wherein the analyte data includes analyte concentration values each associated with a measurement of time;
processing, at the mobile computing device, the analyte data to produce an arrangement of the analyte concentration values over a plurality of time intervals;
generating a graphic of the arrangement of the analyte concentration values;
modifying the graphic to indicate one or more patterns in the analyte data; and
displaying, at the mobile computing device, the modified graphic.

13. The method of claim 12, wherein the processing further comprises:
aggregating groups of analyte data;
flagging the groups of analyte data based on additional information corresponding to one or more graphical displays;
arranging the flagged groups of analyte data; and
generating a self-referential dataset from the arranged groups of analyte data.

14. A system comprising:
a continuous analyte sensor configured to obtain analyte measurements of a host;
a wireless transmitter configured to receive the analyte measurements from the continuous analyte sensor; and
analyte data processing module operable on a mobile computing device in wireless communication with the wireless transmitter, the analyte data processing module configured to:
receive at least a portion of the analyte measurements;
generate a self-referential dataset based in part on the analyte measurements;
generate one or more graphical displays based on the self-referential dataset;
modify the self-referential dataset; and
display one or more modified graphical displays based on the modified self-referential dataset.

15. The system of claim 14, wherein the analyte data processing module is further configured to:
generate high or low threshold values of analyte concentration in the host based in part on one or more of health data obtained from the host, statistical analysis of the analyte measurements, contextual data related to the analyte measurements, health data derived from a profile of the host, or health data obtained from one or more health data databases;
determine a time by which the host's analyte measurements reach the high or low threshold values;
modify one or more of the high or low thresholds when the time is equal to or less than a predetermined safety time; and
regenerate the self-referential dataset to display an animation indicating a change in threshold values.

16. The system of claim 15, wherein the one or more modified graphical displays comprise a graph of analyte measurements versus time and wherein the animation comprises moving a blinking threshold line from a first value to a current analyte value of the host.

17. The system of claim 14, wherein one or more of the graphical displays comprise a line graph of analyte measurements versus time and wherein the analyte data processing module is further configured to:
determine one or more expected ranges of analyte values; and
modify the self-referential dataset to display the analyte measurements based on the expected ranges of analyte values.

18. The system of claim 17, wherein the expected ranges of analyte values are based on one or more of input from the host, contextual data related to the analyte measurements or health data from health care organizations or healthcare authorities.

19. The system of claim 17, wherein the self-referential dataset is modified to use color, line styles, animation, shading, gradient or other visual differentiators to display the analyte measurements in relation to the expected ranges.

20. The system of claim 17, wherein the expected ranges of analyte values comprise a target range, a caution range and an outside-target range.

21. The system of claim 20, wherein the self-referential dataset is modified to subtract analyte values in target range and only display analyte values in caution and outside-target ranges.

22. The system of claim 17, wherein the expected ranges of analyte values are modified based on event data obtained from the host.

23. The system of claim 14, wherein one or more of the modified graphical displays comprise a numerical display of a current value of the analyte measurements, an indication of a prediction of a future trend of analyte measurements, a textual phrase indicating current status and the prediction of the future trend of analyte measurements, a graph of the analyte measurements versus time, one or more lines indicating high and low threshold values of analyte concentration in the host and a graphical representation on the graph of analyte indicating the current value of the analyte measurements.

24. The system of claim 23, wherein the self-referential dataset is dynamically modified based on analyte measurements and the self-referential dataset is further modified to indicate current analyte measurement values reaching or exceeding a threshold of the analyte concentration values in the host and wherein the indication of the prediction of the future trend of analyte measurements, a threshold line associated with the threshold being reached or exceeded and the graphical representation of the current analyte value on the analyte graph change style and pulsate in unison.

25. The system of claim 23, wherein the analyte data processing module is further configured to generate one or more audible alarms when an analyte threshold value is reached or exceeded.

26. The system of claim 14 wherein the self-referential dataset is modified to display one or more system status messages.

* * * * *